US006277608B1

(12) United States Patent
Hartley et al.

(10) Patent No.: US 6,277,608 B1
(45) Date of Patent: *Aug. 21, 2001

(54) RECOMBINATIONAL CLONING USING NUCLEIC ACIDS HAVING RECOMBINATION SITES

(75) Inventors: James L. Hartley, Frederick; Michael A. Brasch, Gaithersburg; Gary F. Temple, Washington Grove; Donna K. Fox, Sykesville, all of MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/296,280

(22) Filed: Apr. 22, 1999

Related U.S. Application Data

(62) Division of application No. 09/177,387, filed on Oct. 23, 1998.
(60) Provisional application No. 60/065,930, filed on Oct. 24, 1997.

(51) Int. Cl.[7] .......................... C12N 15/64; C12N 15/00; C07H 23/04; C12Q 1/68

(52) U.S. Cl. .................. 435/91.4; 435/6; 435/91.42; 435/320.1; 435/69.1; 435/91.1; 536/23.1; 536/24.2

(58) Field of Search .............. 435/6, 91.42, 320.1, 435/69.1, 91.1; 536/23.1, 24.2

(56) References Cited

U.S. PATENT DOCUMENTS

| | | | |
|---|---|---|---|
| 4,673,640 | 6/1987 | Backman ........................ 435/69.1 |
| 4,743,546 | 5/1988 | Backman et al. ................ 435/108 |
| 4,959,317 | 9/1990 | Sauer ............................. 435/462 |
| 5,227,288 | 7/1993 | Blattner ............................. 435/6 |
| 5,286,632 | 2/1994 | Jones ........................... 435/91.2 |
| 5,354,668 | 10/1994 | Auerbach ....................... 435/91.1 |
| 5,434,066 | 7/1995 | Bebee et al. .................... 435/475 |
| 5,470,727 | 11/1995 | Mascarenhas et al. ........... 435/473 |
| 5,591,609 | 1/1997 | Auerbach ....................... 435/91.2 |
| 5,614,389 | 3/1997 | Auerbach ....................... 435/91.2 |
| 5,635,381 | 6/1997 | Hooykaas et al. ............... 800/294 |
| 5,650,308 | 7/1997 | Baum ............................ 435/485 |
| 5,658,772 | 8/1997 | Odell et al. .................... 435/288 |
| 5,677,170 | 10/1997 | Devine et al. ................ 435/320.1 |
| 5,677,177 | 10/1997 | Wahl et al. ..................... 435/325 |
| 5,710,248 | 1/1998 | Grose ............................. 530/327 |
| 5,723,765 | 3/1998 | Oliver et al. .................... 800/205 |
| 5,733,733 | 3/1998 | Auerbach ........................... 435/6 |
| 5,733,743 | 3/1998 | Johnson et al. ................ 435/69.1 |
| 5,744,336 | 4/1998 | Hodges et al. ................ 435/320.1 |
| 5,776,449 | 7/1998 | Baum ............................ 424/93.2 |
| 5,830,707 | 11/1998 | Bushman ....................... 435/69.7 |
| 5,837,242 | 11/1998 | Holliger et al. ................ 424/136.1 |
| 5,843,772 | 12/1998 | Devine et al. .................. 435/69.1 |
| 5,851,808 | 12/1998 | Elledge et al. .................. 435/91.4 |
| 5,858,657 | 1/1999 | Winter et al. ....................... 435/6 |
| 5,871,907 | 2/1999 | Winter et al. ....................... 435/6 |
| 5,874,259 | 2/1999 | Szybalski ...................... 435/91.1 |
| 5,888,732 | 3/1999 | Hartley et al. ...................... 435/6 |
| 5,916,804 | 6/1999 | Bushman ........................ 435/325 |
| 5,919,676 | 7/1999 | Graham et al. ................. 435/91.4 |
| 5,928,914 | 7/1999 | Leboulch et al. ................ 435/456 |
| 5,989,872 | 11/1999 | Luo et al. ...................... 435/91.2 |
| 6,010,884 | 1/2000 | Griffiths et al. ................. 435/69.7 |
| 6,143,557 | 11/2000 | Hartley et al. ................. 435/320.1 |
| 6,171,861 | 1/2001 | Hartley et al. .................. 435/455 |

FOREIGN PATENT DOCUMENTS

| | | |
|---|---|---|
| 2141412 | 2/1994 | (CA). |
| 0 160 571 | 11/1985 | (EP). |
| 0 300 422 | 1/1989 | (EP). |
| 1 035 208 A1 | 9/2000 | (EP). |
| WO 91/02801 | 3/1991 | (WO). |
| WO 91/16427 | 10/1991 | (WO). |
| WO 92/20791 | 11/1992 | (WO). |
| WO 93/15191 | 8/1993 | (WO). |
| WO 93/19172 | 9/1993 | (WO). |
| WO 94/01927 | 4/1994 | (WO). |
| WO 94/17176 | 8/1994 | (WO). |
| WO 95/00555 | 1/1995 | (WO). |
| WO 97/06265 | 2/1997 | (WO). |
| WO 97/09436 | 3/1997 | (WO). |
| WO 97/25446 | 7/1997 | (WO). |
| WO 97/32481 | 9/1997 | (WO). |
| WO 98/10086 | 3/1998 | (WO). |
| WO 98/53056 | 11/1998 | (WO). |
| WO 99/10488 | 3/1999 | (WO). |
| WO 99/21977 | 5/1999 | (WO). |
| WO 99/25851 | 5/1999 | (WO). |
| WO 99/55851 | 11/1999 | (WO). |
| WO 00/60091 | 10/2000 | (WO). |
| WO 01/05961 A1 | 1/2001 | (WO). |
| WO 01/11058 A1 | 2/2001 | (WO). |

OTHER PUBLICATIONS

Abremski, K., and Gottesman, S., "Purification of the Bacteriophage λ xis Gene Product Required for λ Excisive Recombination," *J. Biol. Chem.* 257:9658–9662 (1982).

Abremski, K., et al., "Studies on the Properties of P1 Site–specific Recombination: Evidence for Topologically Unlinked Products Following Recombination," *Cell* 32:1301–1311 (1983).

Abremski, K., et al., "Bacteriophage P1 Cre–loxP Site–specific Recombination: Site–specific DNA Topoisomerase Activity of the Cre Recombination Protein," *J. Biol. Chem.* 261:391–396 (1986).

(List continued on next page.)

Primary Examiner—David Guzo
Assistant Examiner—Gerald G Leffers, Jr.
(74) Attorney, Agent, or Firm—Sterne, Kessler, Goldstein & Fox, P.L.L.C.

(57) ABSTRACT

Recombinational cloning is provided by the use of nucleic acids, vectors and methods, in vitro and in vivo, for moving or exchanging segments of DNA molecules using engineered recombination sites and recombination proteins to provide chimeric DNA molecules that have the desired characteristic(s) and/or DNA segment(s).

23 Claims, 58 Drawing Sheets

OTHER PUBLICATIONS

Adams, D. E., et al., "Cre–lox Recombination in *Escherichia coli* Cells: Mechanistic Differences from the in Vitro Reaction," *J. Mol. Biol. 266:*266:661–673 (1992).

Anton, M. and Graham, F. L., "Site–Specific Recombination Mediated by an Adenovirus Vector Expressing the Cre Recombinase Protein: a Molecular Switch for Control of Gene Expression," *J. Virol. 69:*4600–4606 (Aug. 1995).

Araki, H., et al., "Site–specific Recombinase, R, Encoded by Yeast Plasmid pSR1," *J. Mol. Biol. 225:*25–37 (1992).

Argos, P., et al., "The intergrase family of site–specific recombinases: regional similarities and global diversity," *EMBO J. 5:*433–440 (1986).

Atlung, T., et al., "A versatile method for integration of genes and gene fusions into the λ attachment site of *Escherichia coli,*" *Gene 107:*11–17 (1991).

Ausubel, F. M., et al., "Mutagenesis by the Polymerase Chain Reaction," in *Current Protocols in Molecular Biology,* John Wiley & Sons, Inc., Boston, MA, (1995).

Balakrishnan, R., et al., "A gene cassette for adapting *Escherichia coli* strains as hosts for att–Int–mediated rearrangement and $P_L$ expression vectors," *Gene 138:*101–104 (Jan. 1994).

Bayley, C. C., et al., "Exchange of gene activity in transgenic plants catalyzed by the Cre–lox site–specific recombination system," *Plant Mol. Biol. 18:*353–361 (1992).

Black, L.W., "In vitro packaging into phage T4 particles and specific recircularization of phage lambda DNAs," *Gene 46:*97–101 (1986).

Bethke, B. and Sauer, B., "Segmental genomic replacement by Cre–mediated recombination: genotoxic stress activation of the p53 promoter in single–copy transformants," *Nucl. Acids Res. 25:*2828–2834 (Jul. 1997).

Bernard, P. and Couturier, M., "Cell Killing by the F Plasmid Ccdb Protein Involves Poisoning of Dna–topoisomerase II Complexes," *J. Mol. Biol. 226:*735–745 (1992).

Bernard, P., et al., "Positive–selection vectors using the F plasmid ccdB killer gene," *Gene 148:*71–74 (Oct. 1994).

Betz, U. A. K., et al., "Bypass of lethality with mosaic mice generated by Cre–loxP–mediated recombination," *Curr. Biol. 6:*1307–1316 (Oct. 1996).

Bhandari, P and Gowrishankar, J., "An *Escherichia coli* host Strain Useful for Efficient Overproduction of Cloned Gene Products with Nacl as the Inducer," *J. Bacteriol. 179:*4403–4406 (Jul. 1997).

Bochner, B. R., et al., "Positive Selection for Loss of Tetracycline Resistance," *J. Bacteriol. 143:*926–933 (1980).

Boyd, A. C., "Turbo cloning: a fast, efficient method for cloning PCR products and other blunt–ended DNA fragments into plasmids," *Nucl. Acids Res. 21:*817–821 (1993).

Broach, J. R., et al., "Recombination within the Yeast Plasmid 2μ Circle is Site–Specific," *Cell 29:*227–234 (1982).

Brunelli, J. P. and Pall, M. L., "A Series of Yeast/*Escherichia coli* λ Expression Vectors Designed for Directional Cloning of cDNAs and cre/lox–Mediated Plasmid Excision," *Yeast 9:*1309–1318 (1993).

Brunelli, J.P., and Pall, M.L., "Lambda/Plasmid Vector Construction by In Vivo cre/lox–Mediated Recombination," *BioTechniques 16:*1061–1064 (Jun. 1994).

Buchholz, F., et al., "A simple assay to determine the functionality of Cre of FLP recombination targets in genomic manipulation constructs," *Nucl. Acid Res. 24:*3118–3119 (Aug. 1996).

Buchholz, F., et al., "Different thermostabilities of FLP and Cre recombinases: implications for applied site–specific recombination," *Nucl. Acid Res. 24:*4256–4262 (Nov. 1996).

Zhang, Y. et al., "A new logic for DNA engineering using recombination in *Escherichia coli,*" *Nat. Genet. 20:*123–128 (Oct. 1998).

Bushman, W., et al., "Control of Directionality in Lambda Site Specific Recombination," *Science 230:*906–911 (1985).

Campbell, A. M., "Chromosomal Insertion Sites for Phages and Plasmids," *J. Bacteriol. 174:*7495–7499 (1992).

Chapin, S.J., et al., "Differential Expression of Alternatively Spliced Forms of MAP4: a Repertoire of Structurally Different Microtubule–binding Domains," *Biochem. 34:*2289–2301 (Feb. 1995).

Craig, N.L. and Nash, H.A., "The Mechanism of Phage, Lambda Site–specific Recombination: Site–specific Breakage of Dna by Int Topoisomerase," *Cell 35:*795–803 (1983).

Dale, E. C. and Ow, D. W., "Intra– and intermolecular site–specific recombination in plant cells mediated by bacteriophage P1 recombinase," *Gene 91:*79–85 (1990).

Dale, E. C. and Ow, D. W., "Gene transfer with subsequent removal of the selection gene from the host genome," *Proc. Natl. Acad. Sci. USA 88:*10558–10562 (1991).

Dang, D. T. and Perrimon, N., "Use of a Yeast Site–Specific Recombinase to Generate Embryonic Mosaics in Drosophila," *Develop. Genetics 13:*367–375 (1992).

Devine, S. E., and Boeke, J.D., "Efficient integration of artificial transposons into plasmid targets in vitro: a useful tool for DNA mapping, sequencing and genetic analysis," *Nucl. Acids Res. 22:*3765–3772 (Sep. 1994).

Diederich, L., et al., "New Cloning Vectors for Integration into the λ Attachment Site attB of the *Escherichia coli* Chromosome," *Plasmid 28:*14–24 (1992).

Dymecki, S. M., "A modular set of Flp, FRT and lacZ fusion vectors for manipulating genes by site–specific recombination," *Gene 171:*197–201 (Jun. 1996).

Elledge, S. J., et al., "λYES: A multifunctional cDNA expression vector for the isolation of genes by complementation of yeast and *Escherichia coli* mutations," *Proc. Natl. Acad. Sci. USA 88:*1731–1735 (1991).

Feil, R., et al., "Regulation of Cre Recombinase Activity by Mutated Estrogen Receptor Ligand–Binding Domains," *Biochem. Biophys. Res. Com. 237:*752–757 (Aug. 1997).

Ferguson, J., et al., "Construction and characterization of three yeast–*Escherichia coli* shuttle vectors designed for rapid subcloning of yeast genes on small DNA fragments," *Gene 16:*191–197 (1981).

Fiering, S., et al., "An 'in–out' strategy using gene targeting and FLP recombinase for the functional dissection of complex DNA regulatory elements: Analysis of the β–globin locus control region," *Proc. Natl. Acad. Sci. USA 90:*8469–8473 (1993).

Filutowicz, M., et al., "Purification of the *Escherichia coli* integration host factor (IHF) in one chromatographic step," *Gene 147:*149–150 (Sep. 1994).

Fukushige, S. and Sauer, B., "Genomic targeting with a positive–selection lox integration vector allows highly reproducible gene expression in mammalian cells," *Proc. Natl. Acad. Sci. USA 89:*7905–7909 (1992).

Gage, P.J. et al., "A Cell–Free Recombination System for Site–Specific Integration of Multigenic Shuttle Plasmids into the Herpes Simplex Virus Type 1 Genome," *J. Virol. 66:*5509–5515 (1992).

Geoffroy, F., et al., "A new phage display system to construct multicombinatorial libraries of very large antibody repertoires," *Gene 151*:109–113 (Dec. 1994).

Golic, K. G. and Lindquist, S., "The FLP Recombinase of Yeast Catalyzes Site–Specific Recombination in the Drosophila Genome," *Cell 59*:499–509 (1989).

Gu, H. et al., "Deletion of a DNA polymerase beta gene segment in T cells using cell type–specific gene targeting," *Science 265*:103–106 (Jul. 1994).

Hardy, S., et al., "Construction of Adenovirus Vectors through Cre–lox Recombination," *J. Virol. 71*:1842–1849 (Mar. 1997).

Hasan, N., and Szybalski, W., "Control of cloned gene expression by promoter inversion in vivo: construction of improved vectors with a multiple cloning site and the $P_{tac}$ promoter," *Gene 56*:145–151 (1987).

Hasan, N., et al., "*Escherichia coli* genome targeting, I. Cre–lox.mediated in vitro generation of ori⁻plasmids and their in vivo chromosomal integration and retrieval," *Gene 150*:51–56 (Dec. 1994).

Hashimoto–Gotoh, T., et al., "Improved vector, pHSG664, for direct streptomycin–resistance selection: cDNA cloning with G:C–tailing procedure and subcloning of double–digested DNA fragments," *Gene 41*:125–128 (1986).

Hoekstra, M. F., et al., "Shuttle Mutagenesis: Bacterial Transposons for Genetic Manipulations in Yeast," *Meth. Enzymol. 194*:329–342 (1991).

Hoess, R. H., et al., "The role of the loxP spacer region in P1 site–specific recombination," *Nucl. Acids Res. 14*:2287–2300 (1986).

Hoess, R. H., and Abremski, K., "The Cre–lox Recombination System," in: *Nucleic Acids and Molecular Biology, vol. 4*, ed. by Eckstein, F. and D. M. J. Lilley, Springer–Verlag, Berlin, pp. 99–109 (1990).

Holt, C.L., and May, G.S., "A novel phage λ replacement Cre–lox vector that has automatic subcloning capabilities," *Gene 133*:95–97 (1993).

Kanaar, R., et al., "Gin–Mediated Recombination of Catenated and Knotted DNA Substrates: Implications for the Mechanism of Interaction Between Cis–Acting Sites," *Cell 58*:147–159 (1989).

Kilby, N. J., et al., "Site–specific recombinases: tools for genome engineering," *Trends in Genetics 9*:413–421 (1993).

Kim, S. et al., "Lambda Int protein bridges between higher order complexes at two distant chromosomal loci attL and attR," *Science 256*:198–263 (1992).

Kozak, M., "Comparison of Initiation of Protein Synthesis in Procaryotes, Eucaryotes, and Organelles," *Microbiol. Rev. 47*:1–45 (1983).

Kozak, M., "An analysis of 5'–noncoding sequences from 699 vertebrate messenger RNAs," *Nucl. Acids Res. 15*:8125–8132 (1987).

Kozak, M., "Structural features in eukaryotic mRNAs that modulate the initiation of translation," *J. Biol. Chem. 266*:19867–19870 (1991).

Kühn, R., et al., "Inducible Gene Targeting in Mice," *Science 269*:1427–1429 (Sep. 1995).

Lasko, M., et al., "Targeted oncogene activation by site–specific recombination in transgenic mice," *Proc. Natl. Acad. Sci. USA 89*:6232–6236 (1992).

Lander, E.S., "The New Genomics: Global Views of Biology," *Science 274*:536–539 (Oct. 1996).

Landy, A., "Mechanistic and structural complexity in the site–specific recombination pathways of Int and FLP," *Curr. Op. Genet. Develop. 3*:699–707 (1993).

Landy, A., "Dynamic, Structural, and Regulatory Aspects of λ Site–Specific Recombination," *Annu. Rev. Biochem. 58*:913–949 (1989).

Lebreton, B., et al., "Mutations That Improve the Binding of Yeast FLP Recombinase to Its Substrate," *Genet. 118*:393–400 (1988).

Leong, J.M., et al., "Generation of single base–pair deletions, insertions, and substitutions by a site–specific recombination system," *Proc. Natl. Acad. Sci. USA 82*:6990–6994 (1985).

Lee, E. C., et al., "Genetic Analysis of *Escherichia coli* Integration Host Factor Interactions with Its Bacteriophage λ H' Recognition Site," *J. Bacteriol. 173*:609–617 (1991).

Liu, Q. et al., "The univector plasmid–fusion system, a method for rapid construction of recombinant DNA without restriction enzymes," *Curr. Biol. 8*:1300–1309 (Nov. 1998).

Luckow, V. A., et al., "Efficient Generation of Infectious Recombinant Baculoviruses by Site–Specific Transposon–Mediated Insertion of Foreign Genes into a Baculovirus Genome Propagated in *Escherichia coli,*" *J. Virol. 67*:4566–4579 (1993).

Maeser, S., and Kahmann, R., "The Gin recombinase of phage Mu can catalyse site–specific recombination in plant protoplasts," *Mol. Gen. Genet. 230*:170–176 (1991).

Mahillon, J., et al., "IS231 and other *Bacillus thuringiensis* transposable elements: a review," *Genetica 93*:13–26 (Nov. 1994).

Matsuzaki, H., et al., "Chromosome Engineering in *Saccharomyces cerevisiae* by Using a Site–Specific Recombination System of a Yeast Plasmid," *J. Bacteriol. 172*:610–681 (1990).

McCarthy, JE and Brimacombe, R., "Prokaryotic translation: the interactive pathway leading to initiation," *Trends Genet. 10*:402–407 (Nov. 1994).

Miki, T. et al., "Control of Segregation of Chromosomal Dna by Sex Factor F in *Escherichia coli*. Mutants of Dna Gyrase Subunit a Suppress letd (ccdb) Product Growth Inhibition," *J. Mol. Biol. 225*:39–52 (1992).

Mizuuchi, M. and Mizuuchi, K., "The extent of DNA sequence required for a functional bacterial attachment site of phage lambda," *Nucl. Acids Res. 13*:1193–1208 (1985).

Mozo, T. and Hooykaas, P. J. J., "Design of a novel system for the construction of vectors for Agrobacterium–mediated plant transformation," *Mol. Gen. Genet 236*:1–7 (1992).

Mullins, L.J., et al., "Efficient Cre–lox linerisation of BACs: applications to physical mapping and generation transgenic animals," *Nucl. Acids Res. 25*:2539–2540 (Jun. 1997).

Nagaraja, R. and Weisberg, R. A., "Specificity Determinants in the Attachment Sites of Bacteriophages HK022 and λ," *J. Bacteriol. 172*:6540–6550 (1990).

Nash, H.A. and Robertson, CA, "Purification and Properties of the *Escherichia coli* Protein Factor Required for Λ Integrative Recombination," *J. Biol. Chem. 256*:9246–9253 (1981).

Nash, H. A., "Purification and Properties of the Bacteriophage Lambda Int Protein," *Meth. Enzymol. 100*:210–216 (1983).

Nash, H. A., et al., "Role of homology in site–specific recombination of bacteriophageλ: Evidence against joining of cohesive ends," *Proc. Natl. Acad. Sci. USA 84*:4049–4053 (1987).

Nash, H. A., "Bending and supercoiling of DNA at the attachment site of bacteriophage Λ," *Trends Bicohem. Sci* 15:222–227 (1990).

Numrych, T. E., et al., "A comparison of the effects of single–base and triple–base changes in the integrase arm–type binding sites on the site–specific recombination of bacteriophage lambda," *Nucl. Acids Res.* 18:3953–3959 (1990).

Numrych, T.E., et al., "Characterization of the bacteriophage lambda excisionase (Xis) protein: the C–terminus is required for Xis–integrase cooperativity but not for DNA binding," *EMBO J.* 11:3797–3806 (1992).

Nunes–Düby, S.E., et al., "Half–att Site Substrates Reveal the Homology Independence and Minimal Protein Requirements for Productive Synapsis in λ Excisive Recombination," *Cell* 59:197–206 (1989).

Nunes Düby, S.E. et al., "Similarities and differences among 105 members of the Int family of site–specific recombinases," *Nucl. Acids Res.* 26:391–406 (Jan. 1998).

Oberto, J., et al., "A segment of the phage HK022 chromosome is a mosaic of other lambdoid chromosomes," *Nucl. Acids Res.* 22:354–356 (Feb. 1994).

Orban, P. C., et al., "Tissue– and site–specific DNA recombination in transgenic mice," *Proc. Natl. Acad. Sci. USA* 89:6861–6865 (1992).

Padgett, K. A. and Sorge, J. A., "Creating seamless junctions independent of restriction sites in PCR cloning," *Gene* 168:31–35 (Feb. 1996).

Palazzolo, M. J., et al., "Phage lambda cDNA cloning vectors for subtractive hybridization, fusion–protein synthesis and Cre–loxP automatic plasmid subcloning," *Gene* 88:25–36 (1990).

Pan, G., et al., "Ligation of Synthetic Activated DNA Substrates by Site–specific Recombinases and Topoisomerase I," *J. Biol. Chem.* 268:3683–3689 (1993).

Parks, R.J., and Graham, F.L., "A Helper–Dependent System for Adenovirus Vector Production Helps Define a Lower Limit for Efficient DNA Packaging," *J. Virol.* 71:3293–3298 (Apr. 1997).

Peakman, T. C., et al., "Highly efficient generation of recombinant baculoviruses by enzymatically mediated site–specific in vitro recombination," *Nucl. Acids Res.* 20:495–500 (1992).

Peredelchuk, M.Y., and Bennett, G.N., "A method for construction of *E. coli* strains with multiple DNA insertions in the chromosome," *Gene* 187:231–238 (Mar. 1997).

Pichel, J. G., et al., "Timing of SV40 oncogene activation by site–specfic recombination determines subsequent tumor progression during murine lens development," *Gene* 8:3333–3342 (1993).

Pierce, J. C., et al., "A positive selection vector for cloning high molecular weight DNA by the bacteriophage P1 system: Improved cloning efficacy," *Proc. Natl. Acad. Sci. USA* 89:2056–2060 (1992).

Podhajska, A. J., et al., "Control of cloned gene expression by promoter inversion in vivo: construction of the heat–pulse–activated att–nutL–p–att–N module," *Gene* 40:163–168 (1985).

Pósfai, G., et al., "In vivo excision and amplification of large segments of the *Escherichia coli* genome," *Nucl. Acids Res.* 22:2392–2398 (Jun. 1994).

Prasad, P. V., et al., "Substrate Recognition by the 2 µm Circle Site–Specific Recombinase: Effect of Mutations within the Symmetry Elements of the Minimal Substrate," *Mol. Cell. Biol.* 6:4329–4334 (1986).

Qian, X., et al., "Reactions between half– and Full–FLP Recombination Target Sites: A Model System for Analyzing Early Steps in FLP Protein–Mediated Site–Specific Recombination," *J. Biol. Chem.* 267:7794–7805 (1992).

Richet, E., et al., "The Interaction of Recombination Proteins with Supercoiled DNA: Defining the Role of Supercoiling in Lambda Integrative Recombination," *Cell* 46:1011–1021 (1986).

Richet, E., et al., "Synapsis of Attachment Sites during Lambda Integrative Recombination Involves Capture of a Naked DNA by a Protein–DNA Complex," *Cell* 52:9–17 (1988).

Sadowski, P., "Site–Specific Recombinases: Changing Partners and Doing the Twist," *J. Bacteriol.* 165:341–347 (1986).

Sadowski, P.D., "The Flp Recombinase of the 2–microns Plasmid of *Saccharomyces cerevisiae*," *Prog. Nucl. Acid Res. Mol. Biol.* 51:53–91 (1995).

Sauer, B., et al., "Site–specific insertion of DNA into a pseudorabies virus vector," *Proc. Natl. Acad. Sci. USA* 84:9108–9112 (1987).

Sauer, B., "Functional Expression of the cre–lox Site–Specific Recombination System in the Yeast *Saccharomyces cerevisiae*," *Mol. Cell. Biol.* 7:2087–2096 (1987).

Sauer, B., and Henderson, N., "The cyclization of linear DNA in *Escherichia coli* by site–specific recombination," *Gene* 70:331–341 (1988).

Sauer, G. and Henderson, N., "Cre–stimulated recombination at loxP–containing DNA sequences placed into the mammalian genome," *Nucl. Acids Res.* 17:147–161 (1989).

Sauer, B., "Manipulation of Transgenes by Site–Specific Recombination: Use of Cre Recombinase," *Meth. Enzymol.* 225:890–900 (1993).

Sauer, B., "Site–specific recombination: developments and applications," *Curr. Op. Biotechnol.* 5:521–527 (Oct. 1994).

Sauer, B., "Multiplex Cre/lox recombination permits selective site–specific DNA targeting to both a natural and an engineered site in the yeast genome," *Nucl. Acids Res.* 24:4608–4613 (Dec. 1996).

Sauer, B., "Inducible Gene Targeting in Mice Using the Cre/lox system," *Methods* 14:381–392 (Apr. 1998).

Schindelhauer, D., and Cooke, H.J., "Efficient combination of large DNA in vitro: in gel site specific recombination (IGSSR) of PAC fragments containing α satellite DNA and the human HPRT gene locus," *Nucl. Acids Res.* 25:2241–2243 (Jun. 1997).

Schlake, T., and Bode, J., "Use of Mutated FLP Recognition Target (FRT) Sites for the Exchange of Expression Cassettes at Defined Chromosomal Loci," *Biochemistry* 33:12746–12751 (Nov. 1994).

Segall, A. M. and Nash, H. A., "Synaptic intermediates in bacteriophage lambda site–specific recombination: integrase can align pairs of attachment sites," *EMBO J.* 12:4567–4576 (1993).

Segall, A.M., and Nash, H.A., "Architectural flexibility in lambda site–specific recombination: three alternate conformations channel the attL site into three distinct pathways," *Genes to Cells* 1:453–463 (May 1996).

Sheffield, P. et al., "Overcoming Expression and Purification Problems of RhoGDI Using a Family of "Parallel" Expression Vectors," *Prot. Expr. Purif.* 15:34–39 (Feb. 1999).

Sizemore, C., et al., "Quantitative analysis of Tn10 Tet repressor binding to a complete set of tet operator mutants," *Nucl. Acids Res.* 18:2875–2880 (1990).

Smith, A. J. H., et al., "A site–directed chromosomal translocation induced in embryonic stem cells by Cre–loxP recombination," *Nat. Gen.* 9:376–385 (Apr. 1995).

Snaith, M.R., et al., "Multiple cloning sites carrying loxP and FRT recognition sites for the Cre and Flp site–specific recombinases," *Gene* 166:173–174 (Dec. 1995).

Spengler, S.J., et al., "The Stereostructure of Knots and Catenanes Produced by Phage λ Integrative Recombination: Implications for Mechanism and DNA Structure," *Cell* 42:325–334 (1985).

Thompson, J. F., et al., "Mutations in an Integration Host Factor–Binding Site: Effect on Lambda Site–Specific Recombination and Regulatory Implications," *J. Bacteriol.* 168:1343–1351 (1986).

Thompson, J.F., et al., "Helical–repeat dependence of integrative recombination of bacteriophage λ: Role of the P1 and H1 protein binding sites," *Proc. Natl. Acad. Sci. USA* 85:6323–6327 (1988).

Tsurushita, N., et al., "Phage display vectors for in vivo recombination of immunoglobulin heavy and light chain genes to make large combinatorial libraries," *Gene* 172:59–63 (May 1996).

Vanin, E.F., et al., "Development of High–Titer Retroviral Producer Cell Lines by Using Cre–Mediated Recombination," *J. Virol.* 71:7820–7826 (Oct. 1997).

Waterhouse, P., et al., "Combinatorial infection and in vivo recombination: a strategy for making large phage antibody repertoires," *Nucl. Acids Res.* 21:2265–2266 (1993).

Weisberg, R. A., Landy, A., "Site–specific Recombination in Phage Lambda," in: "*Lambada II,*" Hendrix, R. W. et al., eds., Cold Spring Harbor Laboratory Press, Cold Spring Harbor, N. Y., pp. 211–250 (1983).

Wierzbicki, A., et al., "A Mutational Analysis of the Bacteriophage P1 Recombinase Cre," *J. Mol. Biol.* 195:785–794 (1987).

Winoto, A.,et al., "Directional Control of Site–specific Recombination by Bacteriophage λ," *J. Mol. Biol.* 192:677–680 (1986).

Yang, W., and Mizuuchi, K., "Site–specific recombination in plane view," *Structure* 5:1401–1406 (Nov. 1997).

Abremski, K., and Hoess, R., "Bacteriophage P1 Site–specific Recombination—Purification and Properties of the Cre Recombinase Protein," *J. Biol. Chem.* 259:1509–1514 (1984).

Ausubel, F.M., et al., "Maps of Plasmids pBR322 and pUC19," in *Current Protocols in Molecular Biology*, John Wiley & Sons, Inc., Boston, MA, (1995).

Babineau, D. et al., "The FLP Protein of the 2–micro Plasmid of Yeast," *J. Biol. Chem.* 260:12313–12319 (1985).

Bloch, C.A., et al., "Purification of *Escherichia coli* Chromosomal Segments without Cloning," *Biochem. Biophys. Res. Comm.* 223:104–111 (1996).

Bubeck, P., et al., "Rapid cloning by homologous recombination in vivo," *Nucl. Acids Res.* 21:3601–3602 (1993).

Chatterjee, P.K., and Coren, J.S., "Isolating large nested deletions in bacterial and P1 artificial chromosomes by in vivo P1 packaging of products o Cre–catalysed recombination between the endogenous and a transposed loxP site," *Nucl. Acids Res.* 25:2205–2212 (1997).

Cox, M.M., "The FLP protein of the yeast 2–µm plasmid: Expression of a eukaryotic genetic recombination system in *Escherchia coli*," *Proc. Natl. Acad. Sci. USA* 80:4223–4227 (1983).

Degryse, E., "In vivo intermolecular recombination in *Escherichia coli*:application to plasmid constructions," *Gene* 170:45–50 (1996).

Francia, M.V., et al., "Gene Integration in the *Escherichia coli* Chromosome Mediated by Tn21 Integrase (Int21)," *J. Bacteriol.* 178:894–898 (Feb. 1996).

Glasgow, A.C., et al., "DNA–binding Properties of the Hin Recombinase," *J. Biol. Chem.* 264:10072–10082 (1989).

Guo, F., et al., "Asymmetric DNA bending in the Cre–loxP site–specific recombination synapse," *Proc. Natl. Acad. Sci. USA* 96:7143–7148 (1999).

Hoess, R.H., et al., "P1 site–specific recombination: Nucleotide sequence of the recombining sites," *Proc. Natl. Acad. Sci. USA* 79:3398–3402 (1982).

Hoess, R.H., et al., "Mechanism of Strand Cleavage and Exchange in the Cre–lox Site–specific Recombination System," *J. Mol. Biol.* 181:351–362 (1985).

Hoess, R., et al., "Formation of small circular DNA molecules via an in vitro site–specific recombination system," *Gene* 40:325–329 (1985).

Hoogenboom, H.R., et al., "Multi–subunit proteins on the surface of filamentous phage: methodologies for displaying antibody (Fab) heavy and light chains," *Nucl. Acid Res.* 19:4133–4137 (1991).

Lafontaine, D., and Tollervey, D., "One–step PCR mediated strategy for the construction of conditionally expressed and epitope tagged yeast proteins," *Nucl. Acids Res.* 24:2469–2472 (1996).

Medberry, S.L., et al., "Intra–chromosomal rearrangements generated by Cre–lox site–specific recombination," *Nucl. Acids Res.* 23:485–490 (1995).

Oliner, J.D., et al., "In vivo cloning of PCR products in *E. coli*," *Nucl. Acids Res.* 21:5192–5197 (1993).

Osborne, B.I., et al., "A system for insertional mutagenesis and chromosomal rearrangement using the Ds transposon and Cre–lox," *Plant J.* 7:687–701 (1995).

Senecoff, J.F., et al., "DNA Recognition by the FLP Recombinase of the Yeast 2µ Plasmid—A Mutational Analysis of the FLP Binding Site," *J. Mol. Biol.* 201:405–421 (1988).

Sternberg, N., et al., "Site–specific Recombination and Its Role in the Life Cycle of Bacteriophage P1," *Cold Spring Harbor Symp. Quant. Biol.* 45:297–309 (1981).

Sternberg, N., et al., "Bacteriophage P1 cre Gene and its Regulatory Region," *J. Mol. Biol.* 187:197–212(1986).

Sternberg, N., "Bacteriophage P1 cloning system for the isolation, amplification, and recovery of DNA fragments as large as 100 kilobase pairs," *Proc. Natl. Acad. Sci. USA* 87:103–107 (1990).

Storck, T., et al., "Rapid construction in yeast of complex targeting vectors for gene manipulation in the mouse," *Nucl. Acids Res.* 24:4594–4596 (1996).

Strathmann, M., et al., "Transposon–facilitated DNA sequencing," *Proc. Natl. Acad. Sci. USA* 88:1247–1250 (1991).

Thorpe, H.M., and Smith, M.C.M., "In vitro site-specfic integration of Bacteriophage DNA catalyzed by a recombinase of the resolvase/invertase family," Proc. Natl. Acad. Sci. USA 95:5505–5510 (May 1998).

Wang, G., et al., "pDUAL: A transposon–based cosmid cloning vector for generating nested deletions and DNA sequencing templates in vivo," Proc. Natl. Acad. Sci. USA 90:7874–7878 (1993).

Wasserman, S.A., et al., "The helical repeat of double-stranded DNA varies as a function of catenation and supercoiling," Nature 334:448–450 (1988).

Wild, J., et al., "A broad–host–range in vivo pop–out and amplification system for generating large quantities of 50- to 100–kb genomic fragments for direct DNA sequencing," Gene 179:181–188 (1996).

Wild, J., et al., "Targeting and retrofitting pre–existing libraries of transposon insertions with FRT and oriV elements for in–vivo generation of large quantities of any genomic fragment," Gene 223:55–66 (1998).

Yanisch–Perron, C., et al., "Improved M13 phage cloning vectors and host strains: nucleotide sequences of the M13mp18 and pUC19 vectors," Gene 33:103–119 (1985).

Yoon, Y.G., et al., "Cre/loxP–mediated in vivo excision of large segments from yeast genome and their amplification based on the 2 $\mu$m plasmid–derived system," Gene 223:67–76 (1998).

York, D., et al., "Simple and efficient generation in vitro of nested deletions and inversions: Tn5 intramolecular transposition," Nucl. Acids Res. 26:1927–1933 (1998).

Zhu, X.–D., et al., "Homology Requirements for Ligation and Strand Exchange by the FLP Recombinase," J. Biol. Chem. 270:11646–11653 (1995).

Albert, H., et al., "Site–specific integration of DNA into wild–type and mutant lox sites placed in the plant genome," Plant J. 7:649–659 Oxford Bios Scientific Publishers and Blackwell Scientific Publications In Association With The Society For Experimental Biology (1995).

Andrews, B. J., et al., "Interaction of the FLP Recombinase of the Saccharomyces cerevisiae 2$\mu$m Plasmid with Mutated Target Sequences," Mol. Cell. Biol. 6:2482–2489, American Society for Microbiology (1986).

Andrews, B. J., et al., "The FLP Recombinase of the 2$\mu$ Circle DNA of Yeast: Interaction with Its Target Sequences," Cell 40:795–803, Cell Press (1985).

Bernard, P., "Positive Selection of Recombinant DNA by CcdB," BioTechniques 21:320–323, Eaton Publishing Company (Aug. 1996).

Dale, E.C., and Ow, D.W., "Mutations in the Cre/lox Recombination Site Enhance the Stability of the Recombination Products: Applications for Gene Targeting in Plants," J. Cell. Biochem. 16(Suppl. F) :206, Abstract No. Y 108, Wiley–Liss, Inc. (1992).

Davies, J., and Riechmann, L., "An antibody VH domain with a lox–Cre site integrated into its coding region: bacterial recombination within a single polypeptide chain," FEBS Letts. 377:92–96, Elsevier Science B.V. (1995).

Hall, R.M., and Collins, C.M., "Mobile gene cassettes and intergrons: capture and spread of genes by site–specific recombination," Mol. Microbiol. 15:593–600, Blackwell Scientific Publications (1995).

Jaffré, A., et al., "Effects of the ccd Function of the F Plasmid on Bacterial Growth," J. Bacteriol. 163:841–849, American Society for Microbiology (1985).

Jayaram, M. "The Int family of site–specific recombinases: Some thoughts on a general reaction mechanism,"J. Gentet. 67:29–36, Indian Academy of Sciences (1988).

Krafte, D. S., et al., "Stable Expression and Functional Characterization of a Human Cardiac Na$^+$ Channel Gene in Mammalian Cells," J. Mol. Cell Cardiol. 27:823–830, Academic Press Limited (1995).

Lee, G., and Saito, I., "Role of nucleotide sequences of loxP spacer region in Cre–mediated recombination," Gene 216:55–65, Elsevier Science B.V. (Aug. 1998).

Lorbach, E., et al., "Site–specific Recombination in Human Cells Catalyzed by Phage $\lambda$ Integrase Mutants," J. Mol. Biol. 296:1175–1181, Academic Press, Inc. (2000).

Mizuuchi, K., and Mizuuchi, M., "Integrative Recombination of Bacteriophage $\lambda$: In Vitro Study of the Intermolecular Reaction," Cold Spring Harb. Symp. Quant. Biol. 43:1111–1114, Cold Spring Harbor Laboratory Press (1979).

Nash, H. A., "Integrative Recombination of Bacteriophage Lambda DNA In Vitro," Proc. Natl. Acad. Sci. USA 72:1072–1076, National Academy of Sciences of the USA (1975).

Reed, R. R., "Transposon–Mediated Site–Specific Recombination: A Defined in Vitro System," Cell 25:713–719, Cell Press (1981).

Reed, R. R., and Grindley, N.D.F., "Transposon–Mediated Site–Specific Recombination in Vitro: DNA Cleavage and Protein–DNA Linkage at the Recombination Site," Cell 25:721–728, Cell Press (1981).

Simpson, J. C., et al., "Systematic subcellular localizaion of novel proteins identified by large–scale cDNA sequencing," EMBO Reports 1:287–292, IRL Press Limited (2000).

Venkatesh, T. V., and Redding, C. M., "Ribosomal Protein S1 and NusA Protein Complexed to Recombination Protein $\beta$ of Phage $\lambda$," J. Bacteriol. 175:1844–1846, American Society for Microbiology (1993).

Zahra, D. G., et al., "Selective in–vivo recombination to increase antibody library size –an improved phage display vector systems," Gene 227:49–54, Elsevier Science Publishers B.V. (1999).

Dialog File 351 (Derwent World Patents Index), unverified English language abstract for WIPO/PCT Publication No. WO 98/53056 (Document No. AN4); WPI Accession No. 1999–000502/199901.

Dialog File 351 (Derwent World Patents Index), unverified English language abstract for WIPO/PCT Publication No. WO 99/25851 (Document No. AP4); WPI Accession No. 1999–347485/199929.

5.2kbPCRprod (5327 bps)

attB1AMPattB3 (987 bps)

attB1TETattB3 (1442 bps)

SEQUENCE LISTING

<160> NUMBER OF SEQ ID NOS: 60

<210> SEQ ID NO: 1
<211> LENGTH: 25
<212> TYPE: DNA
<213> ORGANISM: Unknown
<220> FEATURE:
<221> NAME/KEY: OTHER
<222> LOCATION: 18
<223> OTHER INFORMATION: "n" may be any nucleotide
<223> OTHER INFORMATION: Description of Unknown Organism: recombination
      products

<400> SEQUENCE: 1
rkycwgcttt yktrtacnaa stsgb                                              25

<210> SEQ ID NO: 2
<211> LENGTH: 25
<212> TYPE: DNA
<213> ORGANISM: Unknown
<220> FEATURE:
<221> NAME/KEY: OTHER
<222> LOCATION: 18
<223> OTHER INFORMATION: "n" may be any nucleotide
<223> OTHER INFORMATION: Description of Unknown Organism: recombination
      products

<400> SEQUENCE: 2
agccwgcttt yktrtacnaa ctsgb                                              25

<210> SEQ ID NO: 3
<211> LENGTH: 25
<212> TYPE: DNA
<213> ORGANISM: Unknown
<220> FEATURE:
<221> NAME/KEY: OTHER
<222> LOCATION: 18
<223> OTHER INFORMATION: "n" may be any nucleotide
<223> OTHER INFORMATION: Description of Unknown Organism: recombination
      products

<400> SEQUENCE: 3
gttcagcttt cktrtacnaa ctsgb                                              25

<210> SEQ ID NO: 4
<211> LENGTH: 25
<212> TYPE: DNA
<213> ORGANISM: Unknown
<220> FEATURE:
<221> NAME/KEY: OTHER
<222> LOCATION: 18
<223> OTHER INFORMATION: "n" may be any nucleotide
<223> OTHER INFORMATION: Description of Unknown Organism: recombination
      products

<400> SEQUENCE: 4
agccwgcttt cktrtacnaa gtsgb                                              25

<210> SEQ ID NO: 5
<211> LENGTH: 25
<212> TYPE: DNA
<213> ORGANISM: Unknown
<220> FEATURE:
<221> NAME/KEY: OTHER
<222> LOCATION: 18
<223> OTHER INFORMATION: "n" may be any nucleotide
<223> OTHER INFORMATION: Description of Unknown Organism: recombination
      products

<400> SEQUENCE: 5
gttcagcttt yktrtacnaa gtsgb                                              25

<210> SEQ ID NO: 6
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 6
agcctgcttt tttgtacaaa cttgt                                              25

<210> SEQ ID NO: 7
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 7
agcctgcttt cttgtacaaa cttgt                                              25

<210> SEQ ID NO: 8
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 8
acccagcttt cttgtacaaa gtggt                                              25

<210> SEQ ID NO: 9
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 9
gttcagcttt tttgtacaaa cttgt                                              25

<210> SEQ ID NO: 10
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 10
gttcagcttt cttgtacaaa cttgt                                              25

<210> SEQ ID NO: 11
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 11
gttcagcttt cttgtacaaa gtggt                                              25

<210> SEQ ID NO: 12
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 12
agcctgcttt tttgtacaaa gttgg                                              25

<210> SEQ ID NO: 13
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 13
agcctgcttt cttgtacaaa gttgg                                              25

<210> SEQ ID NO: 14
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 14
acccagcttt cttgtacaaa gttgg                                              25

<210> SEQ ID NO: 15
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 15
gttcagcttt tttgtacaaa gttgg                                              25

<210> SEQ ID NO: 16
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 16
gttcagcttt cttgtacaaa gttgg                                              25

<210> SEQ ID NO: 17
<211> LENGTH: 39
<212> TYPE: DNA
<213> ORGANISM: Unknown
<220> FEATURE:
<223> OTHER INFORMATION: Description of Unknown Organism: recombination
      products

<400> SEQUENCE: 17
ccaccacaaa cgcgtccatg gaattacact ttaatttag       39

<210> SEQ ID NO: 18
<211> LENGTH: 39
<212> TYPE: DNA
<213> ORGANISM: Unknown
<220> FEATURE:
<223> OTHER INFORMATION: Description of Unknown Organism: recombination
      products

<400> SEQUENCE: 18
ccaccacaag tcgacgcatg ccgacagcct tccaaatgt       39

<210> SEQ ID NO: 19
<211> LENGTH: 46
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 19
ggccgattac gatatcccaa cgaccgaaaa cctgtatttt cagggt       46

<210> SEQ ID NO: 20
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 20
caggttttcg gtcgttggga tatcgtaatc       30

<210> SEQ ID NO: 21
<211> LENGTH: 47
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 21
ggccagatta cgatatccca acgaccgaaa acctgtattt tcagggt       47

<210> SEQ ID NO: 22
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 22
caggttttcg gtcgttggga tatcgtaatc t       31

<210> SEQ ID NO: 23
<211> LENGTH: 48
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 23
ggccaagatt acgatatccc aacgaccgaa aacctgtatt ttcagggt       48

<210> SEQ ID NO: 24
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 24
caggttttcg gtcgttggga tatcgtaatc tt       32

<210> SEQ ID NO: 25
<211> LENGTH: 15
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 25
accgtttacg tggac       15

<210> SEQ ID NO: 26
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 26
tcgagtccac gtaaacggtt cccacttatt a       31

<210> SEQ ID NO: 27
<211> LENGTH: 39
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 27
uauuuucagg guatggagaa aaaaatcact ggatatacc       39

<210> SEQ ID NO: 28
<211> LENGTH: 33
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 28
ucccacuuau uacgccccgc cctgccactc atc       33

<210> SEQ ID NO: 29
<211> LENGTH: 33
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 29
uauuuucagg guatgcctgt tctggaaaac cgg       33

<210> SEQ ID NO: 30
<211> LENGTH: 34
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 30
ucccacuuau uatttcagcc ccagggcggc tttc                          34

<210> SEQ ID NO: 31
<211> LENGTH: 58
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 31
tccgttgaag cctgcttttt tatactaact tgagcgaagc ctcggggtca gcataagg        58

<210> SEQ ID NO: 32
<211> LENGTH: 58
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 32
ccaataactt cgtatagcat acattatacg aagttattgc cccttggtga catactcg        58

<210> SEQ ID NO: 33
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 33
tcactagtcg gcggcccaca                                          20

<210> SEQ ID NO: 34
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 34
gagcggcccc cgcggaccac                                          20

<210> SEQ ID NO: 35
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 35
ggcccacaag tttgtacaaa a                                        21

<210> SEQ ID NO: 36
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 36
ccccgcggac cactttgtac                                                    20

<210> SEQ ID NO: 37
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 37
acaagtttgt acaaaaaagc a                                                  21

<210> SEQ ID NO: 38
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 38
accactttgt acaagaaagc t                                                  21

<210> SEQ ID NO: 39
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 39
rbycwgcttt yttrtacwaa stkgd                                              25

<210> SEQ ID NO: 40
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 40
asccwgcttt yttrtacwaa stkgw                                              25

<210> SEQ ID NO: 41
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 41
asccwgcttt yttrtacwaa gttgg                                              25

<210> SEQ ID NO: 42
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 42
gttcagcttt yttrtacwaa stkgw                                              25

<210> SEQ ID NO: 43
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 43
gttcagcttt yttrtacwaa gttgg                                              25

<210> SEQ ID NO: 44
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 44
tcggacgaaa aaatatgatt gaact                                              25

<210> SEQ ID NO: 45
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 45
tcggacgaaa aaacatgttt gaaca                                              25

<210> SEQ ID NO: 46
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 46
tcggacgaaa gaacatgttt gaaca                                              25

<210> SEQ ID NO: 47
<211> LENGTH: 25
<212> TYPE: DNA
<213> ORGANISM: Unknown
<220> FEATURE:
<223> OTHER INFORMATION: Description of Unknown Organism: recombination
      products

<400> SEQUENCE: 47
tgggtcgaaa gaacatgttt cacca                                              25

<210> SEQ ID NO: 48

<210> SEQ ID NO: 48
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 48
aattctcatg tttgacagct tatc                                       24

<210> SEQ ID NO: 49
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 49
cgatggatat gttctgccaa g                                          21

<210> SEQ ID NO: 50
<211> LENGTH: 49
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 50
acaagtttgt acaaaaaagc aggctaattc tcatgtttga cagcttatc             49

<210> SEQ ID NO: 51
<211> LENGTH: 46
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 51
accactttgt acaagaaagc tgggtcgatg gatatgttct gccaag                46

<210> SEQ ID NO: 52
<211> LENGTH: 53
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 52
ggggacaagt ttgtacaaaa aagcaggcta attctcatgt ttgacagctt atc        53

<210> SEQ ID NO: 53
<211> LENGTH: 50
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 53
ggggaccact tgtacaaga aagctgggtc gatggatatg ttctgccaag             50

<210> SEQ ID NO: 54
<211> LENGTH: 23

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 54
aatacattca aatatgtatc cgc                                              23

<210> SEQ ID NO: 55
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 55
ttaccaatgc ttaatcagtg ag                                               22

<210> SEQ ID NO: 56
<211> LENGTH: 48
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 56
acaagtttgt acaaaaaagc aggctaatac attcaaatat gtatccgc                   48

<210> SEQ ID NO: 57
<211> LENGTH: 47
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 57
accactttgt acaagaaagc tgggtttacc aatgcttaat cagtgag                    47

<210> SEQ ID NO: 58
<211> LENGTH: 52
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 58
ggggacaagt ttgtacaaaa aagcaggcta atacattcaa atatgtatcc gc              52

<210> SEQ ID NO: 59
<211> LENGTH: 51
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 59
ggggaccact ttgtacaaga aagctgggtt taccaatgct taatcagtga g               51

<210> SEQ ID NO: 60
<211> LENGTH: 25
<212> TYPE: DNA
```

```
<213> ORGANISM: Unknown
<220> FEATURE:
<223> OTHER INFORMATION: Description of Unknown Organism: recombination
      products

<400> SEQUENCE: 60
agcctgcttt tttatactaa cttga                                              25
```

RECOMBINATIONAL CLONING USING NUCLEIC ACIDS HAVING RECOMBINATION SITES

CROSS-REFERENCE TO RELATED APPLICATIONS

The present application is a divisional of U.S. application Ser. No. 09/177,387, filed Oct. 23, 1998, which claims the benefit of the filing date of U.S. Provisional Application No. 60/065,930, filed Oct. 24, 1997, the disclosure of which is incorporated by reference herein in its entirety. The present application claims priority to U.S. application Ser. No. 08/663,002, filed Jun. 7, 1996, (now U.S. Pat. No. 5,888,732) and is related to U.S. application Ser. No. 08/486,139, filed Jun. 7, 1995 now abandoned, the disclosures of which applications are incorporated by reference herein in their entireties.

BACKGROUND OF THE INVENTION

1. Field of the Invention

The present invention relates to recombinant DNA technology. DNA and vectors having engineered recombination sites are provided for use in a recombinational cloning method that enables efficient and specific recombination of DNA segments using recombination proteins. The DNAs, vectors and methods are useful for a variety of DNA exchanges, such as subcloning of DNA, in vitro or in vivo.

2. Related Art

Site-specific recombinases. Site-specific recombinases are proteins that are present in many organisms (e.g. viruses and bacteria) and have been characterized to have both endonuclease and ligase properties. These recombinases (along with associated proteins in some cases) recognize specific sequences of bases in DNA and exchange the DNA segments flanking those segments. The recombinases and associated proteins are collectively referred to as "recombination proteins" (see, e.g.,, Landy, A., *Current Opinion in Biotechnology* 3:699–707 (1993)).

Numerous recombination systems from various organisms have been described. See, e.g., Hoess et al., *Nucleic Acids Research* 14(6):2287 (1986); Abremski et al., *J. Biol. Chem.* 261(1):391 (1986); Campbell, *J. Bacteriol.* 174(23):7495 (1992); Qian et al., *J. Biol. Chem.* 267(11):7794 (1992); Araki et al., *J. Mol. Biol.* 225(1):25 (1992); Maeser and Kahnmann *Mol. Gen. Genet.* 230:170–176) (1991); Esposito et al., *Nucl. Acids Res.* 25(18):3605 (1997).

Many of these belong to the integrase family of recombinases (Argos et al. *EMBO J.* 5:433–440 (1986)). Perhaps the best studied of these are the Integrase/att system from bacteriophage λ (Landy, A. *Current Opinions in Genetics and Devel.* 3:699–707 (1993)), the Cre/loxP system from bacteriophage P1 (Hoess and Abremski (1990) In *Nucleic Acids and Molecular Biology*, vol. 4. Eds.: Eckstein and Lilley, Berlin-Heidelberg: Springer-Verlag; pp. 90–109), and the FLP/FRT system from the Saccharomyces cerevisiae 2μ circle plasmid (Broach et al. *Cell* 29:227–234 (1982)).

Backman (U.S. Pat. No. 4,673,640) discloses the in vivo use of λ recombinase to recombine a protein producing DNA segment by enzymatic site-specific recombination using wild-type recombination sites attB and attP.

Hasan and Szybalski (*Gene* 56:145–151 (1987)) discloses the use of λ Int recombinase in vivo for intramolecular recombination between wild type attP and attB sites which flank a promoter. Because the orientations of these sites are inverted relative to each other, this causes an irreversible flipping of the promoter region relative to the gene of interest.

Palazzolo et al. *Gene* 88:25–36 (1990), discloses phage lambda vectors having bacteriophage λ arms that contain restriction sites positioned outside a cloned DNA sequence and between wild-type loxP sites. Infection of *E. coli* cells that express the Cre recombinase with these phage vectors results in recombination between the loxP sites and the in vivo excision of the plasmid replicon, including the cloned cDNA.

Pósfai et al. (*Nucl. Acids Res.* 22:2392–2398 (1994)) discloses a method for inserting into genomic DNA partial expression vectors having a selectable marker, flanked by two wild-type FRT recognition sequences. FLP site-specific recombinase as present in the cells is used to integrate the vectors into the genome at predetermined sites. Under conditions where the replicon is functional, this cloned genomic DNA can be amplified.

Bebee et al. (U.S. Pat. No. 5,434,066) discloses the use of site-specific recombinases such as Cre for DNA containing two loxP sites is used for in vivo recombination between the sites.

Boyd (*Nucl. Acids Res.* 21:817–821 (1993)) discloses a method to facilitate the cloning of blunt-ended DNA using conditions that encourage intermolecular ligation to a dephosphorylated vector that contains a wild-type loxP site acted upon by a Cre site-specific recombinase present in *E. coli* host cells.

Waterhouse et al. (PCT No. 93/19172 and *Nucleic Acids Res.* 21 (9):2265 (1993)) disclose an in vivo method where light and heavy chains of a particular antibody were cloned in different phage vectors between loxP and loxP 511 sites and used to transfect new *E. coli* cells. Cre, acting in the host cells on the two parental molecules (one plasmid, one phage), produced four products in equilibrium: two different cointegrates (produced by recombination at either loxP or loxP 511 sites), and two daughter molecules, one of which was the desired product.

In contrast to the other related art, Schlake & Bode (*Biochemistry* 33:12746–12751 (1994)) discloses an in vivo method to exchange expression cassettes at defined chromosomal locations, each flanked by a wild type and a spacer-mutated FRT recombination site. A double-reciprocal crossover was mediated in cultured mammalian cells by using this FLP/FRT system for site-specific recombination.

Transposases. The family of enzymes, the transposases, has also been used to transfer genetic information between replicons. Transposons are structurally variable, being described as simple or compound, but typically encode the recombinase gene flanked by DNA sequences organized in inverted orientations. Integration of transposons can be random or highly specific. Representatives such as Tn7, which are highly site-specific, have been applied to the in vivo movement of DNA segments between replicons (Lucklow et al., *J. Virol.* 67:4566–4579 (1993)).

Devine and Boeke *Nucl. Acids Res.* 22:3765–3772 (1994), discloses the construction of artificial transposons for the insertion of DNA segments, in vitro, into recipient DNA molecules. The system makes use of the integrase of yeast TY1 virus-like particles. The DNA segment of interest is cloned, using standard methods, between the ends of the transposon-like element TY1. In the presence of the TY1 integrase, the resulting element integrates randomly into a second target DNA molecule.

DNA cloning. The cloning of DNA segments currently occurs as a daily routine in many research labs and as a prerequisite step in many genetic analyses. The purpose of these clonings is various, however, two general purposes can be considered: (1) the initial cloning of DNA from large DNA or RNA segments (chromosomes, YACs, PCR fragments, mRNA, etc.), done in a relative handful of known vectors such as pUC, pGem, pBlueScript, and (2) the subcloning of these DNA segments into specialized vectors for functional analysis. A great deal of time and effort is expended both in the transfer of DNA segments from the initial cloning vectors to the more specialized vectors. This transfer is called subcloning.

The basic methods for cloning have been known for many years and have changed little during that time. A typical cloning protocol is as follows:

(1) digest the DNA of interest with one or two restriction enzymes;
(2) gel purify the DNA segment of interest when known;
(3) prepare the vector by cutting with appropriate restriction enzymes, treating with alkaline phosphatase, gel purify etc., as appropriate;
(4) ligate the DNA segment to the vector, with appropriate controls to eliminate background of uncut and self-ligated vector;
(5) introduce the resulting vector into an *E. coli* host cell;
(6) pick selected colonies and grow small cultures overnight;
(7) make DNA minipreps; and
(8) analyze the isolated plasmid on agarose gels (of ten after diagnostic restriction enzyme digestions) or by PCR.

The specialized vectors used for subcloning DNA segments are functionally diverse. These include but are not limited to: vectors for expressing genes in various organisms; for regulating gene expression; for providing tags to aid in protein purification or to allow tracking of proteins in cells; for modifying the cloned DNA segment (e.g., generating deletions); for the synthesis of probes (e.g., riboprobes); for the preparation of templates for DNA sequencing; for the identification of protein coding regions; for the fusion of various protein-coding regions; to provide large amounts of the DNA of interest, etc. It is common that a particular investigation will involve subcloning the DNA segment of interest into several different specialized vectors.

As known in the art, simple subclonings can be done in one day (e.g., the DNA segment is not large and the restriction sites are compatible with those of the subcloning vector). However, many other subclonings can take several weeks, especially those involving unknown sequences, long fragments, toxic genes, unsuitable placement of restriction sites, high backgrounds, impure enzymes, etc. Subcloning DNA fragments is thus of ten viewed as a chore to be done as few times as possible. Several methods for facilitating the cloning of DNA segments have been described, e.g., as in the following references.

Ferguson, J., et al. *Gene* 16:191 (1981), discloses a family of vectors for subcloning fragments of yeast DNA. The vectors encode kanamycin resistance. Clones of longer yeast DNA segments can be partially digested and ligated into the subcloning vectors. If the original cloning vector conveys resistance to ampicillin, no purification is necessary prior to transformation, since the selection will be for kanamycin.

Hashimoto-Gotoh, T., et al. *Gene* 41:125 (1986), discloses a subcloning vector with unique cloning sites within a streptomycin sensitivity gene; in a streptomycin-resistant host, only plasmids with inserts or deletions in the dominant sensitivity gene will survive streptomycin selection.

Accordingly, traditional subcloning methods, using restriction enzymes and ligase, are time consuming and relatively unreliable. Considerable labor is expended, and if two or more days later the desired subclone can not be found among the candidate plasmids, the entire process must then be repeated with alternative conditions attempted. Although site specific recombinases have been used to recombine DNA in vivo, the successful use of such enzymes in vitro was expected to suffer from several problems. For example, the site specificities and efficiencies were expected to differ in vitro; topologically-linked products were expected; and the topology of the DNA substrates and recombination proteins was expected to differ significantly in vitro (see, e.g., Adams et al, *J. Mol. Biol.* 226:661–73 (1992)). Reactions that could go on for many hours in vivo were expected to occur in significantly less time in vitro before the enzymes became inactive. Multiple DNA recombination products were expected in the biological host used, resulting in unsatisfactory reliability, specificity or efficiency of subcloning. Thus, in vitro recombination reactions were not expected to be sufficiently efficient to yield the desired levels of product.

Accordingly, there is a long felt need to provide an alternative subcloning system that provides advantages over the known use of restriction enzymes and ligases.

SUMMARY OF THE INVENTION

The present invention provides nucleic acids, vectors and methods for obtaining amplified, chimeric or recombinant nucleic acid molecules using recombination proteins and at least one recombination site, in vitro or in vivo. These methods are highly specific, rapid, and less labor intensive than standard cloning or subcloning techniques. The improved specificity, speed and yields of the present invention facilitates DNA or RNA cloning or subcloning, regulation or exchange useful for any related purpose.

The present invention relates to nucleic acids, vectors and methods for moving or exchanging nucleic acid segments (preferably DNA segments or fragments) using at least one recombination site and at least one recombination protein to provide chimeric DNA molecules which have the desired characteristic(s) and/or DNA segment(s). Use of the invention thus allows for cloning or subcloning such nucleic acid molecules into a variety of vectors. Generally, one or more parent nucleic acid molecules (preferably DNA molecules) are recombined to give one or more daughter molecules, at least one of which is the desired Product molecule, which is preferably a vector comprising the desired nucleic acid segment. The invention thus relates to nucleic acid molecules, vectors and methods to effect the exchange and/or to select for one or more desired products.

One embodiment of the present invention relates to a method of making chimeric molecule, which comprises
(a) combining in vitro or in vivo
(i) one or more Insert Donor molecules comprising a desired nucleic acid segment flanked by a first recombination site and a second recombination site, wherein the first and second recombination sites do not substantially recombine with each other;
(ii) one or more Vector Donor molecules comprising a third recombination site and a fourth recombination site, wherein the third and fourth recombination sites do not substantially recombine with each other; and
(iii) one or more site specific recombination proteins capable of recombining the first and third recombinational sites and/or the second and fourth recombinational sites;
thereby allowing recombination to occur, so as to produce at least one cointegrate nucleic acid molecule, at least one desired Product nucleic acid molecule which comprises said desired segment, and optionally a Byproduct nucleic acid molecule; and then, optionally, (b) selecting for the Product or Byproduct DNA molecule.

In another embodiment, the present invention relates to a method of making chimeric molecule, which comprises (a) combining in vitro or in vivo
  (i) one or more Insert Donor molecules comprising a desired nucleic acid segment flanked by two or more recombination sites wherein said recombination sites do not substantially recombine with each other;
  (ii) one or more Vector Donor molecules comprising two or more recombination sites, wherein said recombination sites do not substantially recombine with each other; and
  (iii) one or more site specific recombination proteins;
(b) incubating said combination under conditions sufficient to transfer one or more said desired segments into one or more of said Vector Donor molecules, thereby producing one or more Product molecules. The resulting Product molecules may optionally be selected or isolated away from other molecules such as cointegrate molecules, Byproduct molecules, and unreacted Vector Donor molecules or Insert Donor molecules. In a preferred aspect of the invention, the Insert Donor molecules are combined with one or more different Vector Donor molecules, thereby allowing for the production of different Product molecules in which the nucleic acid of interest is transferred into any number of different vectors in the single step.

In accordance with the invention, the above methods may be reversed to provide the original Insert Donor molecules which may then be used in combination with one or more different Vector Donor molecules to produce new Product or Byproduct molecules. Alternatively, the Product molecules produced by the method of the invention may serve as the Insert Donor molecules which may be used directly in combination with one or more different Vector Donor molecules, thereby producing new Product or Byproduct molecules. Thus, nucleic acid molecules of interest may be transferred or moved to any number of desired vectors, thereby providing an efficient means for subcloning molecules of interest.

Thus, the invention relates to combining a Product molecule with a second Vector Donor molecules to produce a second Product molecule. The second Product DNA molecule may then be utilized in combination with a third Vector Donor molecule to produce a third Product molecule. This process of the invention may be repeated any number of times to transfer or move the insert of interest into any number of different vectors. In this aspect of the invention, a combination of two or more different Vector Donor molecules may be combined with the Product molecule to produce in a single step different Product molecules in which the desired nucleic acid segment (derived from the Product DNA molecule) is transferred into any number of different vectors.

In particular, the present invention relates to a method for cloning or subcloning one or more desired nucleic acid molecules comprising (a) combining in vitro or in vivo
  (i) one or more Insert Donor molecules comprising one or more desired nucleic acid segments flanked by at least two recombination sites, wherein said recombination sites do not substantially recombined with each other;
  (ii) one or more Vector Donor molecules comprising at least two recombination sites, wherein said recombination sites do not substantially recombine with each other; and
  (iii) one or more site specific recombination proteins;
(b) incubating said combination under conditions sufficient to allow one or more of said desired segments to be transferred into one or more of said Vector Donor molecules, thereby producing one or more Product molecules;
(c) optionally selecting for or isolating said Product molecule;
(d) combining in vitro or in vivo
  (i) one or more of said Product molecules comprising said desired segments flanked by two or more recombination sites, wherein said recombination sites do not substantially recombine with each other;
  (ii) one or more different Vector Donor molecules comprising two or more recombination sites, wherein said recombination sites do not substantially recombine with each other; and
  (iii) one or more site specific recombination protein; and
(e) incubating said combination under conditions sufficient to transfer one or more of said desired segments into one or more of said different Vector Donor molecules, thereby producing one or more different Product molecules.

In accordance with the invention, Vector Donor molecules may comprise vectors which may function in a variety of systems or host cells. Preferred vectors for use in the invention include prokaryotic vectors, eukaryotic vectors or vectors which may shuttle between various prokaryotic and/or eukaryotic systems (e.g. shuttle vectors). Preferred prokaryotic vectors for use in the invention include but are not limited to vectors which may propagate and/or replicate in gram negative and/or gram positive bacteria, including bacteria of the genus Escherichia, Salmonella, Proteus, Clostridium, Klebsiella, Bacillus, Streptomyces, and Pseudomonas and preferably in the species *E. coli*. Eukaryotic vectors for use in the invention include vectors which propagate and/or replicate and yeast cells, plant cells, mammalian cells, (particularly human), fungal cells, insect cells, fish cells and the like. Particular vectors of interest include but are not limited to cloning vectors, sequencing vectors, expression vectors, fusion vectors, two-hybrid vectors, gene therapy vectors, and reverse two-hybrid vectors. Such vectors may be used in prokaryotic and/or eukaryotic systems depending on the particular vector.

The Insert Donor molecules used in accordance with the invention preferably comprise two or more recombination sites which allow the insert (e.g. the nucleic acid segment of interest) of the Donor molecules to be transferred or moved into one or more Vector Donor molecules in accordance with the invention. The Insert Donor molecules of the invention may be prepared by any number of techniques by which two or more recombination sites are added to the molecule of interest. Such means for including recombination sites to prepare the Insert Donor molecules of the invention includes mutation of a nucleic acid molecule (e.g. random or site specific mutagenesis), recombinant techniques (e.g. ligation of adapters or nucleic acid molecules comprising recombination sites to linear molecules), amplification (e.g. using primers which comprise recombination sites or portions thereof) transposition (e.g. using transposons which comprise recombination sites), recombination (e.g. using one or more homologous sequences comprising recombination sites), nucleic acid synthesis (e.g. chemical synthesis of molecules comprising recombination sites or enzymatic synthesis using various polymerases or reverse transcriptases) and the like. In accordance with the invention, nucleic acid molecules to which one or more recombination sites are added may be any nucleic acid molecule derived from any source and may include non naturally occurring nucleic acids (e.g. RNA's; see U.S. Pat. Nos. 5,539,082 and 5,482,836). Particularly preferred nucleic acid molecules are DNA molecules (single stranded or double stranded). Additionally, the nucleic acid molecules of interest for producing Insert Donor molecules may be linear or circular and further may comprise a particular sequence of interest (e.g. a gene) or may be a population of molecules (e.g. molecules generated from a genomic or cDNA libraries).

Thus, the invention relates to a number of methods for preparing Insert Donor molecules and the Insert Donor molecules produced by such methods. In one aspect of the invention, primers comprising one or more recombination sites or portions thereof are used in the nucleic acid synthesis or nucleic acid amplification to prepare the Insert Donor molecules of the invention. Thus, the invention relates to a method of synthesizing a nucleic acid molecule comprising:

(a) mixing one or more nucleic acid templates with a polypeptide having polymerase activity and one or more primers comprising one or more recombination sites or portions thereof; and (b) incubating said mixture under conditions sufficient to synthesize one or more nucleic acid molecules which are complementary to all or a portion of said templates and which comprises one or more recombination sites. In accordance with the invention, the synthesized nucleic acid molecule comprising one or more recombination sites may be used as templates under appropriate conditions to synthesize nucleic acid molecules complementary to all or a portion of the recombination site containing templates, thereby forming double stranded molecules comprising one or more recombination sites. Preferably, such second synthesis step is performed in the presence of one or more primers comprising one or more recombination sites. In yet another aspect, the synthesized double stranded molecules may be amplified using primers which may comprise one or more recombination sites.

In another aspect of the invention, one or more recombination sites may be added to nucleic acid molecules by any of a number of nucleic acid amplification techniques. In particular, such method comprises:

(a) contacting a first nucleic acid molecule with a first primer molecule which is complementary to a portion of said first nucleic acid molecule and a second nucleic acid molecule with a second primer molecule which is complementary to a portion of said second nucleic acid molecule in the presence of one or more polypeptides having polymerases activity;

(b) incubating said molecules under conditions sufficient to form a third nucleic acid molecule complementary to all or a portion of said first nucleic acid molecule and the fourth nucleic acid molecule complementary to all or a portion of said second nucleic acid molecule;

(c) denaturing said first and third and said second and fourth nucleic acid molecules; and (d) repeating steps (a) through (c) one or more times, wherein said first and/or said second primer molecules comprise one or more recombination sites or portions thereof.

In yet another aspect of the invention, a method for adding one or more recombination sites to nucleic acid molecules may comprise:

(a) contacting one or more nucleic acid molecules with one or more adapters or nucleic acid molecules which comprise one or more recombination sites or portions thereof; and (b) incubating said mixture under conditions sufficient to add one or more recombination sites to said nucleic acid molecules. Preferably, linear molecules are used for adding such adapters or molecules in accordance with the invention and such adapters or molecules are preferably added to one or more termini of such linear molecules. The linear molecules may be prepared by any technique including mechanical (e.g. sonication or shearing) or enzymatic (e.g. nucleases such as restriction endonucleases). Thus, the method of the invention may further comprise digesting the nucleic acid molecule with one or more nucleases (preferably any restriction endonucleases) and ligating one or more of the recombination site containing adapters or molecules to the molecule of interest. Ligation may be accomplished using blunt ended or stick ended molecules. Alternatively, topoisomerases may be used to introduce recombination sites in accordance with the invention. Topoisomerases cleave and rejoin nucleic acid molecules and therefore may be used in place of nucleases and ligases.

In another aspect, one or more recombination sites may be added to nucleic acid molecules by de novo synthesis. Thus, the invention relates to such a method which comprises chemically synthesizing one or more nucleic acid molecules in which recombination sites are added by adding the appropriate sequence of nucleotides during the synthesis process.

In another embodiment of the invention, one or more recombination sites may be added to nucleic acid molecules of interest by a method which comprises:

(a) contacting one or more nucleic acid molecules with one or more integration sequences which comprise one or more recombination sites or portions thereof; and (b) incubation of said mixture under conditions sufficient to incorporate said recombination site containing integration sequences into said nucleic acid molecules. In accordance with this aspect of the invention, integration sequences may comprise any nucleic acid molecules which through recombination or by integration become a part of the nucleic acid molecule of interest. Integration sequences may be introduced in accordance with this aspect of the invention by in vivo or in vitro recombination (homologous recombination or illegitimate recombination) or by in vivo or in vitro installation by using transposons, insertion sequences, integrating viruses, homing introns, or other integrating elements.

In another aspect, the invention relates to kits for carrying out the methods of the invention and more specifically relates to cloning or subcloning kits and kits for making Insert Donor molecules of the invention. Such kits may comprise a carrier or receptacle being compartmentalized to receive and hold therein any number of containers. Such containers may contain any number of components for carrying out the methods of the invention or combinations of such components. In particular, a kit of the invention may comprise one or more components (or combinations thereof) selected from the group consisting of one or more recombination proteins or recombinases, one or more Vector Donor molecules, one or more Insert Donor molecules and one or more host cells (e.g. competent cells).

Kits for making the Insert Donor molecules of the invention may comprise any or a number of components and the composition of such kits may vary depending on the specific method involved. Kits for synthesizing Insert Donor molecules by amplification may comprise one or more components (or combinations thereof) selected from the group consisting of one or more polypeptides having polymerase activity (preferably DNA polymerases and most preferably thermostable DNA polymerases), one or more nucleotides, and one or more primers comprising one or more recombination sites. Kits for inserting or adding recombination sites to nucleic acid molecules of interest may comprise one or more nucleases (preferably restriction endonucleases), one or more ligases, one or more topoisomerases one or more polymerases, and one or more nucleic acid molecules or adapters comprising one or more recombination sites. Kits for integrating recombination sites into one or more nucleic acid molecules of interest may comprise one or more components (or combinations thereof) selected from the group consisting of one or more integration sequences comprising one or more recombination sites. Such integration sequences may comprise one or more transposons, integrating viruses, homologous recombination sequences, one or more host cells and the like.

The invention also relates to compositions for carrying out the methods of the invention or compositions which are produced from carrying out the methods of the invention. In particular, such compositions may comprise one or more Insert Donor molecules, one or more Vector Donor molecules and one or more recombination proteins (or combinations thereof). In a further aspect, the compositions of the invention may comprise one or more cointegrate molecules, one or more Product molecules and one or more Byproduct molecule (or combinations thereof).

Compositions related to preparing Insert Donor molecules may vary depending on the particular method utilized in preparing the desired Insert Donor molecules. Compositions for preparing such molecules by amplification may comprise one or more polypeptides having polymerase activity, one or more primers comprising one or more recombination sites, one or more nucleotides and one or more nucleic acid molecule to be amplified (or combinations thereof). Compositions related to inserting or adding recombination sites in a desired nucleic acid molecule may comprise one or more nucleic acid molecules or adapters comprising one or more recombination sites, one or more ligases, one or more restriction endonucleases, one or more topoisomerases, and one or more nucleic acid molecules desired to contain such recombination sites (or combinations thereof). Compositions related to integration of recombination sites in a desired nucleic acid molecule may comprise one or more integration sequences comprising one or more recombination sites and one or more nucleic acid molecules desired to contain the recombination sites.

In a particularly preferred aspect of the invention, libraries (e.g. populations of genomic DNA or cDNA, or populations of nucleic acid molecules, produced by de novo synthesis such as random sequences or degenerate oligonucleotides) are utilized in accordance with the present invention. By inserting or adding recombination sites to such populations of nucleic acid molecules, a population of Insert Donor molecules are produced. By the recombination methods of the invention, the library may be easily moved into different vectors (or combinations of vectors) and thus into different host systems (prokaryotic and eukaryotic) to evaluate and analyze the library or a particular sequences or clones derived from the library. Alternatively, the vectors containing the desired molecule may be used in vitro systems such as in vitro expression systems for production of RNA and/or protein. In a particularly preferred aspect, one or more recombination sites are added to nucleic acid molecules of the library by method comprising:

(a) mixing a population of linear nucleic acid molecules with one or more adapters comprising one or more recombination sites; and (b) incubating said mixture under conditions sufficient to add one or more of said adapters to one or more termini of said linear molecules. In a preferred aspect, the population of nucleic acid molecules are double stranded DNA molecules (preferably genomic DNA or cDNA). A population of linear fragments for use in the invention may be prepared by cleaving (by mechanical or enzymatic means) the genomic or cDNA. In a preferred aspect, the adapters are added to one or more termini of the linear molecules.

In another particularly preferred aspect of the invention, cDNA libraries are used to prepare a population of Insert Donor DNA molecules of the invention. In particular, this aspect of the invention relates to a method which comprises:

(a) contacting a population of RNA, mRNA or polyA+ RNA templates with one or more polypeptides having reverse transcriptase activity and one or more primers which comprises one or more recombination sites;

(b) incubating said mixture under conditions sufficient to synthesize a first population of DNA molecules complementary to said templates, wherein said DNA molecules comprise one or more recombination sites. This aspect of the invention may further comprise incubating said synthesized DNA under conditions sufficient to make a second population of DNA molecules complementary to all or a portion of said first population of DNA molecules, thereby forming a population of double stranded DNA molecules comprising one or more recombination sites.

In a particularly preferred aspect, the Insert Donor molecules of the invention comprise at least two recombination sites and where the Insert Donor molecules are linear, such two or more recombination sites are preferably located at or near both termini of the molecules. In accordance with the invention, the use of additional recombination sites (i.e. more than two) may be used to facilitate subcloning of different inserts within the Insert Donor molecule, depending on the type and placement of such recombination sites.

Other embodiments include DNA and vectors useful in the methods of the present invention. In particular, Vector Donor molecules are provided in one embodiment, wherein DNA segments within the Vector Donor are separated either by, (i) in a circular Vector Donor, at least two recombination sites, or (ii) in a linear Vector Donor, at least one recombination site, where the recombination sites are preferably engineered to enhance specificity or efficiency of recombination. One Vector Donor embodiment comprises a first DNA segment and a second DNA segment, the first or second segment comprising a selectable marker. A second Vector Donor embodiment comprises a first DNA segment and a second DNA segment, the first or second DNA segment comprising a toxic gene. A third Vector Donor embodiment comprises a first DNA segment and a second DNA segment, the first or second DNA segment comprising an inactive fragment of at least one selectable marker, wherein the inactive fragment of the Selectable marker is capable of reconstituting a functional Selectable marker when recombined across the first or second recombination site with another inactive fragment of at least one Selectable marker.

Other preferred embodiments of the present invention will be apparent to one of ordinary skill in light of what is known in the art, in light of the following drawings and description of the invention, and in light of the claims.

DETAILED DESCRIPTION OF THE INVENTION

Figure 1:
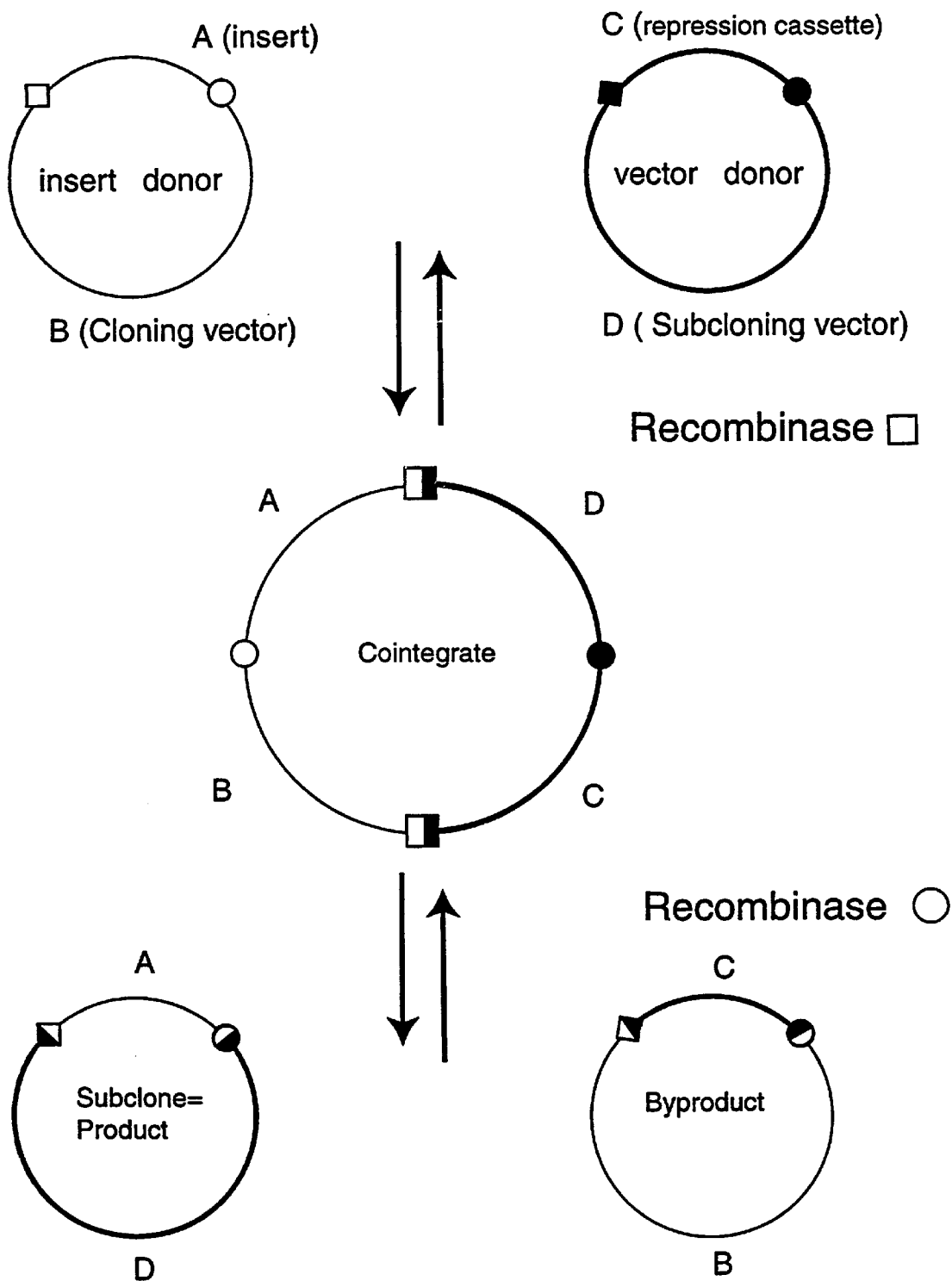
FIG. 1 depicts one general method of the present invention, wherein the starting (parent) DNA molecules can be circular or linear. The goal is to exchange the new subcloning vector D for the original cloning vector B. It is desirable in one embodiment to select for AD and against all the other molecules, including the Cointegrate. The square and circle are sites of recombination: e.g., loxP sites, att sites, etc. For example, segment D can contain expression signals, new drug markers, new origins of replication, or specialized functions for mapping or sequencing DNA.

It is unexpectedly discovered in the present invention that reversible and/or repeatable cloning and subcloning reactions can be used to manipulate nucleic acids to form chimeric nucleic acids using recombination proteins and recombination sites. Recombinational cloning according to the present invention thus uses recombination proteins with recombinant nucleic acid molecules having at least one selected recombination site for moving or exchanging segments of nucleic acid molecules, in vitro and in vivo.

These methods use recombination reactions to generate chimeric DNA or RNA molecules that have the desired characteristic(s) and/or nucleic acid segment(s). The methods of the invention provide a means in which nucleic acid molecule of interest may be moved or transferred into any number of vector systems. In accordance with the invention, such transfer to various vector systems may be accomplished separately, sequentially or in mass (e.g. into any number of different vectors in one step). The improved specificity, speed and/or yields of the present invention facilitates DNA or RNA cloning, subcloning, regulation or exchange useful for any related purpose. Such purposes include in vitro recombination of DNA or RNA segments and in vitro or in vivo insertion or modification of transcribed, replicated, isolated or genomic DNA or RNA.

Definitions

In the description that follows, a number of terms used in recombinant DNA technology are utilized extensively. In order to provide a clear and consistent understanding of the specification and claims, including the scope to be given such terms, the following definitions are provided.

Byproduct: is a daughter molecule (a new clone produced after the second recombination event during the recombinational cloning process) lacking the segment which is desired to be cloned or subcloned.

Cointegrate: is at least one recombination intermediate nucleic acid molecule of the present invention that contains both parental (starting) molecules. It will usually be circular. In some embodiments it can be linear.

Host: is any prokaryotic or eukaryotic organism that can be a recipient of the recombinational cloning Product. A "host," as the term is used herein, includes prokaryotic or eukaryotic organisms that can be genetically engineered. For examples of such hosts, see Maniatis et al., *Molecular Cloning: A Laboratory Manual*, Cold Spring Harbor Laboratory, Cold Spring Harbor, N.Y. (1982).

Insert or Inserts: include the desired nucleic acid segment or a population of nucleic acid segments (segment A of FIG. 1) which may be manipulated by the methods of the present invention. Thus, the terms Insert(s) are meant to include a particular nucleic acid (preferably DNA) segment or a population of segments. Such Insert(s) can comprise one or more genes.

Insert Donor: is one of the two parental nucleic acid molecules (e.g. RNA or DNA) of the present invention which carries the Insert. The Insert Donor molecule comprises the Insert flanked on both sides with recombination sites. The Insert Donor can be linear or circular. In one embodiment of the invention, the Insert Donor is a circular DNA molecule and further comprises a cloning vector sequence outside of the recombination signals (see FIG. 1). When a population of Inserts or population of nucleic acid segments are used to make the Insert Donor, a population of Insert Donors result and may be used in accordance with the invention.

Product: is one the desired daughter molecules comprising the A and D sequences which is produced after the second recombination event during the recombinational cloning process (see FIG. 1). The Product contains the nucleic acid which was to be cloned or subcloned. In accordance with the invention, when a population of Insert Donors are used, the resulting population of Product molecules will contain all or a portion of the population of Inserts of the Insert Donors and preferably will contain a representative population of the original molecules of the Insert Donors.

Promoter: is a DNA sequence generally described as the 5'-region of a gene, located proximal to the start codon. The transcription of an adjacent DNA segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Recognition sequence: Recognition sequences are particular sequences which a protein, chemical compound, DNA, or RNA molecule (e.g., restriction endonuclease, a modification methylase, or a recombinase) recognizes and binds. In the present invention, a recognition sequence will usually refer to a recombination site. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., *Current Opinion in Biotechnology* 5:521–527 (1994). Other examples of recognition sequences are the attB, attP, attL, and attR sequences which are recognized by the recombinase enzyme λ Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (Xis). See Landy, *Current Opinion in Biotechnology* 3:699–707 (1993). Such sites may also be engineered according to the present invention to enhance production of products in the methods of the invention. When such engineered sites lack the P1 or H1 domains to make the recombination reactions irreversible (e.g., attR or attP), such sites may be designated attR' or attP' to show that the domains of these sites have been modified in some way.

Recombinase: is an enzyme which catalyzes the exchange of DNA segments at specific recombination sites.

Recombinational Cloning: is a method described herein, whereby segments of nucleic acid molecules or populations of such molecules are exchanged, inserted, replaced, substituted, in vitro or in vivo.

Recombination proteins: include excisive or integrative proteins, enzymes, co-factors or associated proteins that are involved in recombination reactions involving one or more recombination sites. See, Landy (1994), infra.

Repression cassette: is a nucleic acid segment that contains a repressor of a Selectable marker present in the subcloning vector.

Selectable marker: is a DNA segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of Selectable markers include but are not limited to: (1) DNA segments that encode products which provide resistance against otherwise toxic compounds (e.g., antibiotics); (2) DNA segments that encode products which are otherwise lacking in the recipient cell (e.g, tRNA genes, auxotrophic markers); (3) DNA segments that encode products which suppress the activity of a gene product; (4) DNA segments that encode products which can be readily identified (e.g., phenotypic markers such as β-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1–5 above (e.g., antisense oligonucleotides); (7) DNA segments that bind products that modify a substrate (e.g. restriction endonucleases); (8) DNA segments that can be used to isolate or identify a desired molecule (e.g specific protein binding sites); (9) DNA segments that encode a specific nucleotide sequence which can be otherwise non-functional (e.g. for PCR amplification of subpopulations of molecules); (10) DNA segments, which when absent, directly or indirectly confer resistance or sensitivity to particular compounds; and/or (11) DNA segments that encode products which are toxic in recipient cells.

Selection scheme: is any method which allows selection, enrichment, or identification of a desired Product or Product (s) from a mixture containing the Insert Donor, Vector Donor, any intermediates (e.g. a Cointegrate), and/or Byproducts. The selection schemes of one preferred embodiment have at least two components that are either linked or unlinked during recombinational cloning. One component is a Selectable marker. The other component controls the expression in vitro or in vivo of the Selectable marker, or survival of the cell harboring the plasmid carrying the Selectable marker. Generally, this controlling element will be a repressor or inducer of the Selectable marker, but other means for controlling expression of the Selectable marker can be used. Whether a repressor or activator is used will depend on whether the marker is for a positive or negative selection, and the exact arrangement of the various DNA segments, as will be readily apparent to those skilled in the art. A preferred requirement is that the selection scheme results in selection of or enrichment for only one or more desired Products. As defined herein, selecting for a DNA molecule includes (a) selecting or enriching for the presence of the desired DNA molecule, and (b) selecting or enriching against the presence of DNA molecules that are not the desired DNA molecule.

In one embodiment, the selection schemes (which can be carried out in reverse) will take one of three forms, which will be discussed in terms of FIG. 1. The first, exemplified herein with a Selectable marker and a repressor therefore, selects for molecules having segment D and lacking segment C. The second selects against molecules having segment C and for molecules having segment D. Possible embodiments of the second form would have a DNA segment carrying a gene toxic to cells into which the in vitro reaction products are to be introduced. A toxic gene can be a DNA that is expressed as a toxic gene product (a toxic protein or RNA), or can be toxic in and of itself (In the latter case, the toxic gene is understood to carry its classical definition of "heritable trait".)

Examples of such toxic gene products are well known in the art, and include, but are not limited to, restriction endonucleases (e.g., DpnI), apoptosis-related genes (e.g. ASK1 or members of the bcl-2/ced-9 family), retroviral genes including those of the human immunodeficiency virus (HIV), defensins such as NP-1, inverted repeats or paired palindromic DNA sequences, bacteriophage lytic genes such as those from φX174 or bacteriophage T4; antibiotic sensitivity genes such as rpsL, antimicrobial sensitivity genes such as pheS, plasmid killer genes, eukaryotic transcriptional vector genes that produce a gene product toxic to bacteria, such as GATA-1, and genes that kill hosts in the absence of a suppressing function, e.g., kicB or ccdB. A toxic gene can alternatively be selectable in vitro, e.g., a restriction site.

Many genes coding for restriction endonucleases operably linked to inducible promoters are known, and may be used in the present invention. See, e.g. U.S. Pat. Nos. 4,960,707 (DpnI and DpnII); 5,000,333, 5,082,784 and 5,192,675 (KpnI); 5,147,800(NgoAIII and NgoAI); 5,179,015 (FspI and HaeIII); 5,200,333 (HaeII and TaqI); 5,248,605 (HpaII); 5,312,746 (ClaI); 5,231,021 and 5,304,480 (XhoI and XhoII); 5,334,526 (AluI); 5,470,740 (NsiI); 5,534,428 (SstI/SacI); 5,202,248 (NcoI); 5,139,942 (NdeI); and 5,098,839 (PacI). See also Wilson, G. G., *Nucl. Acids Res.* 19:2539–2566 (1991); and Lunnen, K. D., et al., *Gene* 74:25–32 (1988).

In the second form, segment D carries a Selectable marker. The toxic gene would eliminate transformants harboring the Vector Donor, Cointegrate, and Byproduct molecules, while the Selectable marker can be used to select for cells containing the Product and against cells harboring only the Insert Donor.

The third form selects for cells that have both segments A and D in cis on the same molecule, but not for cells that have both segments in trans on different molecules. This could be embodied by a Selectable marker that is split into two inactive fragments, one each on segments A and D.

The fragments are so arranged relative to the recombination sites that when the segments are brought together by the recombination event, they reconstitute a functional Selectable marker. For example, the recombinational event can link a promoter with a structural gene, can link two fragments of a structural gene, or can link genes that encode a heterodimeric gene product needed for survival, or can link portions of a replicon.

Site-specific recombinase: is a type of recombinase which typically has at least the following four activities (or combinations thereof): (1) recognition of one or two specific nucleic acid sequences; (2) cleavage of said sequence or sequences; (3) topoisomerase activity involved in strand exchange; and (4) ligase activity to reseal the cleaved strands of nucleic acid. See Sauer, B., *Current Opinions in Biotechnology* 5:521–527 (1994). Conservative site-specific recombination is distinguished from homologous recombination and transposition by a high degree of specificity for both partners. The strand exchange mechanism involves the cleavage and rejoining of specific DNA sequences in the absence of DNA synthesis (Landy, A. (1989) *Ann. Rev. Biochem.* 58:913–949).

Subcloning vector: is a cloning vector comprising a circular or linear nucleic acid molecule which includes preferably an appropriate replicon. In the present invention, the subcloning vector (segment D in FIG. 1) can also contain functional and/or regulatory elements that are desired to be incorporated into the final product to act upon or with the cloned DNA Insert (segment A in FIG. 1). The subcloning vector can also contain a Selectable marker (preferably DNA).

Vector: is a nucleic acid molecule (preferably DNA) that provides a useful biological or biochemical property to an Insert. Examples include plasmids, phages, autonomously replicating sequences (ARS), centromeres, and other sequences which are able to replicate or be replicated in vitro or in a host cell, or to convey a desired nucleic acid segment to a desired location within a host cell. A Vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, Selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575, entirely incorporated herein by reference), TA Cloning® brand PCR cloning (Invitrogen Corp., Carlsbad, Calif.), and the like) can also be applied to clone a fragment into a cloning vector to be used according to the present invention. The cloning vector can further contain one or more selectable markers suitable for use in the identification of cells transformed with the cloning vector.

Vector Donor: is one of the two parental nucleic acid molecules (e.g. RNA or DNA) of the present invention which carries the DNA segments comprising the DNA vector which is to become part of the desired Product. The Vector Donor comprises a subcloning vector D (or it can be called the cloning vector if the Insert Donor does not already contain a cloning vector) and a segment C flanked by recombination sites (see FIG. 1). Segments C and/or D can contain elements that contribute to selection for the desired Product daughter molecule, as described above for selection schemes. The recombination signals can be the same or different, and can be acted upon by the same or different recombinases. In addition, the Vector Donor can be linear or circular.

Primer: refers to a single stranded or double stranded oligonucleotide that is extended by covalent bonding of nucleotide monomers during amplification or polymerization of a nucleic acid molecule (e.g. a DNA molecule). In a preferred aspect, the primer comprises one or more recombination sites or portions of such recombination sites. Portions of recombination sties comprise at least 2 bases, at least 5 bases, at least 10 bases or at least 20 bases of the recombination sites of interest. When using portions of recombination sites, the missing portion of the recombination site may be provided by the newly synthesized nucleic acid molecule. Such recombination sites may be located within and/or at one or both termini of the primer. Preferably, additional sequences are added to the primer adjacent to the recombination site(s) to enhance or improve recombination and/or to stabilize the recombination site during recombination. Such stabilization sequences may be any sequences (preferably G/C rich sequences) of any length. Preferably, such sequences range in size from 1 to about 1000 bases, 1 to about 500 bases, and 1 to about 100 bases, 1 to about 60 bases, 1 to about 25, 1 to about 10, 2 to about 10 and preferably about 4 bases. Preferably, such sequences are greater than 1 base in length and preferably greater than 2 bases in length.

Template: refers to double stranded or single stranded nucleic acid molecules which are to be amplified, synthesized or sequenced. In the case of double stranded molecules, denaturation of its strands to form a first and a second strand is preferably performed before these molecules will be amplified, synthesized or sequenced, or the double stranded molecule may be used directly as a template. For single stranded templates, a primer complementary to a portion of the template is hybridized under appropriate conditions and one or more polypeptides having polymerase activity (e.g. DNA polymerases and/or reverse transcriptases) may then synthesize a nucleic acid molecule complementary to all or a portion of said template. Alternatively, for double stranded templates, one or more promoters may be used in combination with one or more polymerases to make nucleic acid molecules complementary to all or a portion of the template. The newly synthesized molecules, according to the invention, may be equal or shorter in length than the original template. Additionally, a population of nucleic acid templates may be used during synthesis or amplification to produce a population of nucleic acid molecules typically representative of the original template population.

Adapter: is an oligonucleotide or nucleic acid fragment or segment (preferably DNA) which comprises one or more recombination sites (or portions of such recombination sites) which in accordance with the invention can be added to a circular or linear Insert Donor molecule as well as other nucleic acid molecules described herein. When using portions of recombination sites, the missing portion may be provided by the Insert Donor molecule. Such adapters may be added at any location within a circular or linear molecule, although the adapters are preferably added at or near one or both termini of a linear molecule. Preferably, adapters are positioned to be located on both sides (flanking) a particularly nucleic acid molecule of interest. In accordance with the invention, adapters may be added to nucleic acid molecules of interest by standard recombinant techniques (e.g. restriction digest and ligation). For example, adapters may be added to a circular molecule by first digesting the molecule with an appropriate restriction enzyme, adding the adapter at the cleavage site and reforming the circular molecule which contains the adapter(s) at the site of cleavage. Alternatively, adapters may be ligated directly to one or more and preferably both termini of a linear molecule thereby resulting in linear molecule(s) having adapters at one or both termini. In one aspect of the invention, adapters may be added to a population of linear molecules, (e.g. a cDNA library or genomic DNA which has been cleaved or digested) to form a population of linear molecules containing adapters at one and preferably both termini of all or substantial portion of said population.

Library: refers to a collection of nucleic acid molecules (circular or linear). In one preferred embodiment, a library is representative of all or a significant portion of the DNA content of an organism (a "genomic" library), or a set of nucleic acid molecules representative of all or a significant portion of the expressed genes (a cDNA library) in a cell, tissue, organ or organism. A library may also comprise random sequences made by de novo synthesis, mutagenesis of one or more sequences and the like. Such libraries may or may not be contained in one or more vectors.

Amplification: refers to any in vitro method for increasing a number of copies of a nucleotide sequence with the use of a polymerase. Nucleic acid amplification results in the incorporation of nucleotides into a DNA and/or RNA molecule or primer thereby forming a new molecule complementary to a template. The formed nucleic acid molecule and its template can be used as templates to synthesize additional nucleic acid molecules. As used herein, one amplification reaction may consist of many rounds of replication. DNA amplification reactions include, for example, polymerase chain reaction (PCR). One PCR reaction may consist of 5–100 "cycles" of denaturation and synthesis of a DNA molecule.

Oligonucleotide: refers to a synthetic or natural molecule comprising a covalently linked sequence of nucleotides which are joined by a phosphodiester bond between the 3' position of the deoxyribose or ribose of one nucleotide and the 5' position of the deoxyribose or ribose of the adjacent nucleotide.

Nucleotide: refers to a base-sugar-phosphate combination. Nucleotides are monomeric units of a nucleic acid sequence (DNA and RNA). The term nucleotide includes ribonucleoside triphosphatase ATP, UTP, CTG, GTP and deoxyribonucleoside triphosphates such as dATP, dCTP, dITP, dUTP, dGTP, dTTP, or derivatives thereof Such derivatives include, for example, [αS]dATP, 7-deaza-dGTP and 7-deaza-dATP. The term nucleotide as used herein also refers to dideoxyribonucleosidetriphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Hybridization: Theterms "hybridization" and "hybridizing" refersto base pairing of two complementary single-stranded nucleic acid molecules (RNA and/or DNA) to give a double stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

Other terms used in the fields of recombinant DNA technology and molecular and cell biology as used herein will be generally understood by one of ordinary skill in the applicable arts.

Recombination Schemes

One general scheme for an in vitro or in vivo method of the invention is shown in FIG. 1, where the Insert Donor and the Vector Donor can be either circular or linear DNA, but is shown as circular. Vector D is exchanged for the original cloning vector B. The Insert Donor need not comprise a vector. The method of the invention allows the Inserts A to be transferred into any number of vectors. According to the invention, the Inserts may be transferred to a particular Vector or may be transferred to a number of vectors in one step. Additionally, the Inserts may be transferred to any number of vectors sequentially, for example, by using the Product DNA molecule as the Insert Donor in combination with a different Vector Donor. The nucleic acid molecule of interest may be transferred into a new vector thereby producing a new Product DNA molecule. The new Product DNA molecule may then be used as starting material to transfer the nucleic acid molecule of interest into a new vector. Such sequential transfers can be performed a number of times in any number of different vectors. Thus the invention allows for cloning or subcloning nucleic acid molecules and because of the ease and simplicity, these methods are particularly suited for high through-put applications. In accordance with the invention, it is desirable to select for the daughter molecule containing elements A and D and against other molecules, including one or more Cointegrate(s). The square and circle are different sets of recombination sites (e.g., lox sites or att sites). Segment A or D can contain at least one Selection Marker, expression signals, origins of replication, or specialized functions for detecting, selecting, expressing, mapping or sequencing DNA, where D is used in this example. This scheme can also be reversed according to the present invention, as described herein. The resulting product of the reverse reaction (e.g. the Insert Donor) may then be used in combination with one or a number of vectors to produce new product molecules in which the Inserts are contained by any number of vectors.

Examples of desired DNA segments that can be part of Element A or D include, but are not limited to, PCR products, large DNA segments, genomic clones or fragments, cDNA clones or fragments, functional elements, etc., and genes or partial genes, which encode useful nucleic acids or proteins. Moreover, the recombinational cloning of the present invention can be used to make ex vivo and in vivo gene transfer vehicles for protein expression (native or fusion proteins) and/or gene therapy.

In FIG. 1, the scheme provides the desired Product as containing A and Vector D, as follows. The Insert Donor (containing A and B) is first recombined at the square recombination sites by recombination proteins, with the Vector Donor (containing C and D), to form a Co-integrate having each of A-D-C-B. Next, recombination occurs at the circle recombination sites to form Product DNA (A and D) and Byproduct DNA (C and B). However, if desired, two or more different Co-integrates can be formed to generate two or more Products.

In one embodiment of the present in vitro or in vivo recombinational cloning method, a method for selecting at least one desired Product DNA is provided. This can be understood by consideration of the map of plasmid pEZC726 depicted in FIG. 2. The two exemplary recombination sites are attP and loxP. On one segment defined by these sites is a kanamycin resistance gene whose promoter has been replaced by the tetOP operator/promoter from transposon Tn10. In the absence of tet repressor protein, $E.$ $coli$ RNA polymerase transcribes the kanamycin resistance gene from the tetOP. If tet repressor is present, it binds to tetOP and blocks transcription of the kanamycin resistance gene. The other segment of pEZC726 has the tet repressor gene expressed by a constitutive promoter. Thus cells transformed by pEZC726 are resistant to chloramphenicol, because of the chloramphenicol acetyl transferase gene on the same segment as tetR, but are sensitive to kanamycin. The recombination reactions result in separation of the tetR gene from the regulated kanamycin resistance gene. This separation results in kanamycin resistance in cells receiving the desired recombination Product.

Two different sets of plasmids were constructed to demonstrate the in vitro method. One set, for use with Cre recombinase only (cloning vector 602 and subcloning vector 629 (FIG. 3)) contained loxP and loxP 511 sites. A second set, for use with Cre and integrase (cloning vector 705 and subcloning vector 726 (FIG. 2)) contained loxP and att sites. The efficiency of production of the desired daughter plasmid was about 60 fold higher using both enzymes than using Cre alone. Nineteen of twenty four colonies from the Cre-only reaction contained the desired product, while thirty eight of thirty eight colonies from the integrase plus Cre reaction contained the desired product plasmid.

A variety of other selection schemes can be used that are known in the art as they can suit a particular purpose for which the recombinational cloning is carried out. Depending upon individual preferences and needs, a number of different types of selection schemes can be used in the recombinational cloning or subcloning methods of the present invention. The skilled artisan can take advantage of the availability of the many DNA segments or methods for making them and the different methods of selection that are routinely used in the art. Such DNA segments include but are not limited to those which encodes an activity such as, but not limited to, production of RNA, peptide, or protein, or providing a binding site for such RNA, peptide, or protein. Examples of DNA molecules used in devising a selection scheme are given above, under the definition of "selection scheme"

Additional examples include but are not limited to:

(i) Generation of new primer sites for PCR (e.g., juxtaposition of two DNA sequences that were not previously juxtaposed);

(ii) Inclusion of a DNA sequence acted upon by a restriction endonuclease or other DNA modifying enzyme, chemical, ribozyme, etc.;

(iii) Inclusion of a DNA sequence recognized by a DNA binding protein, RNA, DNA, chemical, etc.) (e.g., for use as an affinity tag for selecting for or excluding from a population (Davis, *Nucl. Acids Res.* 24:702–706 (1996); *J. Virol.* 69: 8027–8034 (1995)) or for juxtaposing a promoter for in vitro transcription;

(iv) In vitro selection of RNA ligands for the ribosomal L22 protein associated with Epstein-Barr virus-expressed RNA by using randomized and cDNA-derived RNA libraries;

(vi) The positioning of functional elements whose activity requires a specific orientation or juxtaposition (e.g., (a) a recombination site which reacts poorly in trans, but when placed in cis, in the presence of the appropriate proteins, results in recombination that destroys certain populations of molecules; (e.g., reconstitution of a promoter sequence that allows in vitro RNA synthesis). The RNA can be used directly, or can be reverse transcribed to obtain the desired DNA construct;

(vii) Selection of the desired product by size (e.g., fractionation) or other physical property of the molecule(s); and (viii) Inclusion of a DNA sequence required for a specific modification (e.g., methylation) that allows its identification.

After formation of the Product and Byproduct in the method of the present invention, the selection step can be carried out either in vitro or in vivo depending upon the particular selection scheme which has been optionally devised in the particular recombinational cloning procedure.

For example, an in vitro method of selection can be devised for the Insert Donor and Vector Donor DNA molecules. Such scheme can involve engineering a rare restriction site in the starting circular vectors in such a way that after the recombination events the rare cutting sites end up in the Byproduct. Hence, when the restriction enzyme which binds and cuts at the rare restriction site is added to the reaction mixture in vitro, all of the DNA molecules carrying the rare cutting site, i.e., the starting DNA molecules, the Cointegrate, and the Byproduct, will be cut and rendered nonreplicable in the intended host cell. For example, cutting sites in segments B and C (see FIG. 1) can be used to select against all molecules except the Product. Alternatively, only a cutting site in C is needed if one is able to select for segment D, e.g., by a drug resistance gene not found on B.

Similarly, an in vitro selection method can be devised when dealing with linear DNA molecules. DNA sequences complementary to a PCR primer sequence can be so engineered that they are transferred, through the recombinational cloning method, only to the Product molecule. After the reactions are completed, the appropriate primers are added to the reaction solution and the sample is subjected to PCR. Hence, all or part of the Product molecule is amplified.

Other in vivo selection schemes can be used with a variety of host cells, particularly *E. coli* lines. One is to put a repressor gene on one segment of the subcloning plasmid, and a drug marker controlled by that repressor on the other segment of the same plasmid. Another is to put a killer gene on segment C of the subcloning plasmid (FIG. 1). Of course a way must exist for growing such a plasmid, i.e., there must exist circumstances under which the killer gene will not kill. There are a number of these genes known which require particular strains of *E. coli*. One such scheme is to use the restriction enzyme DpnI, which will not cleave unless its recognition sequence GATC is methylated. Many popular common *E. coli* strains methylate GATC sequences, but there are mutants in which cloned DpnI can be expressed without harm. Other restriction enzyme genes may also be used as a toxic gene for selection. In such cases, a host containing a gem encoding the corresponding methylase gene provides protected host for use in the invention. Similarly, the ccdB protein is a potent poison of DNA gyrase, efficiently trapping gyrase molecules in a cleavable complex, resulting in DNA strand breakage and cell death. Mutations in the gyrA subunit of DNA gyrase, specifically the gyrA462 mutation, confers resistance to ccdB (Bernard and Couturier, J. Mol. Bio. 226 (1992) 735–745). An *E. coli* strain, DB2, has been constructed that contains the gyrA462 mutation. DB2 cells containing plasmids that express the ccdB gene are not killed by ccdB. This strain is available from Life Technologies and has been deposited on Oct. 14, 1997 with the Collection, Agricultural Research Culture Collection (NRRL), 1815 North University Street, Peoria, Ill. 61604 USA as deposit number NRRL B-21852.

Of course analogous selection schemes can be devised for other host organisms. For example, the tet repressor/operator of Tn10 has been adapted to control gene expression in eukaryotes (Gossen, M., and Bujard, H., *Proc. Natl. Acad. Sci. USA* 89:5547–5551 (1992)). Thus the same control of drug resistance by the tet repressor exemplified herein or other selection schemes described herein can be applied to select for Product in eukaryotic cells.

Recombination Proteins

In the present invention, the exchange of DNA segments is achieved by the use of recombination proteins, including recombinases and associated co-factors and proteins. Various recombination proteins are described in the art. Examples of such recombinases include:

Cre: A protein from bacteriophage P1 (Abremski and Hoess, *J. Biol. Chem.* 259(3):1509–1514 (1984)) catalyzes the exchange (i.e., causes recombination) between 34 bp DNA sequences called loxP (locus of crossover) sites (See Hoess et al., *Nucl. Acids Res.* 14(5):2287 (1986)). Cre is available commercially (Novagen, Catalog No. 69247-1). Recombination mediated by Cre is freely reversible. From thermodynamic considerations it is not surprising that Cre-mediated integration (recombination between two molecules to form one molecule) is much less efficient than Cre-mediated excision (recombination between two loxP sites in the same molecule to form two daughter molecules). Cre works in simple buffers with either magnesium or spermidine as a cofactor, as is well known in the art. The DNA substrates can be either linear or supercoiled. A number of mutant loxP sites have been described (Hoess et al, supra). One of these, loxP 511, recombines with another loxP 511 site, but will not recombine with a loxP site.

Integrase: A protein from bacteriophage lambda that mediates the integration of the lambda genome into the *E. coli* chromosome. The bacteriophage λ Int recombinational proteins promote recombination between its substrate att sites as part of the formation or induction of a lysogenic state. Reversibility of the recombination reactions results from two independent pathways for integrative and excisive recombination. Each pathway uses a unique, but overlapping, set of the 15 protein binding sites that comprise att site DNAs. Cooperative and competitive interactions involving four proteins (Int, Xis, IHF and FIS) determine the direction of recombination.

Integrative recombination involves the Int and IHF proteins and sites attP (240 bp) and attB (25 bp). Recombination results in the formation of two new sites: atiL and attR. Excisive recombination requires Int, HF, and Xis, and sites attL and attR to generate attP and attB. Under certain conditions, FIS stimulates excisive recombination. In addition to these normal reactions, it should be appreciated that attP and attB, when placed on the same molecule, can promote excisive recombination to generate two excision products, one with attL and one with attR. Similarly, intermolecular recombination between molecules containing attL and attR, in the presence of Int, IHF and Xis, can result in integrative recombination and the generation of attP and attB. Hence, by flanking DNA segments with appropriate combinations of engineered att sites, in the presence of the appropriate recombination proteins, one can direct excisive or integrative recombination, as reverse reactions of each other.

Each of the att sites contains a 15 bp core sequence; individual sequence elements of functional significance lie within, outside, and across the boundaries of this common core (Landy, A., *Ann. Rev. Biochem.* 58:913 (1989)). Efficient recombination between the various att sites requires that the sequence of the central common region be identical between the recombining partners, however, the exact sequence is now found to be modifiable. Consequently, derivatives of the att site with changes within the core are now discovered to recombine as least as efficiently as the native core sequences.

Integrase acts to recombine the attP site on bacteriophage lambda (about 240 bp) with the attB site on the *E. coli* genome (about 25 bp) (Weisberg, R. A. and Landy, A. in *Lambda II*, p. 211 (1983), Cold Spring Harbor Laboratory)), to produce the integrated lambda genome flanked by attL (about 100 bp) and attR (about 160 bp) sites. In the absence of Xis (see below), this reaction is essentially irreversible. The integration reaction mediated by integrase and IHF works in vitro, with simple buffer containing spermidine. Integrase can be obtained as described by Nash, H. A., *Methods of Enzymology* 100:210–216 (1983). IHF can be obtained as described by Filutowicz, M., et al., *Gene* 147:149–150 (1994).

Numerous recombination systems from various organisms can also be used, based on the teaching and guidance provided herein. See, e.g., Hoess et al., *Nucleic Acids Research* 14(6):2287 (1986); Abremski et al., *J. Biol. Chem.* 261(1):391 (1986); Campbell, *J. Bacteriol.* 174(23):7495 (1992); Qian et al., *J. Biol. Chem.* 267(11):7794 (1992); Araki et al., *J. Mol. Biol.* 225(1):25 (1992)). Many of these belong to the integrase family of recombinases (Argos et al. *EMBO J.* 5:433–440 (1986)). Perhaps the best studied of these are the Integrase/att system from bacteriophage λ (Landy, A. (1993) *Current Opinions in Genetics and Devel.* 3:699–707), the Cre/loxP system from bacteriophage P1 (Hoess and Abremski (1990) In *Nucleic Acids and Molecular Biology*, vol. 4. Eds.: Eckstein and Lilley, Berlin-Heidelberg: Springer-Verlag; pp. 90–109), and the FLP/FRT system from the Saccharomyces cerevisiae 2$\mu$ circle plasmid (Broach et al. *Cell* 29:227–234 (1982)).

Members of a second family of site-specific recombinases, the resolvase family (e.g., γδ, Tn3 resolvase, Hin, Gin, and Cin) are also known. Members of this highly related family of recombinases are typically constrained to intramolecular reactions (e.g., inversions and excisions) and can require host-encoded factors. Mutants have been isolated that relieve some of the requirements for host factors (Maeser and Kahnmann (1991) *Mol. Gen. Genet.* 230:170–176), as well as some of the constraints of intramolecular recombination.

Other site-specific recombinases similar to λ Int and similar to P1 Cre can be substituted for Int and Cre. Such recombinases are known. In many cases the purification of such other recombinases has been described in the art. In cases when they are not known, cell extracts can be used or the enzymes can be partially purified using procedures described for Cre and Int.

While Cre and Int are described in detail for reasons of example, many related recombinase systems exist and their application to the described invention is also provided according to the present invention. The integrase family of site-specific recombinases can be used to provide alternative recombination proteins and recombination sites for the present invention, as site-specific recombination proteins encoded by, for example bacteriophage lambda, phi 80, P22, P2, 186, P4 and P1. This group of proteins exhibits an unexpectedly large diversity of sequences. Despite this diversity, all of the recombinases can be aligned in their C-terminal halves. A 40-residue region near the C terminus is particularly well conserved in all the proteins and is homologous to a region near the C terminus of the yeast 2 mu plasmid Flp protein. Three positions are perfectly conserved within this family: histidine, arginine and tyrosine are found at respective alignment positions 396, 399 and 433 within the well-conserved C-terminal region. These residues contribute to the active site of this family of recombinases, and suggest that tyrosine-433 forms a transient covalent linkage to DNA during strand cleavage and rejoining. See, e.g., Argos, P. et al., *EMBO J.* 5:433–40 (1986).

The recombinases of some transposons, such as those of conjugative transposons (e.g., Tn916) (Scott and Churchward. 1995. Ann Rev Microbiol 49:367; Taylor and Churchward, 1997. J Bacteriol 179:1837) belong to the integrase family of recombinases and in some cases show strong preferences for specific integration sites (Ike et al 1992. J Bacteriol 174:1801; Trieu-Cuot et al, 1993. Mol. Microbiol 8:179).

Alternatively, IS231 and other *Bacillus thuringiensis* transposable elements could be used as recombination proteins and recombination sites. *Bacillus thuringiensis* is an entomopathogenic bacterium whose toxicity is due to the presence in the sporangia of delta-endotoxin crystals active against agricultural pests and vectors of human and animal diseases. Most of the genes coding for these toxin proteins are plasmid-borne and are generally structurally associated with insertion sequences (IS231, IS232, IS240, ISBT1 and ISBT2) and transposons (Tn4430 and Tn5401). Several of these mobile elements have been shown to be active and participate in the crystal gene mobility, thereby contributing to the variation of bacterial toxicity.

Structural analysis of the iso-IS231 elements indicates that they are related to IS1151 from *Clostridium perfringens* and distantly related to IS4 and IS186 from *Escherichia coli*.

Like the other IS4 family members, they contain a conserved transposase-integrase motif found in other IS families and retroviruses. Moreover, functional data gathered from IS231A in *Escherichia coli* indicate a non-replicative mode of transposition, with a preference for specific targets. Similar results were also obtained in *Bacillus subtilis* and *B. thuringiensis*. See, e.g., Mahillon, J. et al., *Genetica* 93:13–26 (1994); Campbell, *J. Bacteriol.* 7495–7499 (1992).

An unrelated family of recombinases, the transposases, have also beenused to transfer genetic information between replicons. Transposons are structurally variable, being described as simple or compound, but typically encode the recombinase gene flanked by DNA sequences organized in inverted orientations. Integration of transposons can be random or highly specific. Representatives such as Tn7, which are highly site-specific, have been applied to the efficient movement of DNA segments between replicons (Lucklow et al. 1993. J. Virol 67:4566–4579).

A related element, the integron, are also translocatable-promoting movement of drug resistance cassettes from one replicon to another. Often these elements are defective transposon derivatives. Transposon Tn21 contains a class I integron called In2. The integrase (IntI1) from In2 is common to all integrons in this class and mediates recombination between two 59-bp elements or between a 59-bp element and an attl site that can lead to insertion into a recipient integron. The integrase also catalyzes excisive recombination. (Hall, 1997. Ciba Found Symp 207:192; Francia et al., 1997. J Bacteriol 179:4419).

Group II introns are mobile genetic elements encoding a catalytic RNA and protein. The protein component possesses reverse transcriptase, maturase and an endonuclease activity, while the RNA possesses endonuclease activity and determines the sequence of the target site into which the intron integrates. By modifying portions of the RNA sequence, the integration sites into which the element integrates can be defined. Foreign DNA sequences can be incorporated between the ends of the intron, allowing targeting to specific sites. This process, termed retrohoming, occurs via a DNA:RNA intermediate, which is copied into cDNA and ultimately into double stranded DNA (Matsuura et al., Genes and Dev 1997; Guo et al, EMBO J, 1997). Numerous intron-encoded homing endonucleases have been identified (Belfort and Roberts, 1997. NAR 25:3379). Such systems can be easily adopted for application to the described subcloning methods.

The amount of recombinase which is added to drive the recombination reaction can be determined by using known assays. Specifically, titration assay is used to determine the appropriate amount of a purified recombinase enzyme, or the appropriate amount of an extract.

Engineered Recombination Sites

The above recombinases and corresponding recombinase sites are suitable for use in recombination cloning according to the present invention. However, wild-type recombination sites may contain sequences that reduce the efficiency or specificity of recombination reactions or the function of the Product molecules as applied in methods of the present invention. For example, multiple stop codons in attB, attR, attP, attL and loxP recombination sites occur in multiple reading frames on both strands, so translation efficiencies are reduced, e.g., where the coding sequence must cross the recombination sites, (only one reading frame is available on each strand of loxP and attB sites) or impossible (in attP, attR or attL).

Accordingly, the present invention also provides engineered recombination sites that overcome these problems. For example, att sites can be engineered to have one or multiple mutations to enhance specificity or efficiency of the recombination reaction and the properties of Product DNAs (e.g., att1, att2, and att3 sites); to decrease reverse reaction (e.g., removing P1 and H1 from attR). The testing of these mutants determines which mutants yield sufficient recombinational activity to be suitable for recombination subcloning according to the present invention.

Mutations can therefore be introduced into recombination sites for enhancing site specific recombination. Such mutations include, but are not limited to: recombination sites without translation stop codons that allow fusion proteins to be encoded; recombination sites recognized by the same proteins but differing in base sequence such that they react largely or exclusively with their homologous partners allowing multiple reactions to be contemplated; and mutations that prevent hairpin formation of recombination sites. Which particular reactions take place can be specified by which particular partners are present in the reaction mixture. For example, a tripartite protein fusion could be accomplished with parental plasmids containing recombination sites attR1 and attL1; and attB3; attR1; attP3 and 10×P; and/or attR3 and 10×P; and/or attR3 and attL2.

There are well known procedures for introducing specific mutations into nucleic acid sequences. A number of these are described in Ausubel, F. M. et al., *Current Protocols in Molecular Biology*, Wiley Interscience, New York (1989–1996). Mutations can be designed into oligonucleotides, which can be used to modify existing cloned sequences, or in amplification reactions. Random mutagenesis can also be employed if appropriate selection methods are available to isolate the desired mutant DNA or RNA. The presence of the desired mutations can be confirmed by sequencing the nucleic acid by well known methods.

The following non-limiting methods can be used to modify or mutate a core region of a given recombination site to provide mutated sites that can be used in the present invention:

1. By recombination of two parental DNA sequences by site-specific (e.g. attL and attR to give attB) or other (e.g. homologous) recombination mechanisms where the parental DNA segments contain one or more base alterations resulting in the final mutated core sequence;

2. By mutation or mutagenesis (site-specific, PCR, random, spontaneous, etc) directly of the desired core sequence;

3. By mutagenesis (site-specific, PCR, random, spontaneous, etc) of parental DNA sequences, which are recombined to generate a desired core sequence;

4. By reverse transcription of an RNA encoding the desired core sequence; and

5. By de novo synthesis (chemical synthesis) of a sequence having the desired base changes.

The functionality of the mutant recombination sites can be demonstrated in ways that depend on the particular characteristic that is desired. For example, the lack of translation stop codons in a recombination site can be demonstrated by expressing the appropriate fusion proteins. Specificity of recombination between homologous partners can be demonstrated by introducing the appropriate molecules into in vitro reactions, and assaying for recombination products as described herein or known in the art. Other desired mutations in recombination sites might include the presence or absence of restriction sites, translation or transcription start signals, protein binding sites, and other known functionalities of nucleic acid base sequences. Genetic selection schemes for particular functional attributes in the recombination sites can be used according to known method steps. For example, the modification of sites to provide (from a pair of sites that do not interact) partners that do interact could be achieved by requiring deletion, via recombination between the sites, of a DNA sequence encoding a toxic substance. Similarly, selection for sites that remove translation stop sequences, the presence or absence of protein binding sites, etc., can be easily devised by those skilled in the art.

Accordingly, the present invention provides a nucleic acid molecule, comprising at least one DNA segment having at least two engineered recombination sites flanking a Selectable marker and/or a desired DNA segment, wherein at least one of said recombination sites comprises a core region having at least one engineered mutation that enhances recombination in vitro in the formation of a Cointegrate DNA or a Product DNA.

While in the preferred embodiment the recombination sites differ in sequence and do not interact with each other, it is recognized that sites comprising the same sequence can be manipulated to inhibit recombination with each other. Such conceptions are considered and incorporated herein. For example, a protein binding site can be engineered adjacent to one of the sites. In the presence of the protein that recognizes said site, the recombinase fails to access the site and the other site is therefore used preferentially. In the cointegrate this site can no longer react since it has been changed e.g. from attB to attL. In resolution of the cointegrate, the protein can be inactivated (e.g. by antibody, heat or a change of buffer) and the second site can undergo recombination.

The nucleic acid molecule can have at least one mutation that confers at least one enhancement of said recombination, said enhancement selected from the group consisting of substantially (i) favoring integration; (ii) favoring recombination; (ii) relieving the requirement for host factors; (iii) increasing the efficiency of said Cointegrate DNA or Product DNA formation; and (iv) increasing the specificity of said Cointegrate DNA or Product DNA formation.

The nucleic acid molecule preferably comprises at least one recombination site derived from attB, attP, attL or attR, such as attR' or attP'. More preferably the att site is selected from att1, att2, or att3, as described herein.

In a preferred embodiment, the core region comprises a DNA sequence selected from the group consisting of:
(a) RKYCWGCTTTYKTRTACNAASTSGB (m-att) (SEQ ID NO:1);
(b) AGCCWGCTTTYKTRTACNAACTSGB (m-attB) (SEQ ID NO:2);
(c) GTTCAGCTTTCKTRTACNAACTSGB (m-attR) (SEQ ID NO:3);
(d) AGCCWGCTTTCKTRTACNAAGTSGB (m-attL) (SEQ ID NO:4);
(e) GTTCAGCTTTYKTRTACNAAGTSGB (m-attP1) (SEQ ID NO:5);
(f) RBYCW GCTTTYTTRTACWAA STKGD (n-att) (SEQ ID NO:39);
(g) ASCCW GCTTTYTTRTACWAA STKGW (n-attB) (SEQ ID NO:40);
(h) ASCCW GCTTTYTTRTACWAA GTTGG (n-attL) (SEQ ID NO:41);
(i) GTTCA GCTTTYTTRTACWAA STKGW (n-attR) (SEQ ID NO:42);
(j) GTTCA GCTTTYTTRTACWAA GTTGG (n-attP) (SEQ ID NO:43);

or a corresponding or complementary DNA or RNA sequence, wherein R=A or G; K=G or T/U; Y=C or T/U; W=A or T/U; N=A or C or G or T/U; S=C or G; and B=C or G or T/U, as presented in 37 C.F.R. §1.822, which is entirely incorporated herein by reference, wherein the core region does not contain a stop codon in one or more reading frames.

The core region also preferably comprises a DNA sequence selected from the group consisting of:
(a) AGCCTGCTTTTTTGTACAAACTTGT (attB1) (SEQ ID NO:6);
(b) AGCCTGCTTTCTTGTACAAACTTGT (attB2) (SEQ ID NO:7);
(c) ACCCAGCTTTCTTGTACAAAGTGGT (attB3) (SEQ ID NO:8);
(d) GTTCAGCTTTTTTGTACAAACTTGT (attR1) (SEQ ID NO:9);
(e) GTTCAGCTTTCTTGTACAAACTTGT (attR2) (SEQ ID NO:10);
(f) GTTCAGCTTTCTTGTACAAAGTGGT (attR3) (SEQ ID NO:11);
(g) AGCCTGCTTTTTTGTACAAAGTTGG (attL1) (SEQ ID NO:12);
(h) AGCCTGCTTTCTTGTACAAAGTTGG (attL2) (SEQ ID NO:13);
(i) ACCCAGCTTTCTTGTACAAAGTTGG (attL3) (SEQ ID NO:14);
(j) GTTCAGCTTTTTTGTACAAAGTTGG (attP1) (SEQ ID NO:15);
(k) GTTCAGCTTTCTTGTACAAAGTTGG (attP2,P3) (SEQ ID NO:16); or a corresponding or complementary DNA or RNA sequence.

The present invention thus also provides a method for making a nucleic acid molecule, comprising providing a nucleic acid molecule having at least one engineered recombination site comprising at least one DNA sequence having at least 80–99% homology (or any range or value therein) to at least one of the above sequences, or any suitable recombination site, or which hybridizes under stringent conditions thereto, as known in the art.

Clearly, there are various types and permutations of such well-known in vitro and in vivo selection methods, each of which are not described herein for the sake of brevity. However, such variations and permutations are contemplated and considered to be the different embodiments of the present invention.

It is important to note that as a result of the preferred embodiment being in vitro recombination reactions, non-biological molecules such as PCR products can be manipulated via the present recombinational cloning method. In one example, it is possible to clone linear molecules into circular vectors.

There are a number of applications for the present invention. These uses include, but are not limited to, changing vectors, apposing promoters with genes, constructing genes for fusion proteins, changing copy number, changing replicons, cloning into phages, and cloning, e.g., PCR products (with an attB site at one end and a loxP site at the other end), genomic DNAs, and cDNAs.

Vector Donors

In accordance with the invention, any vector may be used to construct the Vector Donors of the invention. In particular, vectors known in the art and those commercially available (and variants or derivatives thereof) may in accordance with the invention be engineered to include one or more recombination sites for use in the methods of the invention. Such vectors may be obtained from, for example, Vector Laboratories Inc., InVitrogen, Promega, Novagen, NEB, Clontech, Boehringer Mannheim, Pharmacia, EpiCenter, OriGenes Technologies Inc., Stratagene, PerkinElmer, Pharmingen, Life Technologies, Inc., and Research Genetics. Such vectors may then for example be used for cloning or subcloning nucleic acid molecules of interest. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts and the like.

Other vectors of interest include viral origin vectors (M13 vectors, bacterial phage λ vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8).

Particular vectors of interest include prokaryotic expression vectors such as pcDNA II, pSL301, pSE280, pSE380, pSE420, pTrcHisA, B, and C, pRSET A, B, and C (Invitrogen, Inc.), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Life Technologies, Inc.) and variants and derivatives thereof Vector donors can also be made from eukaryotic expression vectors such as pFastBac, pFastBacHT, pFastBacDUAL, pSFV, and pTet-Splice (Life Technologies, Inc.), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBsueBacIII, pCDM8, pcDNA1, pZeoSV, pcDNA3 pREP4, pCEP4, and pEBVHis (Invitrogen, Inc.) and variants or derivatives thereof.

Other vectors of particular interest include pUC18, pUC19, pBlueScript, pSPORT, cosmids, phagemids, YAC's (yeast artificial chromosomes), BAC's (bacterial artificial chromosomes), P1 (*E. coli* phage), pQE70, pQE60, pQE9 (quagan), pBS vectors, PhageScript vectors, BlueScript vectors, pNH8A, pNH16A, pNH18A, pNH46A (Stratagene), pcDNA3 (InVitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Life Technologies, Inc.) and variants or derivatives thereof Additional vectors of interest include pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO815, pPICZ, pPICZα, pGAPZ, pGAPZα, pBlueBac4.5, pBlueBacHis2, pMelBac, pSinRep5, pSinHis, pIND, pIND(SP1), pVgRXR, pcDNA2.1. pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; λExCell, λ gt11, pTrc99A, pKK223-3, pGEX-1λT, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET-32LIC, pET-30LIC, pBAC-2cp LIC, pBACgus-2cp LIC, pT7Blue-2 LIC, pT7Blue-2, λSCREEN-1, λBlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3cp, pBACgus-2cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, pβgal-Basic, pβgal-Control, pβgal-Promoter, pβgal-Enhancer, pCMVβ, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, λgt10, λgt11, pWE15, and λTriplEx from Clontech; Lambda ZAP II, pBK-CMV, pBK-RSV, pBluescript II KS +/−, pBluescript II SK +/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS +/−, pBC KS +/−, pBC SK +/−, Phagescript, pCAL-n-EK, pCAL-n, pCAL-c, pCAL-kc, pET-3abcd, pET-11'abcd, pSPUTK, pESP-1, pCMVLacI, pOPRSVI/MCS, pOPI3 CAT,pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene.

Two-hybrid and reverse two-hybrid vectors of particular interest include pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

Polymerases

Preferred polypeptides having reverse transcriptase activity (i.e., those polypeptides able to catalyze the synthesis of a DNA molecule from an RNA template) include, but are not limited to Moloney Murine Leukemia Virus (M-MLV) reverse transcriptase, Rous Sarcoma Virus (RSV) reverse transcriptase, Avian Myeloblastosis Virus (AMV) reverse transcriptase, Rous Associated Virus (RAV) reverse transcriptase, Myeloblastosis Associated Virus (MAV) reverse transcriptase, Human Immunodeficiency Virus (HIV) reverse transcriptase, retroviral reverse transcriptase, retrotransposon reverse transcriptase, hepatitis B reverse transcriptase, cauliflower mosaic virus reverse transcriptase and bacterial reverse transcriptase. Particularly preferred are those polypeptides having reverse transcriptase activity that are also substantially reduced in RNAse H activity (i. e., "RNAse H⁻" polypeptides). By a polypeptide that is "substantially reduced in RNase H activity" is meant that the polypeptide has less than about 20%, more preferably less than about 15%, 10% or 5%, and most preferably less than about 2%, of the RNase H activity of a wildtype or RNase H⁺ enzyme such as wildtype M-MLV reverse transcriptase. The RNase H activity may be determined by a variety of assays, such as those described, for example, in U.S. Pat.

No. 5,244,797, in Kotewicz, M. L. et al., *Nucl. Acids Res.* 16:265 (1988) and in Gerard, G. F., et al., *FOCUS* 14(5):91 (1992), the disclosures of all of which are fully incorporated herein by reference. Suitable RNAse H⁻ polypeptides for use in the present invention include, but are not limited to, M-MLV H⁻ reverse transcriptase, RSV H⁻ reverse transcriptase, AMV H⁻ reverse transcriptase, RAV H⁻ reverse transcriptase, MAV H⁻ reverse transcriptase, HIV H⁻ reverse transcriptase, and SUPERSCRIPT™ I reverse transcriptase and SUPERSCRIPT™ II reverse transcriptase which are available commercially, for example from Life Technologies, Inc. (Rockville, Md.).

Other polypeptides having nucleic acid polymerase activity suitable for use in the present methods include thermophilic DNA polymerases such as DNA polymerase I, DNA polymerase III, Kienow fragment, T7 polymerase, and T5 polymerase, and thermostable DNA polymerases including, but not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT®) DNA polymerase, *Pyrococcus furiosus* (Pfu or DEEPVENT®) DNA polymerase, *Pyrococcus woosii* (Pwo) DNA polymerase, *Bacillus sterothermophilus* (Bst) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME®) DNA polymerase, *Methanobacterium thermoautotrophicum* (Mth) DNA polymerase, and mutants, variants and derivatives thereof.

It will be understood by one of ordinary skill in the relevant arts that other suitable modifications and adaptations to the methods and applications described herein are readily apparent and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

The present recombinational cloning method accomplishes the exchange of nucleic acid segments to render something useful to the user, such as a change of cloning vectors. These segments must be flanked on both sides by recombination signals that are in the proper orientation with respect to one another. In the examples below the two parental nucleic acid molecules (e.g., plasmids) are called the Insert Donor and the Vector Donor. The Insert Donor contains a segment that will become joined to a new vector contributed by the Vector Donor. The recombination intermediate(s) that contain(s) both starting molecules is called the Cointegrate(s). The second recombination event produces two daughter molecules, called the Product (the desired new clone) and the Byproduct.

Buffers

Various known buffers can be used in the reactions of the present invention. For restriction enzymes, it is advisable to use the buffers recommended by the manufacturer. Alternative buffers can be readily found in the literature or can be devised by those of ordinary skill in the art.

Examples 1–3. One exemplary buffer for lambda integrase is comprised of 50 mM Tris-HCl, at pH 7.5–7.8, 70 mM KCl, 5 mM spermidine, 0.5 mM EDTA, and 0.25 mg/ml bovine serum albumin, and, optionally, 10% glycerol.

One preferred buffer for P1 Cre recombinase is comprised of 50 mM Tris-HCl at pH 7.5, 33 mM NaCl, 5 mM spermidine, and 0.5 mg/ml bovine serum albumin.

The buffer for other site-specific recombinases which are similar to lambda Int and P1 Cre are either known in the art or can be determined empirically by the skilled artisans, particularly in light of the above-described buffers.

Example 1

Recombinational Cloning Using Cre and Cre & Int

Two pairs of plasmids were constructed to do the in vitro recombinational cloning method in two different ways. One pair, pEZC705 and pEZC726 (FIG. 2A), was constructed with loxP and att sites, to be used with Cre and λ integrase. The other pair, pEZC602 and pEZC629 (FIG. 3A), contained the loxP (wild type) site for Cre, and a second mutant lox site, loxP 511, which differs from loxP in one base (out of 34 total). The minimum requirement for recombinational cloning of the present invention is two recombination sites in each plasmid, in general X and Y, and X' and Y' Recombinational cloning takes place if either or both types of site can recombine to form a Cointegrate (e.g. X and X'), and if either or both can recombine to excise the Product and Byproduct plasmids from the Cointegrate (e.g. Y and Y'). It is important that the recombination sites on the same plasmid do not recombine. It was found that the present recombinational cloning could be done with Cre alone.

Cre-Only

Two plasmids were constructed to demonstrate this conception (see FIG. 3A). pEZC629 was the Vector Donor plasmid. It contained a constitutive drug marker (chloramphenicol resistance), an origin of replication, loxP and loxP 511 sites, a conditional drug marker (kanamycin resistance whose expression is controlled by the operator/promoter of the tetracycline resistance operon of transposon Tn10), and a constitutively expressed gene for the tet repressor protein, tetR. *E. coli* cells containing pEZC629 were resistant to chloramphenicol at 30 μg/ml, but sensitive to kanamycin at 100 μg/ml. pEZC602 was the Insert Donor plasmid, which contained a different drug marker (ampicillin resistance), an origin, and loxP and loxP 511 sites flanking a multiple cloning site.

This experiment was comprised of two parts as follows:

Part I: About 75 ng each of pEZC602 and pEZC629 were mixed in a total volume of 30 μl of Cre buffer (50 mM Tris-HCl pH 7.5, 33 mM NaCl, 5 mM spermidine-HCl, 500 μg/ml bovine serum albumin). Two 10 μl aliquots were transferred to new tubes. One tube received 0.5 μl of Cre protein (approx. 4 units per μl; partially purified according to Abremski and Hoess, *J. Biol. Chem.* 259:1509 (1984)). Both tubes were incubated at 37° C. for 30 minutes, then 70° C. for 10 minutes. Aliquots of each reaction were diluted and transformed into DH5α. Following expression, aliquots were plated on 30 μg/ml chloramphenicol; 100 μg/ml ampicillin plus 200 μg/ml methicillin; or 100 μg/ml kanamycin. Results: See Table 1. The reaction without Cre gave 1.11× 10⁶ ampicillin resistant colonies (from the Insert Donor plasmid pEZC602); 7.8×10⁵ chloramphenicol resistant colonies (from the Vector Donor plasmid pEZC629); and 140 kanamycin resistant colonies (background). The reaction with added Cre gave 7.5×10⁵ ampicillin resistant colonies (from the Insert Donor plasmid pEZC602); 6.1×10⁵ chloramphenicol resistant colonies (from the Vector Donor plasmid pEZC629); and 760 kanamycin resistant colonies (mixture of background colonies and colonies from the recombinational cloning Product plasmid). Analysis: Because the number of colonies on the kanamycin plates was much higher in the presence of Cre, many or most of them were predicted to contain the desired Product plasmid.

TABLE 1

| Enzyme | Ampicillin | Chloramphenicol | Kana-mycin | Efficiency |
|---|---|---|---|---|
| None | $1.1 \times 10^6$ | $7.8 \times 10^5$ | 140 | $140/7.8 \times 10^5 = 0.02\%$ |
| Cre | $7.5 \times 10^5$ | $6.1 \times 10^5$ | 760 | $760/6.1 \times 10^5 = 0.12\%$ |

Part II: Twenty four colonies from the "+Cre" kanamycin plates were picked and inoculated into medium containing 100 µg/ml kanamycin. Minipreps were done, and the miniprep DNAs, uncut or cut with SmaI or HindIII, were electrophoresed. Results: 19 of the 24 minipreps showed supercoiled plasmid of the size predicted for the Product plasmid. All 19 showed the predicted SmaI and HindIII restriction fragments. Analysis: The Cre only scheme was demonstrated. Specifically, it was determined to have yielded about 70% (19 of 24) Product clones. The efficiency was about 0.1% (760 kanamycin resistant clones resulted from $6.1 \times 10^5$ chloramphenicol resistant colonies).

Cre Plus Integrase

Figure 2A:
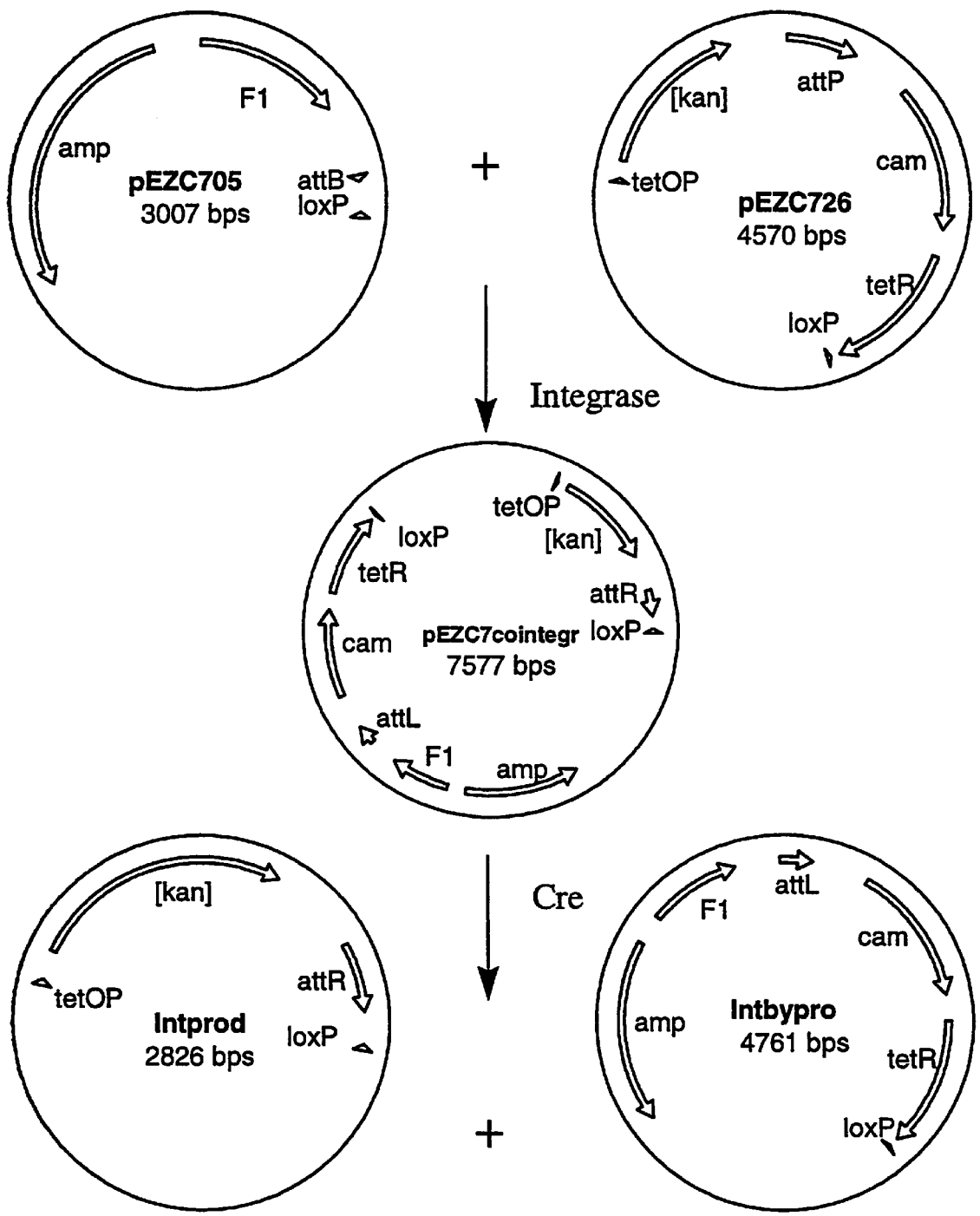
FIG. 2A depicts an in vitro method of recombining an Insert Donor plasmid (here, pEZC705) with a Vector Donor plasmid (here, pEZC726), and obtaining Product DNA and Byproduct daughter molecules. The two recombination sites are attP and loxP on the Vector Donor. On one segment defined by these sites is a kanamycin resistance gene whose promoter has been replaced by the tetOP operator/promoter from transposon Tn10. See, e.g., Sizemore et al., *Nucl. Acids Res.* 18(10):2875 (1990). In the absence of tet repressor protein, *E. coli* RNA polymerase transcribes the kanamycin resistance gene from the tetOP. If tet repressor is present, it binds to tetOP and blocks transcription of the kanamycin resistance gene. The other segment of pEZC726 has the tet repressor gene expressed by a constitutive promoter. Thus cells transformed by pEZC726 are resistant to chloramphenicol, because of the chloramphenicol acetyl transferase gene on the same segment as tetR, but are sensitive to kanamycin. The recombinase-mediated reactions result in separation of the tetR gene from the regulated kanamycin resistance gene. This separation results in kanamycin resistance only in cells receiving the desired recombination product. The first recombination reaction is driven by the addition of the recombinase called Integrase. The second recombination reaction is driven by adding the recombinase Cre to the Cointegrate (here, pEZC7 Cointegr).
Figure 2B:
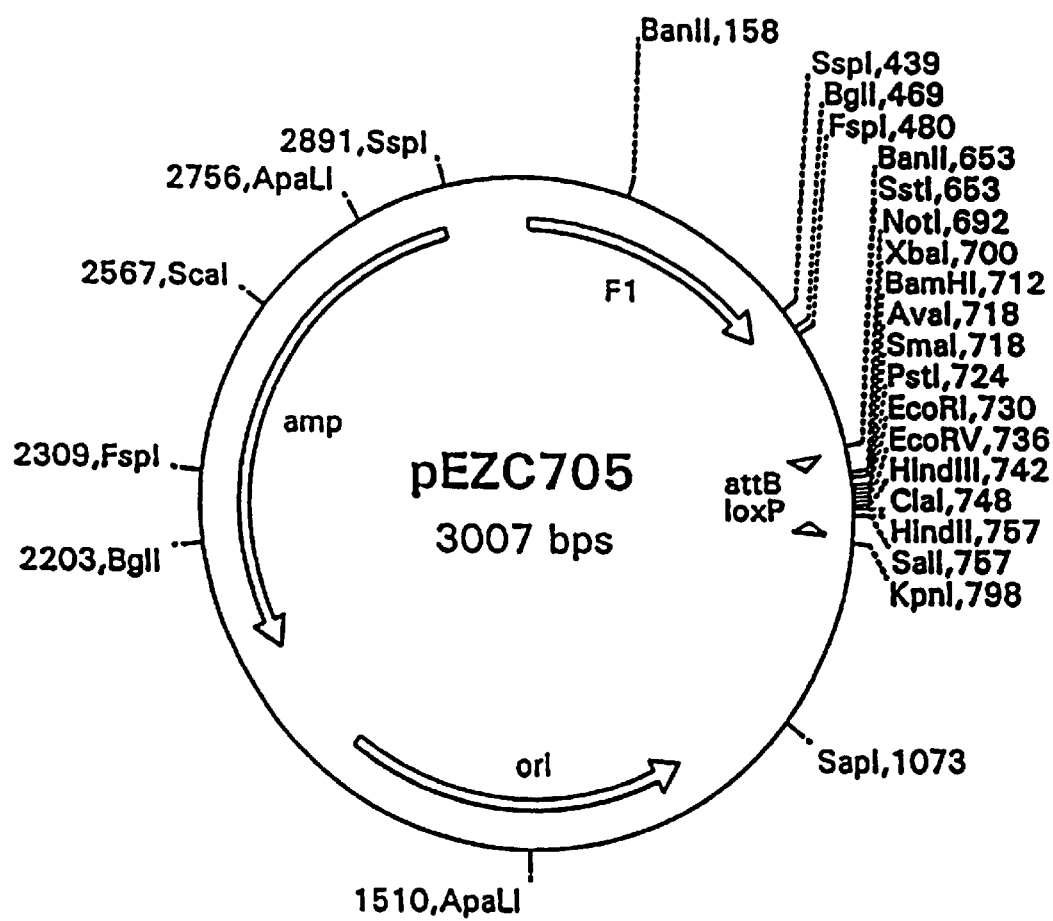
FIG. 2B depicts a restriction map of pEZC705.
Figure 2C:
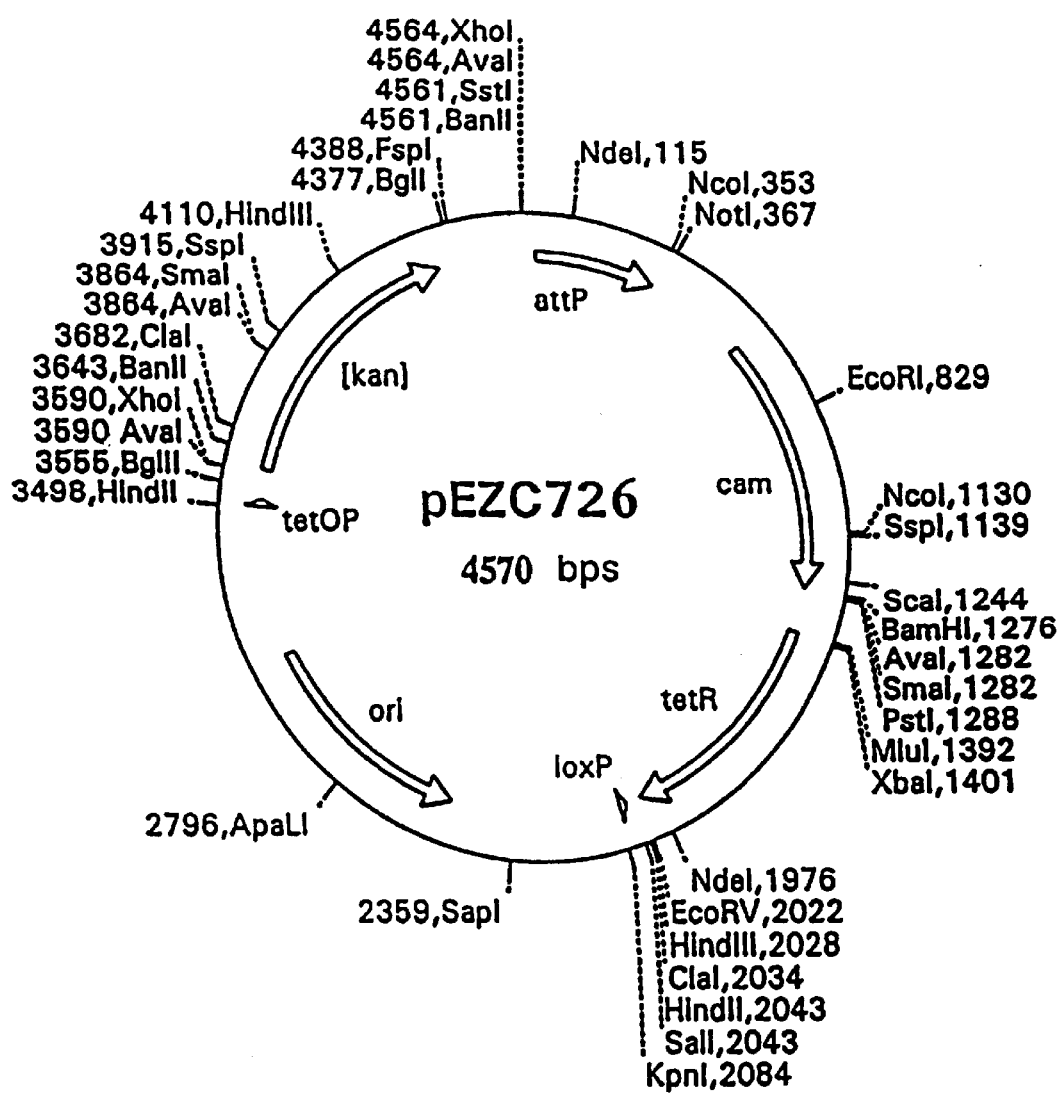
FIG. 2C depicts a restriction map of pEZC726.
Figure 2D:
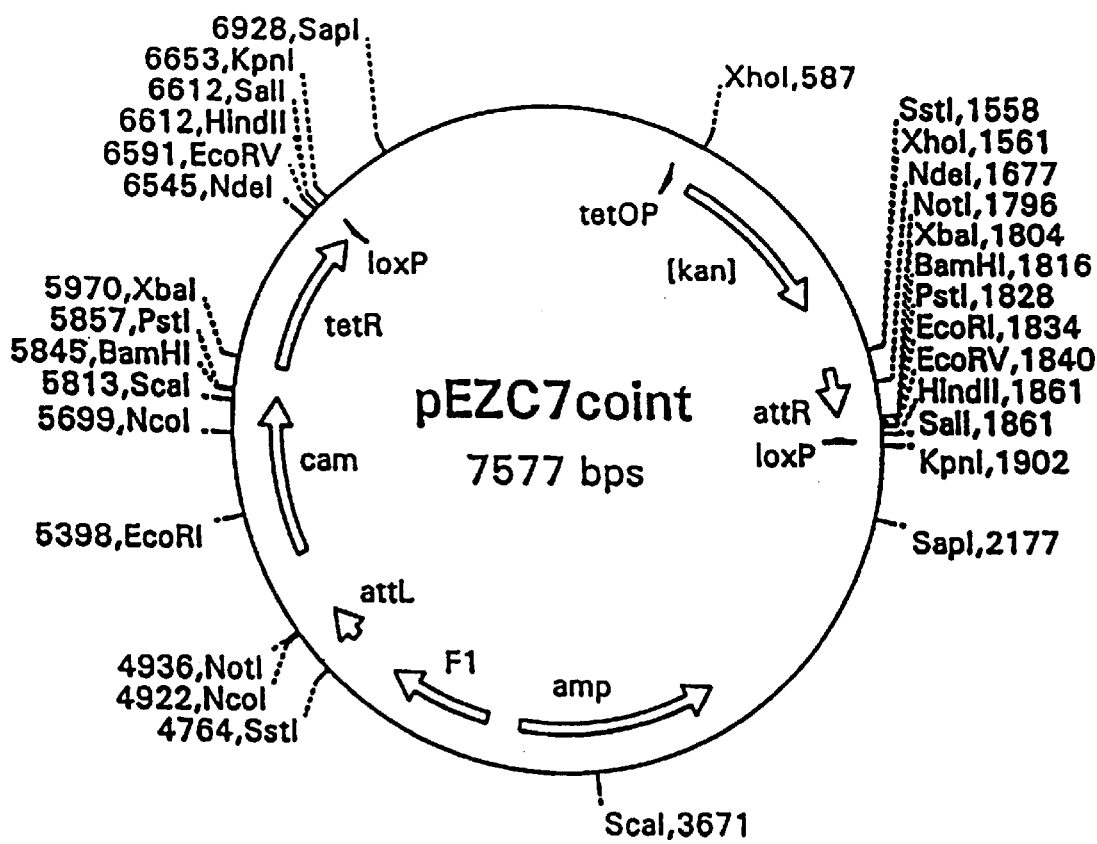
FIG. 2D depicts a restriction map of pEZC7 Coint.
Figure 2E:
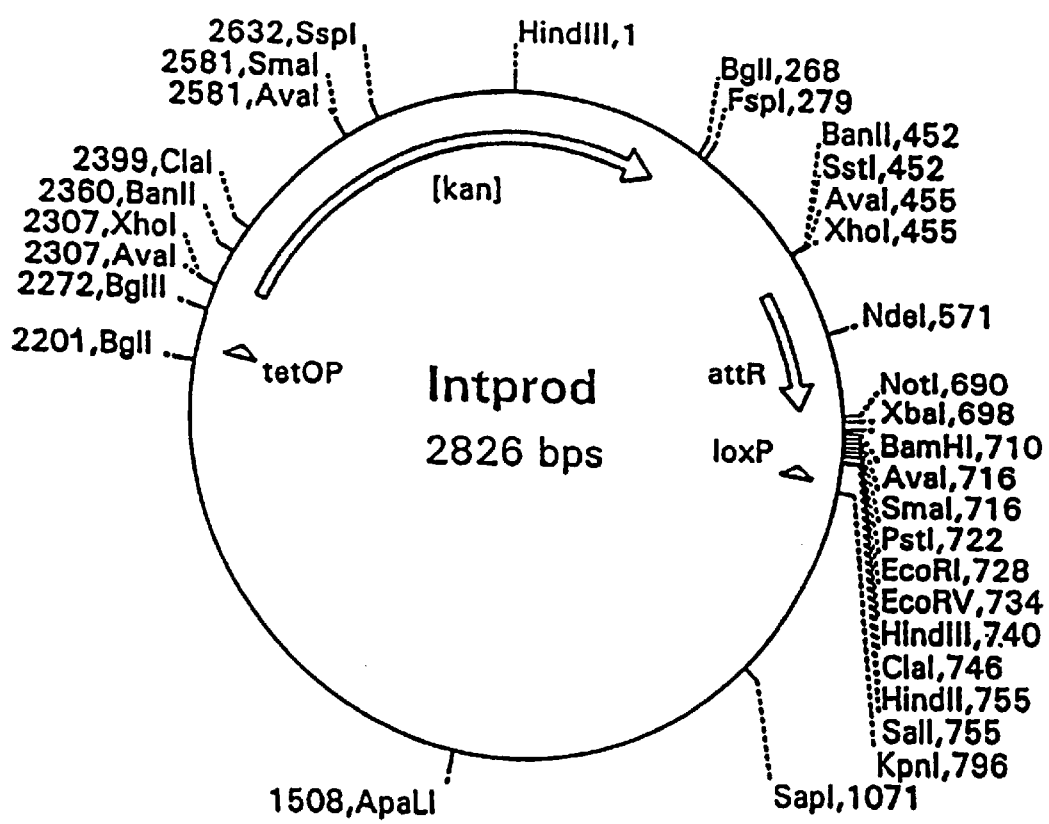
FIG. 2E depicts a restriction map of Intprod.
Figure 2F:
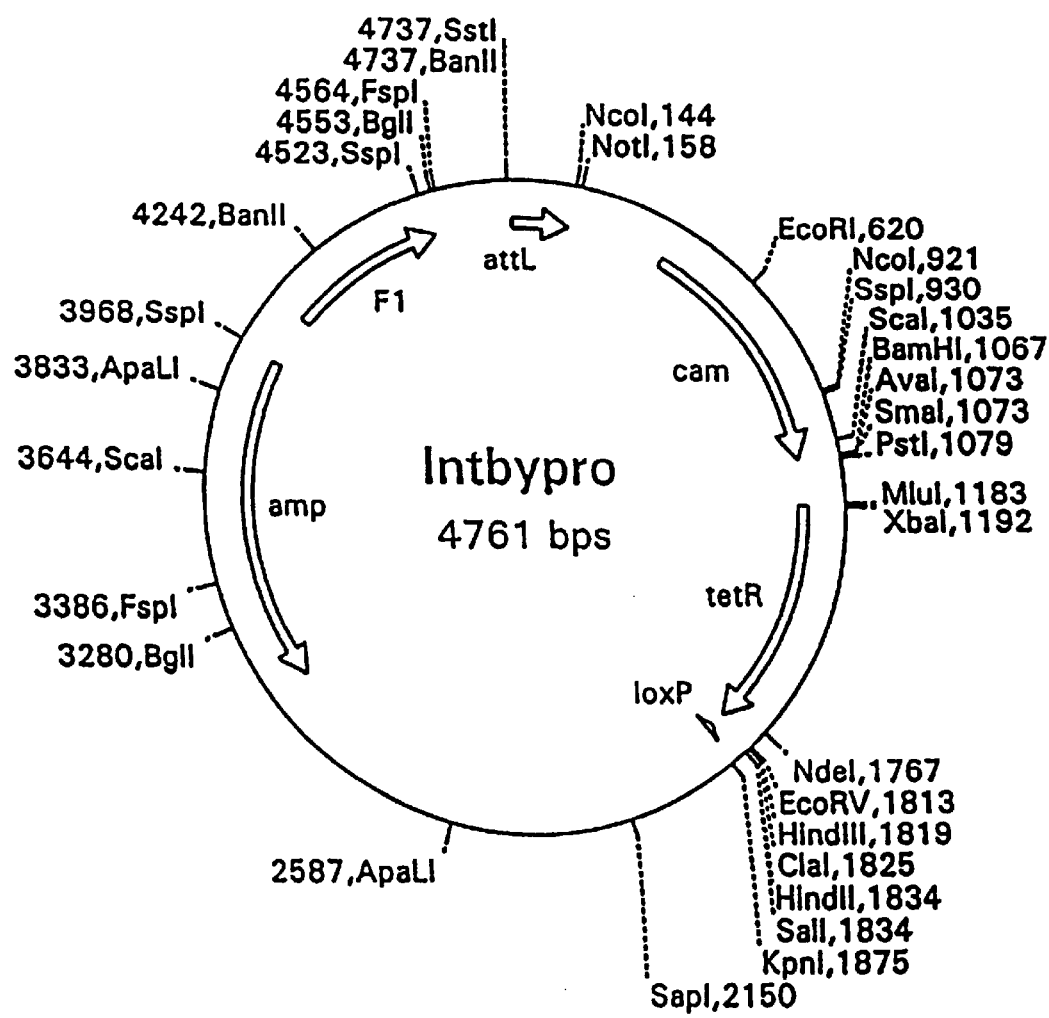
FIG. 2F depicts a restriction map of Intbypro.
Figure 3A:
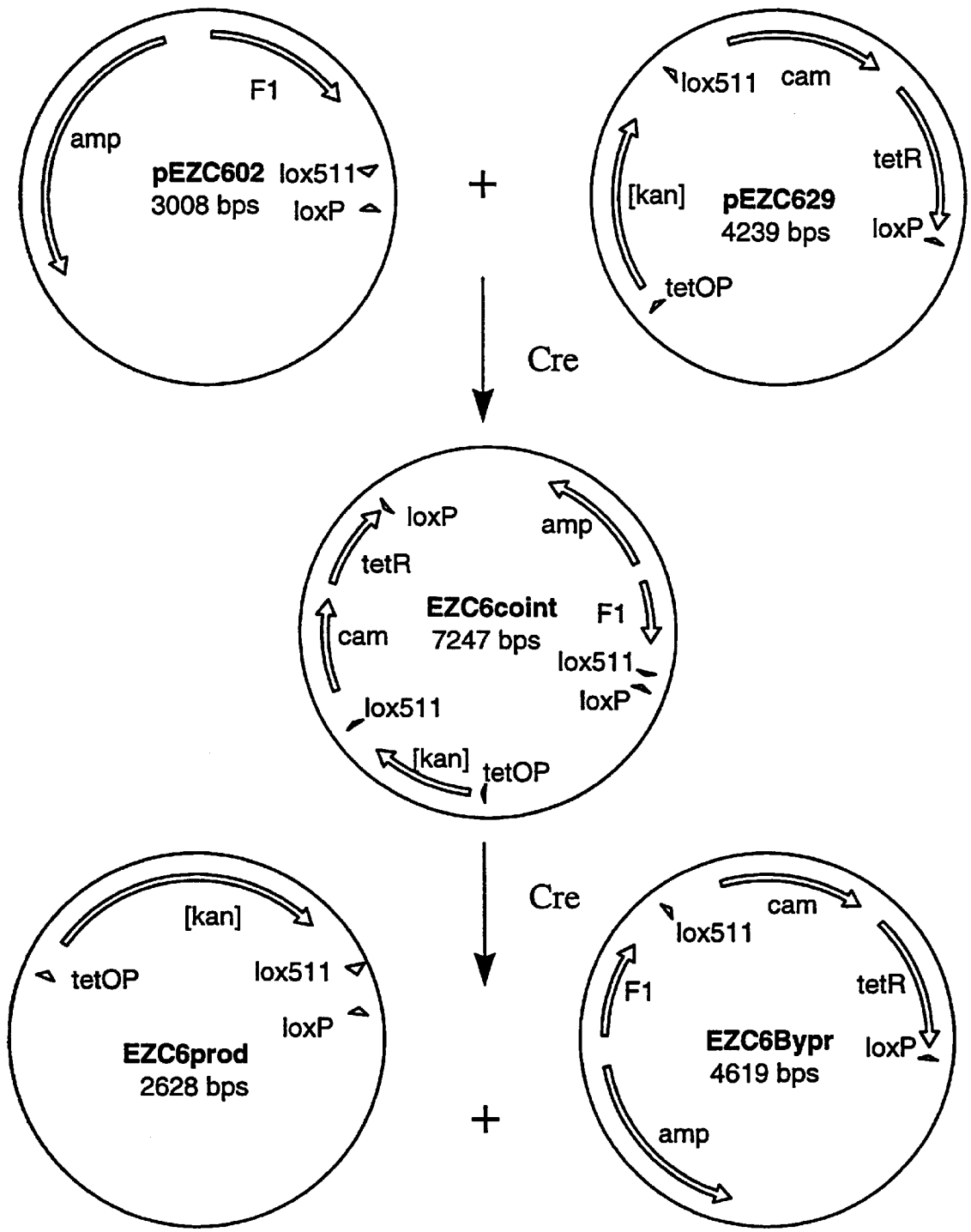
FIG. 3A depicts an in vitro method of recombining an Insert Donor plasmid (here, pEZC602) with a Vector Donor plasmid (here, pEZC629), and obtaining Product (here, EZC6prod) and Byproduct (here, EZC6Bypr) daughter molecules. The two recombination sites are loxP and loxP 511. One segment of pEZC629 defined by these sites is a kanamycin resistance gene whose promoter has been replaced by the tetOP operator/promoter from transposon Tnl0. In the absence of tet repressor protein, *E. coli* RNA polymerase transcribes the kanamycin resistance gene from the tetOP. If tet repressor is present, it binds to tetOP and blocks transcription of the kanamycin resistance gene. The other segment of pEZC629 has the tet repressor gene expressed by a constitutive promoter. Thus cells transformed by pEZC629 are resistant to chloramphenicol, because of the chloramphenicol acetyl transferase gene on the same segment as tetR, but are sensitive to kanamycin. The reactions result in separation of the tetR gene from the regulated kanamycin resistance gene. This separation results in kanamycin resistance in cells receiving the desired recombination product. The first and the second recombination events are driven by the addition of the same recombinase, Cre.
Figure 3B:
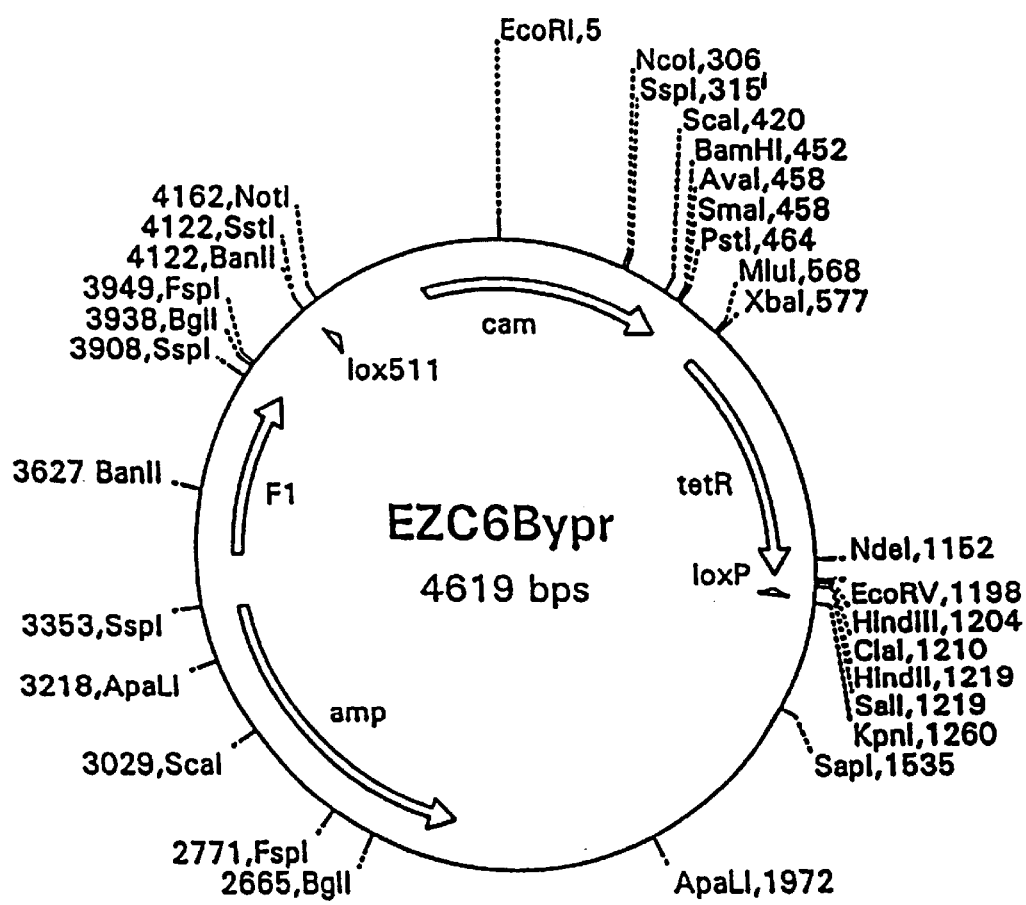
FIG. 3B depicts a restriction map of EZC6Bypr.
Figure 3C:
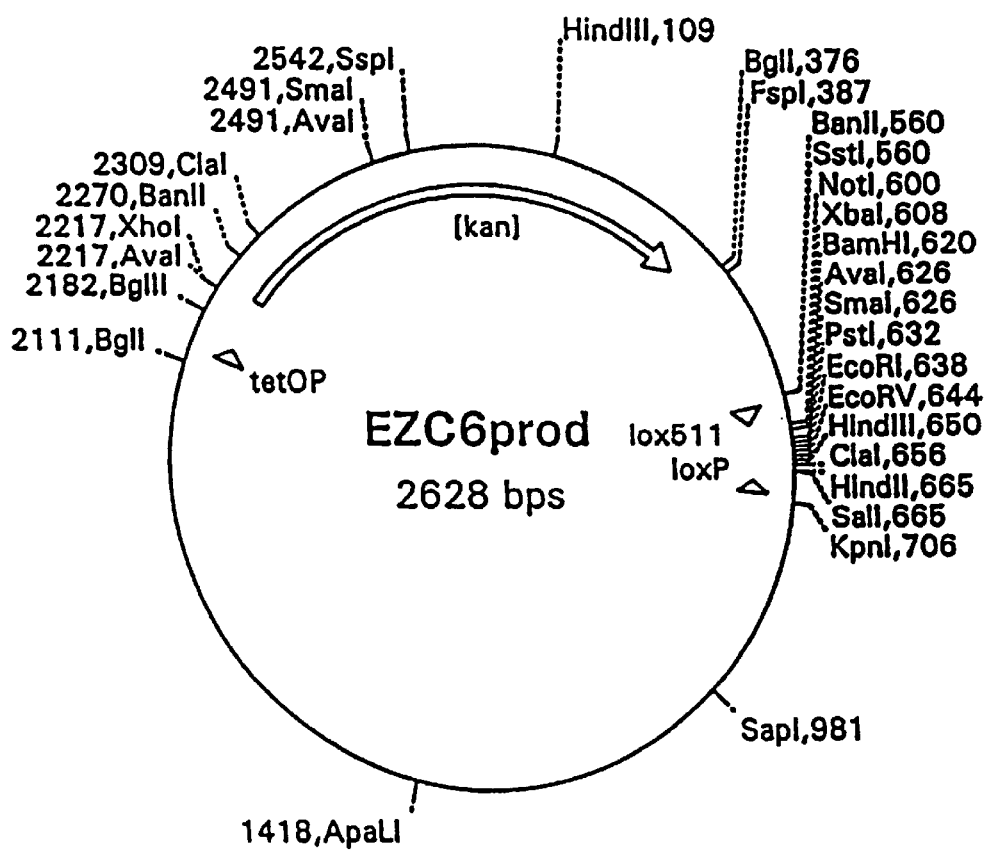
FIG. 3C depicts a restriction map of EZC6prod.
Figure 3D:
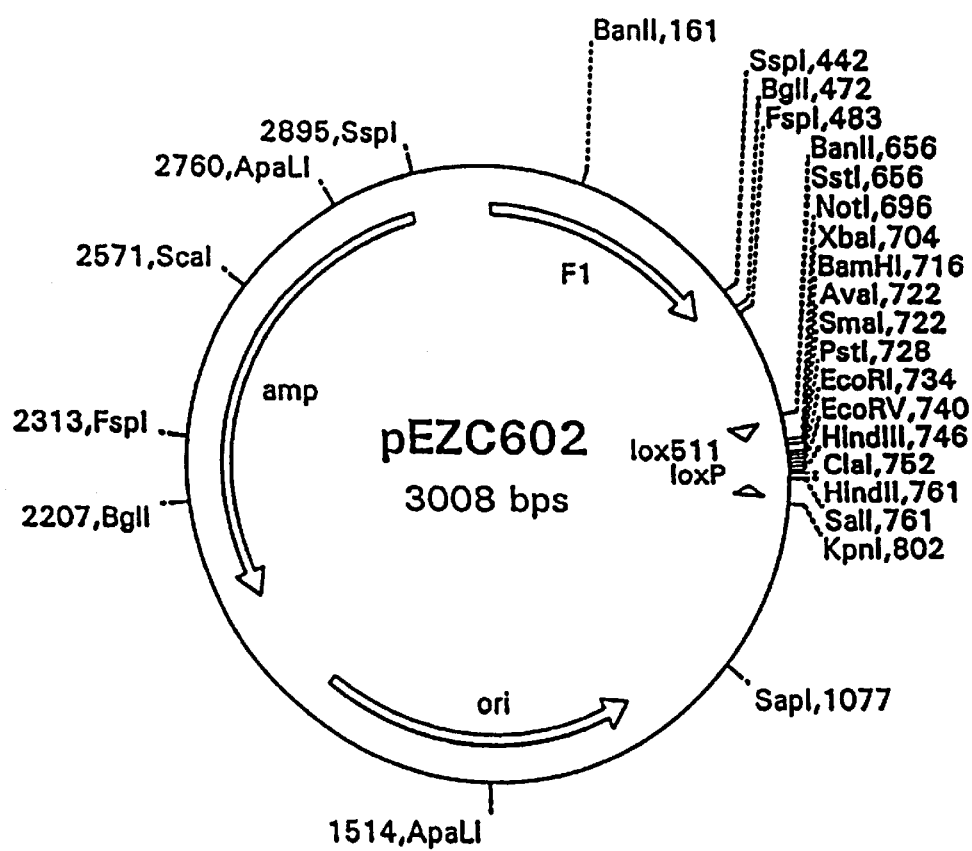
FIG. 3D depicts a restriction map of pEZC602.
Figure 3E:
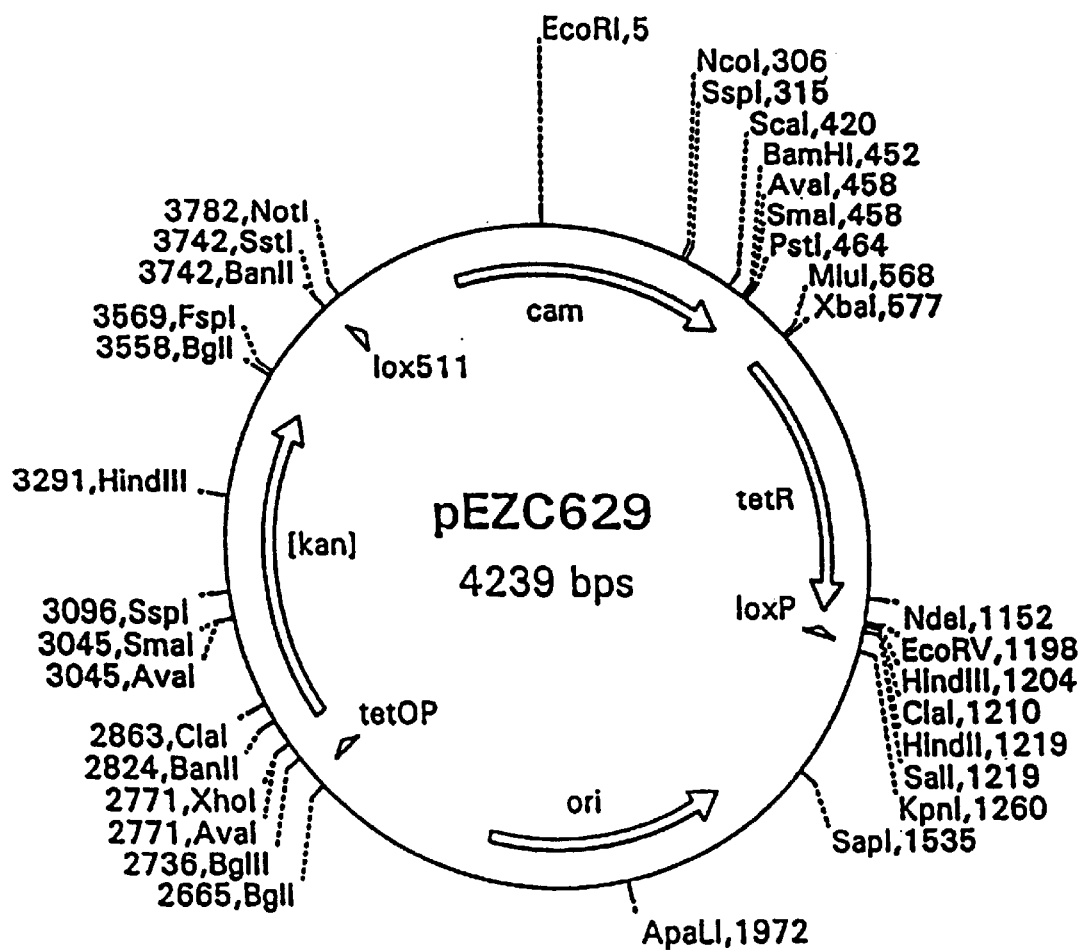
FIG. 3E depicts a restriction map of pEZC629.
Figure 3F:
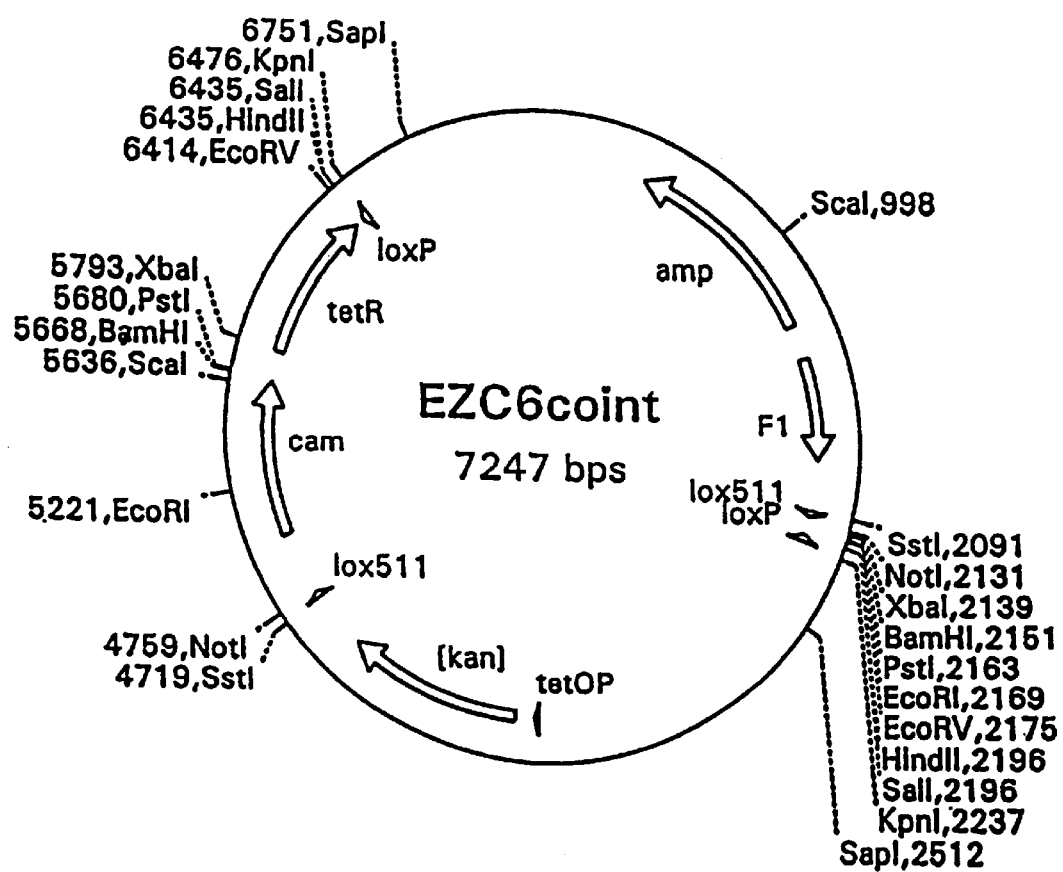
FIG. 3F depicts a restriction map of EZC6coint.

The plasmids used to demonstrate this method are exactly analogous to those used above, except that pEZC726, the Vector Donor plasmid, contained an attP site in place of loxP 511, and pEZC705, the Insert Donor plasmid, contained an attB site in place of loxP 511 (FIG. 2A).

This experiment was comprised of three parts as follows:

Part I: About 500 ng of pEZC705 (the Insert Donor plasmid) was cut with ScaI, which linearized the plasmid within the ampicillin resistance gene. (This was done because the λ integrase reaction has been historically done with the attB plasmid in a linear state (H. Nash, personal communication). However, it was found later that the integrase reaction proceeds well with both plasmids supercoiled.) Then, the linear plasmid was ethanol precipitated and dissolved in 20 µl of λ integrase buffer (50 mM Tris-HCl, about pH 7.8, 70 mM KCl, 5 mM spermidine-HCl, 0.5 mM EDTA, 250 µg/ml bovine serum albumin). Also, about 500 ng of the Vector Donor plasmid pEZC726 was ethanol precipitated and dissolved in 20 µl λ integrase buffer. Just before use, λ integrase (2 µl, 393 µg/ml) was thawed and diluted by adding 18 µl cold λ integrase buffer. One µl IHF (integration host factor, 2.4 mg/ml, an accessory protein) was diluted into 150 µl cold λ integrase buffer. Aliquots (2 µl) of each DNA were mixed with λ integrase buffer, with or without 1 µl each λ integrase and IHF, in a total of 10 µl. The mixture was incubated at 25° C. for 45 minutes, then at 70° C. for 10 minutes. Half of each reaction was applied to an agarose gel. Results: In the presence of integrase and IHF, about 5% of the total DNA was converted to a linear Cointegrate form. Analysis: Activity of integrase and IHF was confirmed.

Part II: Three microliters of each reaction (i.e., with or without integrase and IHF) were diluted into 27 µl of Cre buffer (above), then each reaction was split into two 10 µl aliquots (four altogether). To two of these reactions, 0.5 µl of Cre protein (above) were added, and all reactions were incubated at 37° C. for 30 minutes, then at 70° C. for 10 minutes. TE buffer (90 µl; TE: 10 mM Tris-HCl, pH 7.5, 1 mM EDTA) was added to each reaction, and 1 µl each was transformed into E. coli DH5α. The transformation mixtures were plated on 100 µg/ml ampicillin plus 200 µg/ml methicillin; 30 µg/ml chloramphenicol; or 100 µg/ml kanamycin.

Results: See Table 2.

TABLE 2

| Enzyme | Ampicillin | Chloramphenicol | Kana-mycin | Efficiency |
|---|---|---|---|---|
| None | 990 | 20000 | 4 | $4/2 \times 10^4 = 0.02\%$ |
| Cre only | 280 | 3640 | 0 | 0 |
| Integrase * only | 1040 | 27000 | 9 | $9/2.7 \times 10^4 = 0.03\%$ |
| Integrase * + Cre | 110 | 1110 | 76 | $76/1.1 \times 10^3 = 6.9\%$ |

* Integrase reactions also contained IHF.

Analysis: The Cre protein impaired transformation. When adjusted for this effect, the number of kanamycin resistant colonies, compared to the control reactions, increased more than 100 fold when both Cre and Integrase were used. This suggests a specificity of greater than 99%.

Part III: 38 colonies were picked from the Integrase plus Cre plates, miniprep DNAs were made and cut with HindIII to give diagnostic mapping information. Result: All 38 had precisely the expected fragment sizes. Analysis: The Cre plus λ integrase method was observed to have much higher specificity than Cre-alone. Conclusion: The Cre plus λ integrase method was demonstrated. Efficiency and specificity were much higher than for Cre only.

Example 2

Figure 4A:
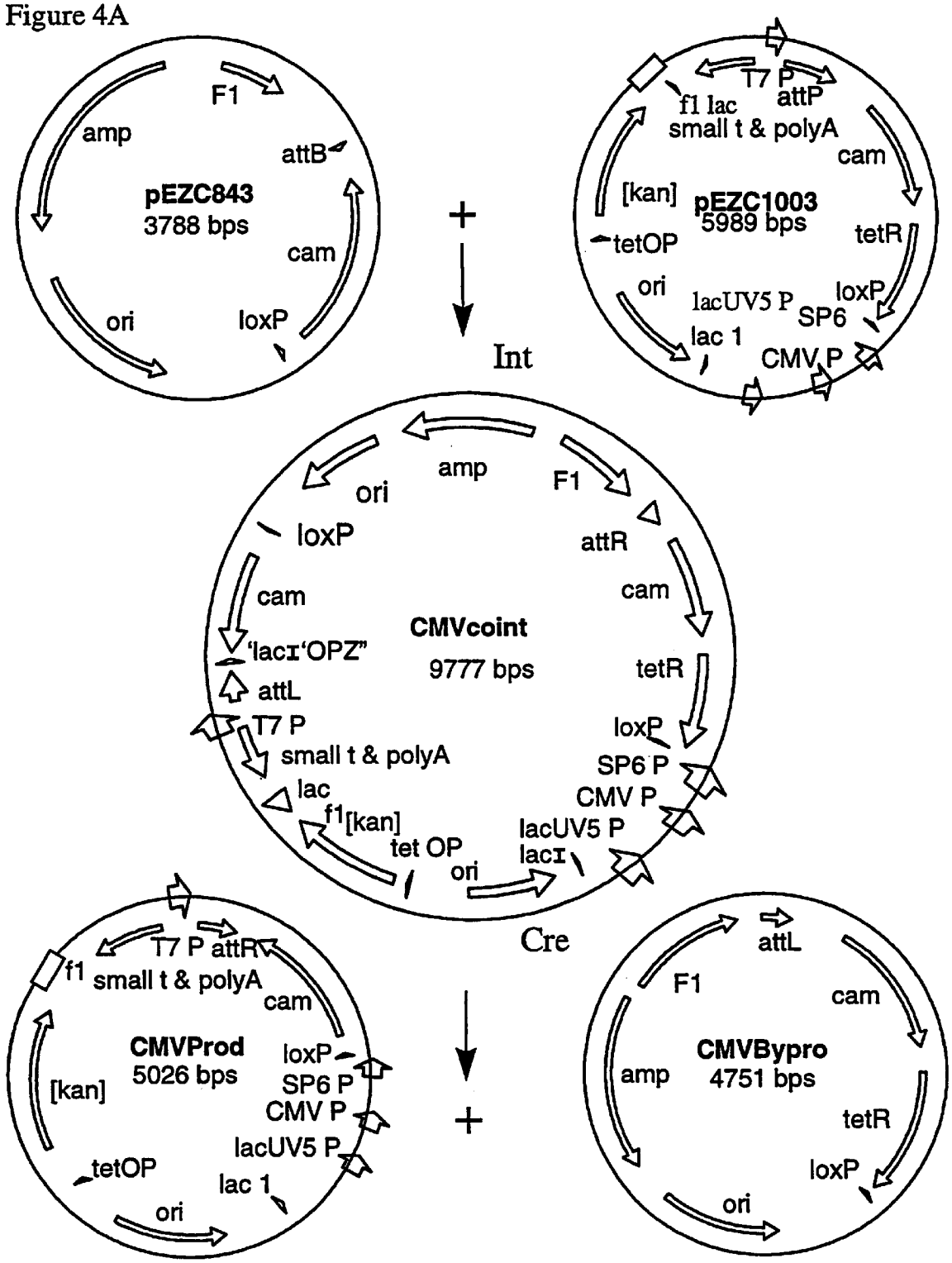
FIG. 4A depicts an application of the in vitro method of recombinational cloning to subclone the chloramphenicol acetyl transferase gene into a vector for expression in eukaryotic cells. The Insert Donor plasmid, pEZC843, is comprised of the chloramphenicol acetyl transferase gene of *E. coli*, cloned between loxP and attB sites such that the loxP site is positioned at the 5'-end of the gene. The Vector Donor plasmid, pEZC1003, contains the cytomegalovirus eukaryotic promoter apposed to a loxP site. The supercoiled plasmids were combined with lambda Integrase and Cre recombinase in vitro. After incubation, competent *E. coli* cells were transformed with the recombinational reaction solution. Aliquots of transformations were spread on agar plates containing kanamycin to select for the Product molecule (here CMVProd).

Using in vitro Recombinational Cloning to Subclone the Chloramphenicol Acetyl Transferase Gene into a Vector for Expression in Eukaryotic Cells (FIG. 4A)

Figure 4B:
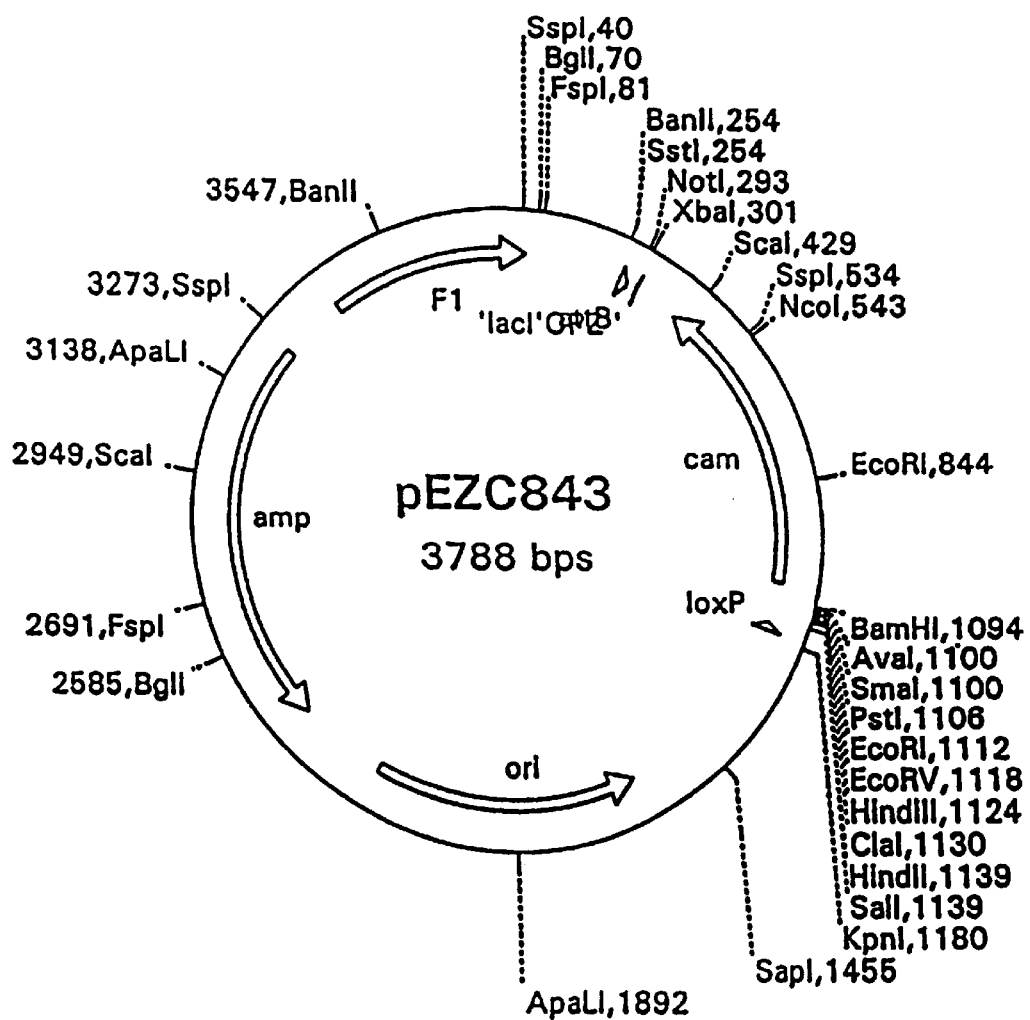
FIG. 4B depicts a restriction map of pEZC843.
Figure 4C:
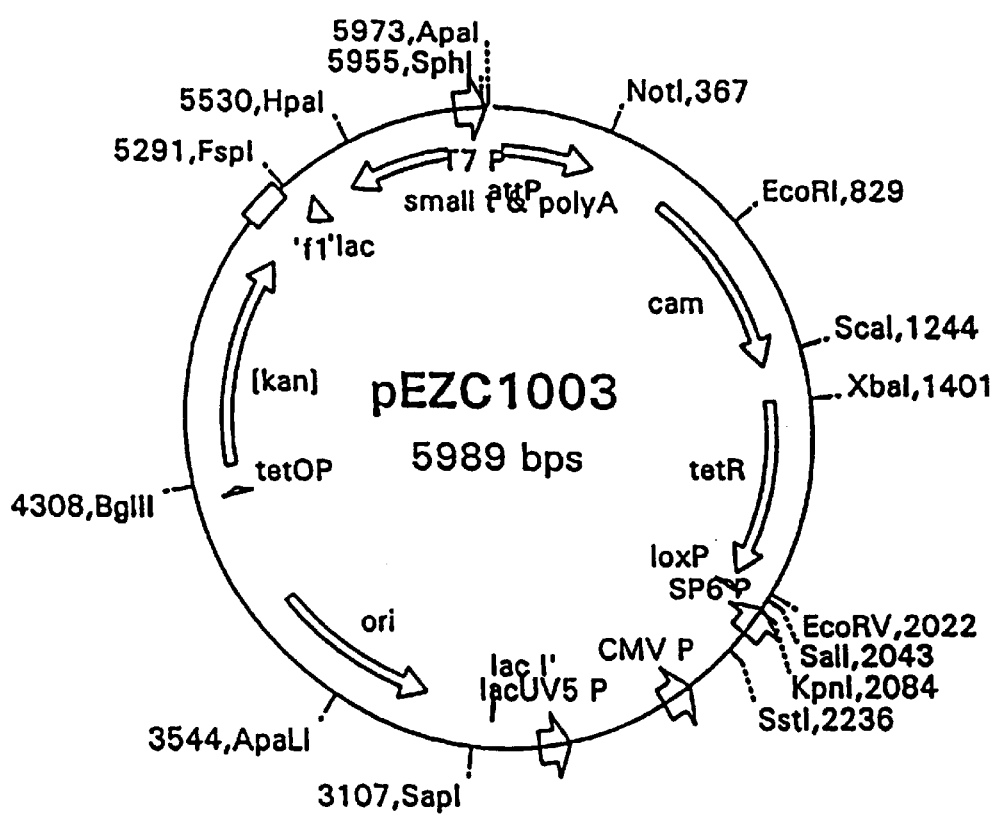
FIG. 4C depicts a restriction map of pEZC1003.
Figure 4D:
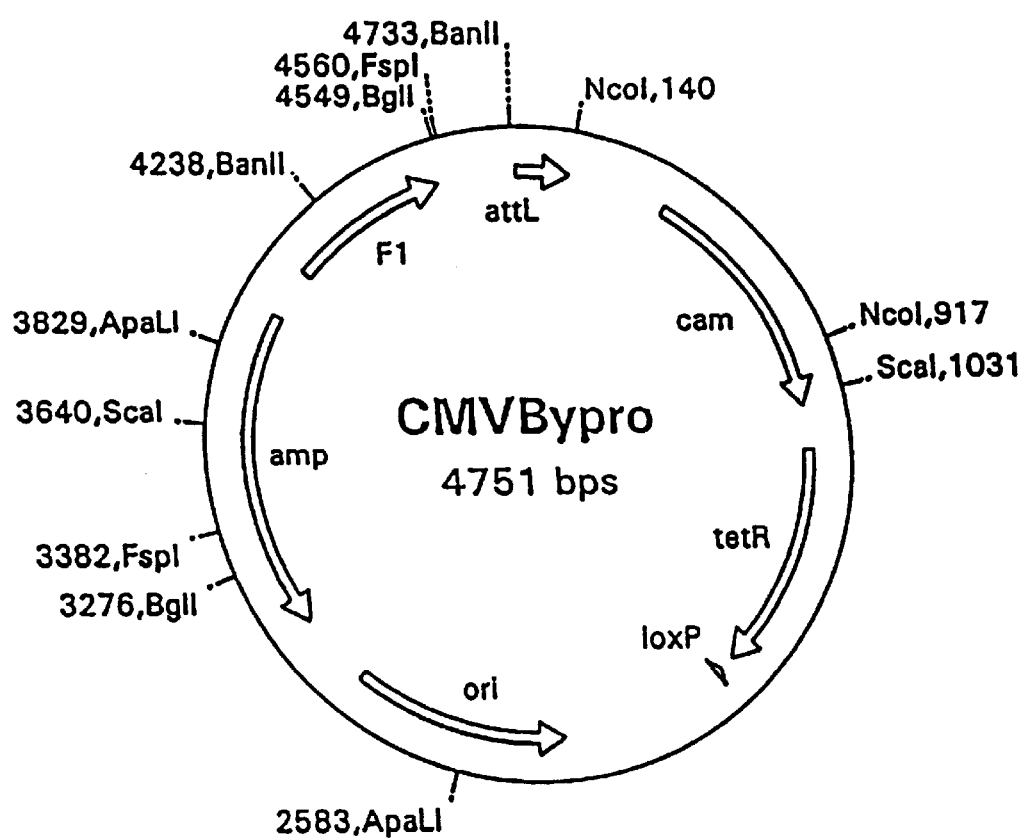
FIG. 4D depicts a restriction map of CMVBypro.
Figure 4E:
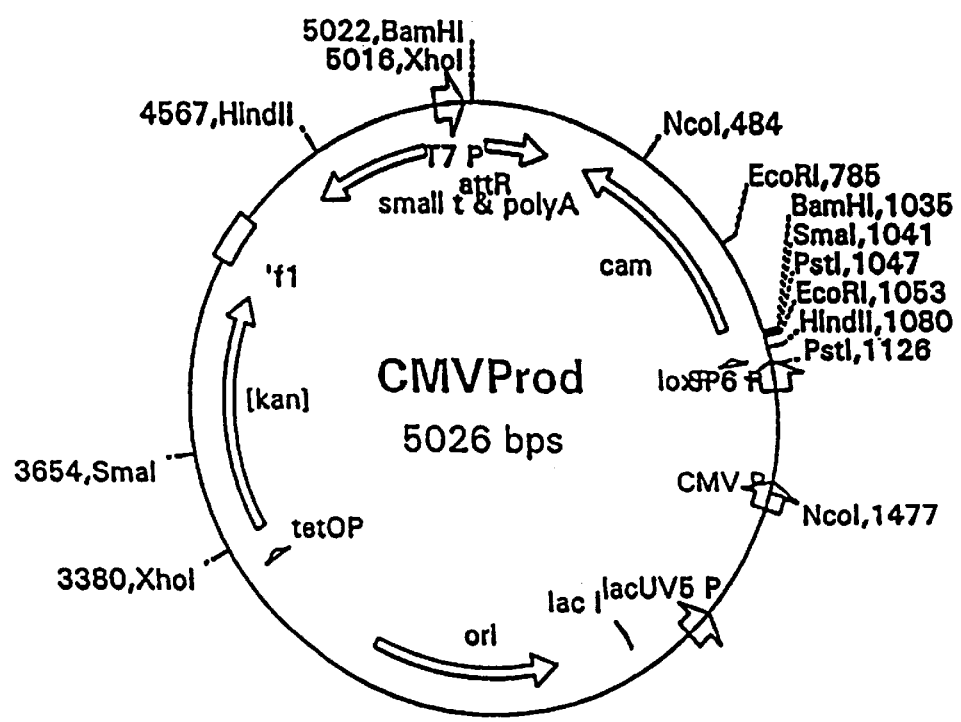
FIG. 4E depicts a restriction map of CMVProd.
Figure 4F:
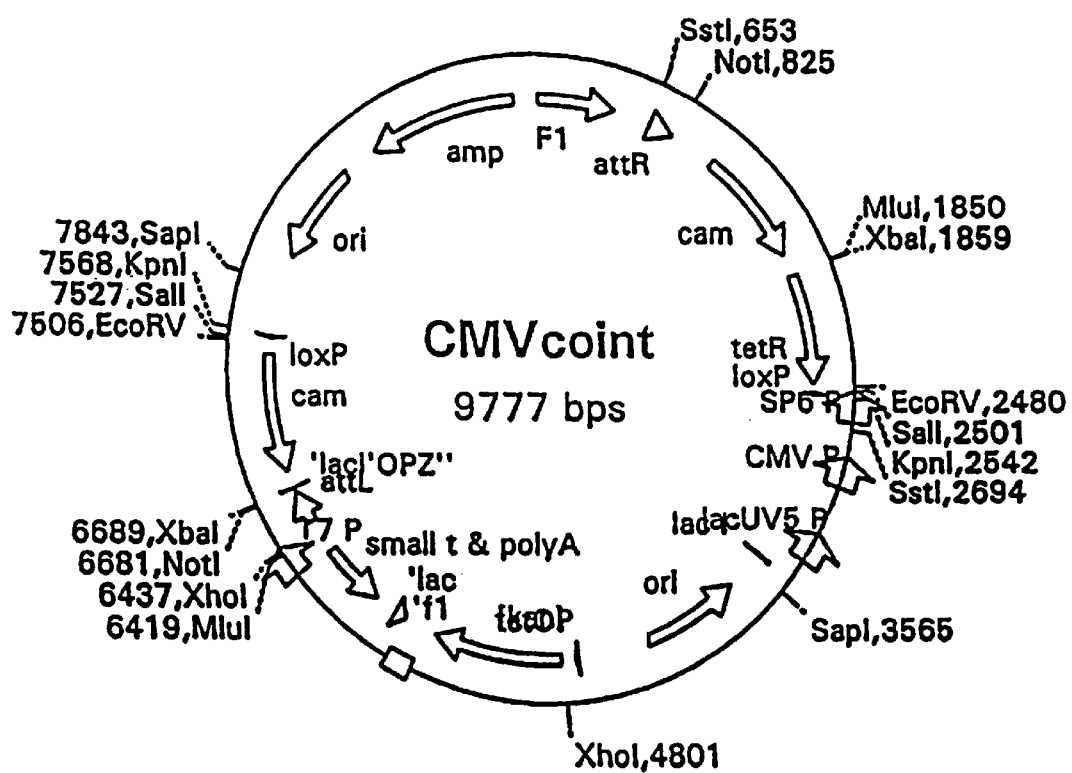
FIG. 4F depicts a restriction map of CMVcoint.

An Insert Donor plasmid, pEZC843, was constructed, comprising the chloramphenicol acetyl transferase gene of E. coli, cloned between loxP and attB sites such that the loxP site was positioned at the 5'-end of the gene (FIG. 4B). A Vector Donor plasmid, pEZC1003, was constructed, which contained the cytomegalovirus eukaryotic promoter apposed to a loxP site (FIG. 4C). One microliter aliquots of each supercoiled plasmid (about 50 ng crude miniprep DNA) were combined in a ten microliter reaction containing equal parts of lambda integrase buffer (50 mM Tris-HCl, pH 7.8, 70 mM KCl, 5 mM spermidine, 0.5 mM EDTA, 0.25 mg/ml bovine serum albumin) and Cre recombinase buffer (50 mM Tris-HCl, pH 7.5, 33 mM NaCl, 5 mM spermidine, 0.5 mg/ml bovine serum albumin), two units of Cre recombinase, 16 ng integration host factor, and 32 ng lambda integrase. After incubation at 30° C. for 30 minutes and 75° C. for 10 minutes, one microliter was transformed into competent E. coli strain DH5α (Life Technologies, Inc.). Aliquots of transformations were spread on agar plates containing 200 µg/ml kanamycin and incubated at 37° C. overnight. An otherwise identical control reaction contained the Vector Donor plasmid only. The plate receiving 10% of the control reaction transformation gave one colony; the plate receiving 10% of the recombinational cloning reaction gave 144 colonies. These numbers suggested that greater than 99% of the recombinational cloning colonies contained the desired product plasmid. Miniprep DNA made from six recombinational cloning colonies gave the predicted size plasmid (5026 base pairs), CMVProd. Restriction digestion with NcoI gave the fragments predicted for the chloramphenicol acetyl transferase cloned downstream of the CMV promoter for all six plasmids.

Example 3
Subcloned DNA Segments Flanked by attB Sites Without Stop Codons
Part I: Background The above examples are suitable for transcriptional fusions, in which transcription crosses recombination sites. However, both attR and loxP sites contain multiple stop codons on both strands, so translational fusions can be difficult, where the coding sequence must cross the recombination sites, (only one reading frame is available on each strand of loxP sites) or impossible (in attR or attL).

A principal reason for subcloning is to fuse protein domains. For example, fusion of the glutathione S-transferase (GST) domain to a protein of interest allows the fusion protein to be purified by affinity chromatography on glutathione agarose (Pharmacia, Inc., 1995 catalog). If the protein of interest is fused to runs of consecutive histidines (for example His6), the fusion protein can be purified by affinity chromatography on chelating resins containing metal ions (Qiagen, Inc.). It is of ten desirable to compare amino terminal and carboxy terminal fusions for activity, solubility, stability, and the like.

The attB sites of the bacteriophage λ integration system were examined as an alternative to loxP sites, because they are small (25 bp) and have some sequence flexibility (Nash, H. A. et al., *Proc. Natl. Acad. Sci. USA* 84:4049–4053 (1987). It was not previously suggested that multiple mutations to remove all stop codes would result in useful recombination sites for recombinational subcloning.

Using standard nomenclature for site specific recombination in lambda bacteriophage (Weisber, in *Lambda III*, Hendrix, et al., eds., Cold Spring Harbor Laboratory, Cold Spring Harbor, N.Y. (1989)), the nucleotide regions that participate in the recombination reaction in an *E. coli* host cell are represented as follows:

```
attP  --P1--H1--P2--X--H2--C-O-C'--H'--P'1--P'2--P'3--
                            +
attB                    --B-O-B'--
              Int, IHF ↓↑ Xis, Int, IHF
attR  --P1--H1--P2--X--H2--C-O-B'--
                            +
attL                    --B-O-C'--H'00P'1--P'2--P'3--,
``` where: O represents the 15 bp core DNA sequence found in both the phage and *E. coli* genomes; B and B' represent approximately 5 bases adjacent to the core in the *E. coli* genome; and P1, H1, P2, X, H2, C, C', H', P'1, P'2, and P'3 represent known DNA sequences encoding protein binding domains in the bacteriophage λ genome.

The reaction is reversible in the presence of the protein Xis (excisionase); recombination between attL and attR precisely excise the λ genome from its integrated state, regenerating the circular λ genome containing attP and the linear *E. coli* genome containing attB.

Part II: Construction and Testing of Plasmids Containing Mutant att Sites

Mutant attL and attR sites were constructed. Importantly, Landy et al. (*Ann. Rev. Biochem.* 58:913 (1989)) observed that deletion of the P1 and H1 domains of attP facilitated the excision reaction and eliminated the integration reaction, thereby making the excision reaction irreversible. Therefore, as mutations were introduced in attR, the P1 and H1 domains were also deleted. attR' sites in the present example lack the P1 and H1 regions and have the NdeI site removed (base 27630 changed from C to G), and contain sequences corresponding to bacteriophage λ coordinates 27619-27738 (GenBank release 92.0, bg:LAMCG, "Complete Sequence of Bacteriophage Lambda").

The sequence of attB produced by recombination of wild type attL and attR sites is:

```
            B            O            B'
attBwt:  5' AGCCTGCTTTTTTATACTAA CTTGA 3' (SEQ. ID
                                              NO:60)
         3' TCGGACGAAAAAATATGATT GAACT 5' (SEQ. ID
                                              NO:44)
```

The stop codons are italicized and underlined. Note that sequences of attL, attR, and attP can be derived from the attB sequence and the boundaries of bacteriophage λ contained within attL and attR (coordinates 27619 to 27818).

When mutant attR1 (attR') and attL1 sites were recombined the sequence attB1 was produced (mutations in bold, large font):

```
            B            O            B'
attB1:  5' AGCCT GCTTTTTTGTACAAA CTTGT 3' (SEQ. ID
                                              NO:6)
        3' 3'    CGAAAAAACATGTTT GAACA 5' (SEQ. ID
           TCGGA                             NO:45)
```

Note that the four stop codons are gone.

When an additional mutation was introduced in the attR1 (attR') and attL1 sequences (bold), attR2 (attR') and attL2 sites resulted. Recombination of attR2 and attL2 produced the attB2 site:

```
            B            O            B'
attB2:  5' AGCCT GCTTTCTTGTACAAA CTTGT 3' (SEQ. ID
                                              NO:7)
        3' TCGGA CGAAAGAACATGTTT GAACA 5' (SEQ. ID
                                              NO:46)
```

The recombination activities of the above attL and attR' sites were assayed as follows. The attB site of plasmid pEZC705 (FIG. 2B) was replaced with attLwt, attL1, or attL2. The attP site of plasmid pEZC726 (FIG. 2C) was replaced with attRwt, attR1 (attR', lacking regions P1 and H1) or attR2 (attR', lacking regions P1 and H1). Thus, the resulting plasmids could recombine via their loxP sites, mediated by Cre, and via their attR' and attL sites, mediated by Int, Xis, and IHF. Pairs of plasmids were mixed and reacted with Cre, Int, Xis, and IFF, transformed into *E. coli* competent cells, and plated on agar containing kanamycin.

The results are presented in Table 3:

TABLE 3

| Vector donor att site | Gene donor att site | # of kanamycin resistant colonies* |
|---|---|---|
| attR'wt (pEZC1301) | None | 1 (background) |
| attR'wt (pEZC1301) | attLwt(pEZC1313) | 147 |
| attR'wt (pEZC1301) | attL1(pEZC1317) | 47 |
| attR'wt (pEZC1301) | attL2(pEZC1321) | 0 |
| attR'1(pEZC1305) | None | 1 (background) |
| attR'1(pEZC1305) | attLwt(pEZC1313) | 4 |
| attR'1(pEZC1305) | attL1(pEZC1317) | 128 |
| attR'1(pEZC1305) | attL2(pEZC1321) | 0 |
| attR'2(pEZC1309) | None | 0 (background) |
| attR'2(pEZC1309) | attLwt(pEZC1313) | 0 |
| attR'2(pEZC1309) | attL1(pEZC1317) | 0 |
| attR'2(pEZC1309) | attL2(pEZC1321) | 209 |

(*1% of each transformation was spread on a kanamycin plate.)

The above data show that whereas the wild type att and att1 sites recombine to a small extent, the att1 and att2 sites do not recombine detectably with each other.

Part III. Recombination was demonstrated when the core region of both attB sites flanking the DNA segment of interest did not contain stop codons. The physical state of the participating plasmids was discovered to influence recombination efficiency.

Figure 5A:
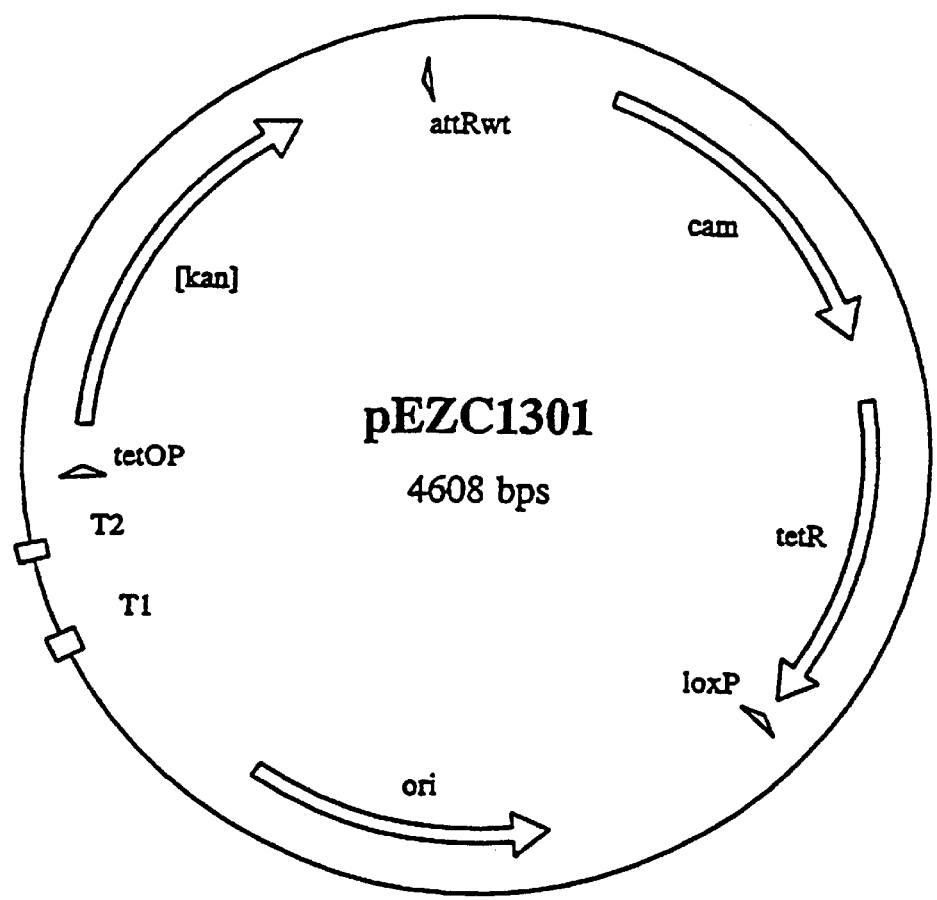
FIG. 5A depicts a vector diagram of pEZC1301.
Figure 5B:
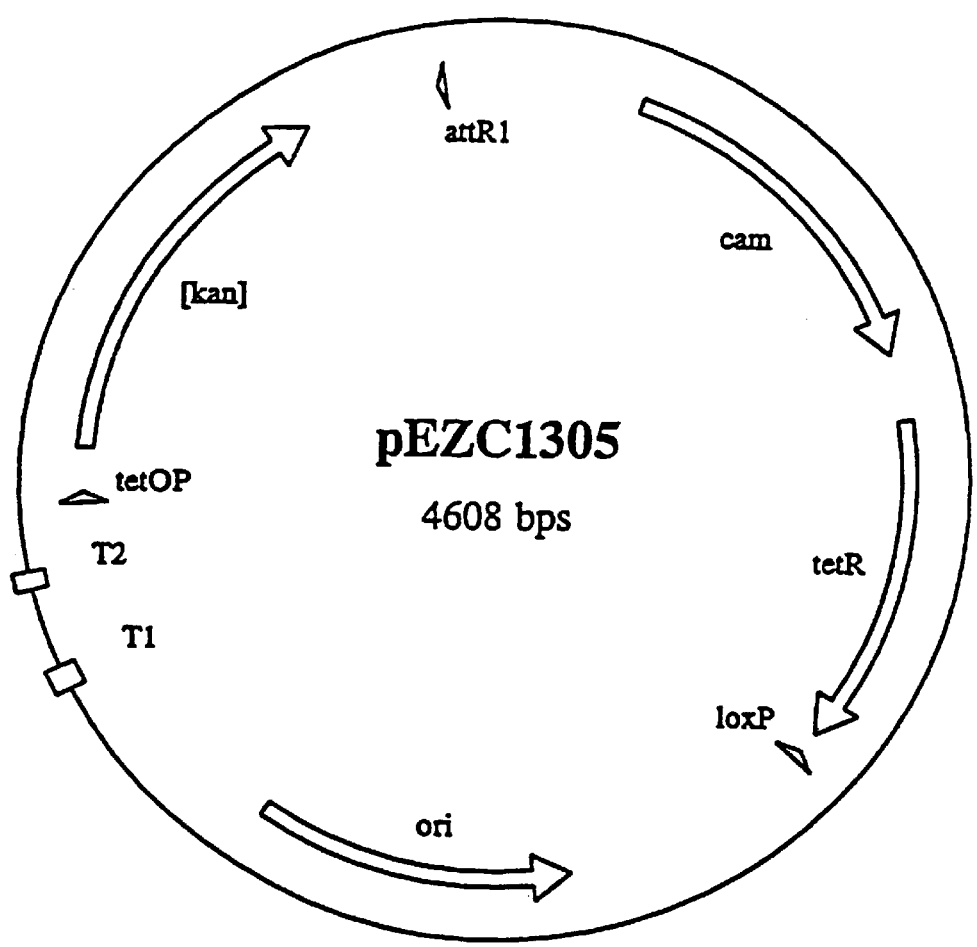
FIG. 5B depicts a vector diagram of pEZC1305.
Figure 5C:
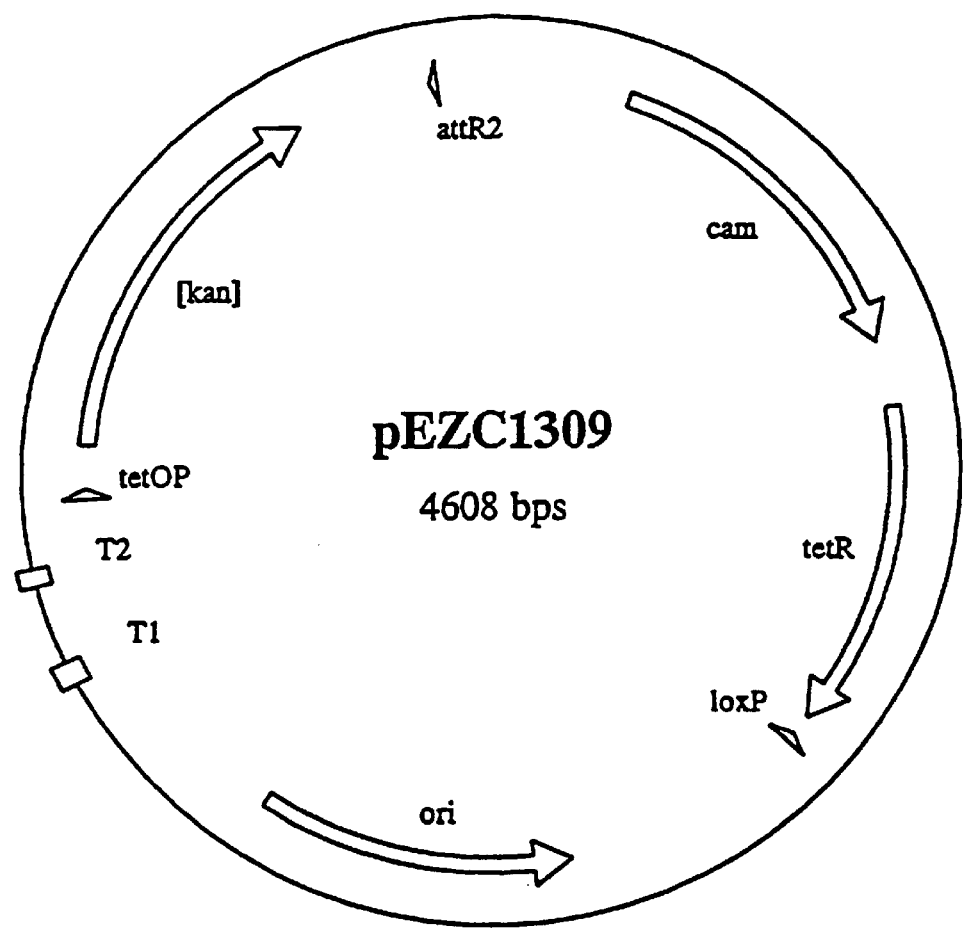
FIG. 5C depicts a vector diagram of pEZC1309.
Figure 5D:
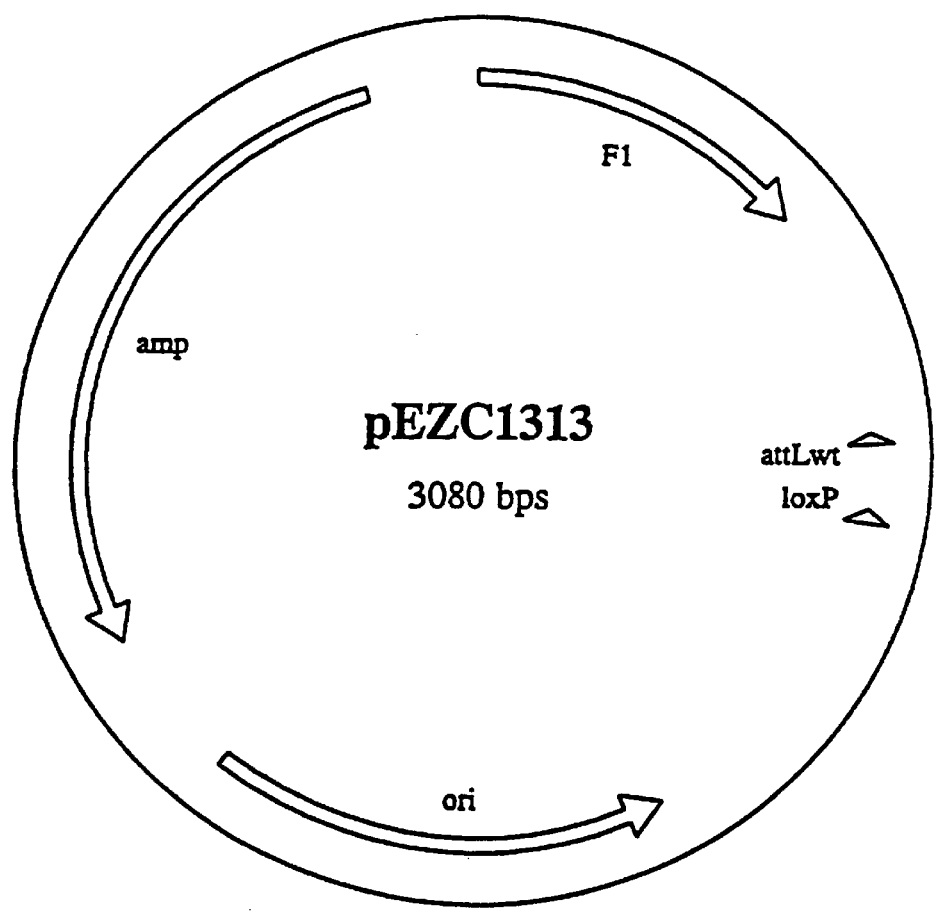
FIG. 5D depicts a vector diagram of pEZC1313.
Figure 5E:
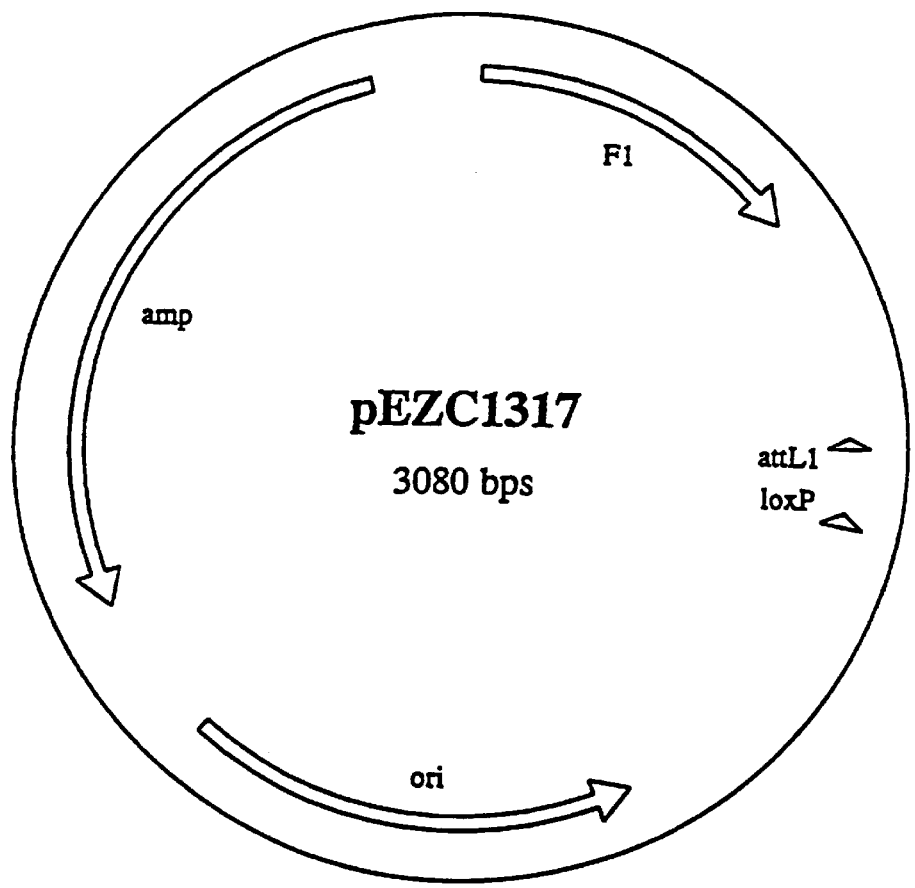
FIG. 5E depicts a vector diagram of pEZC1317.
Figure 5F:
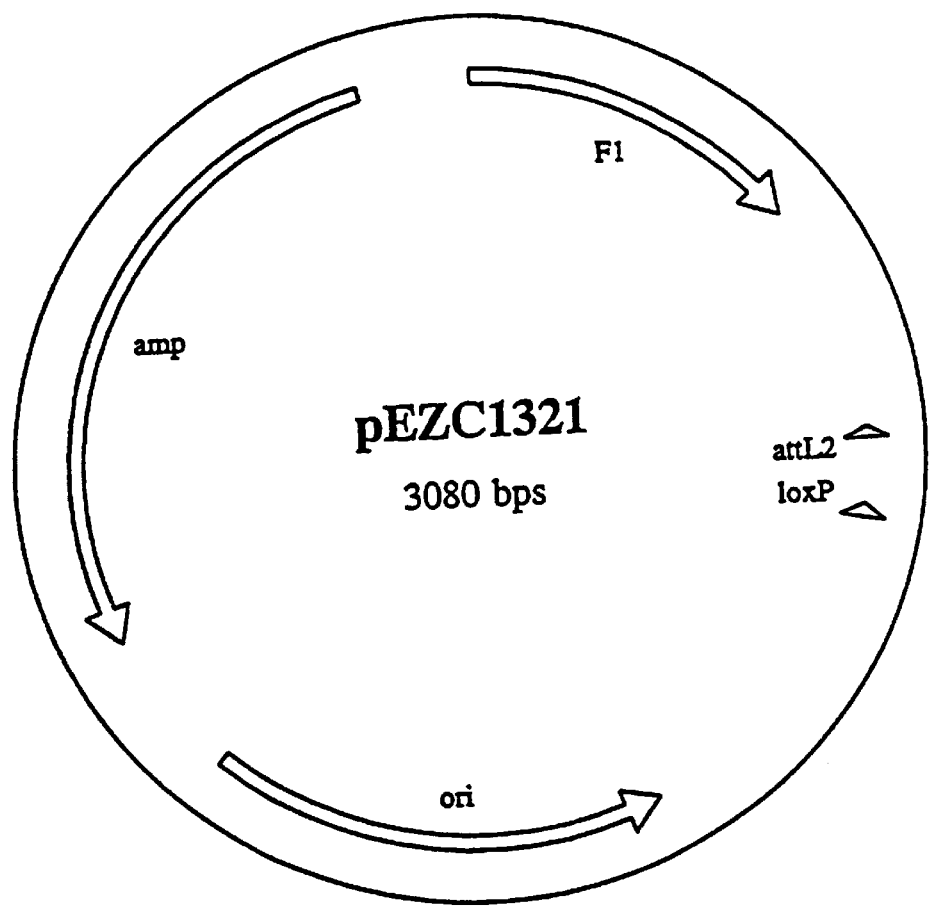
FIG. 5F depicts a vector diagram of pEZC1321.
Figure 5G:
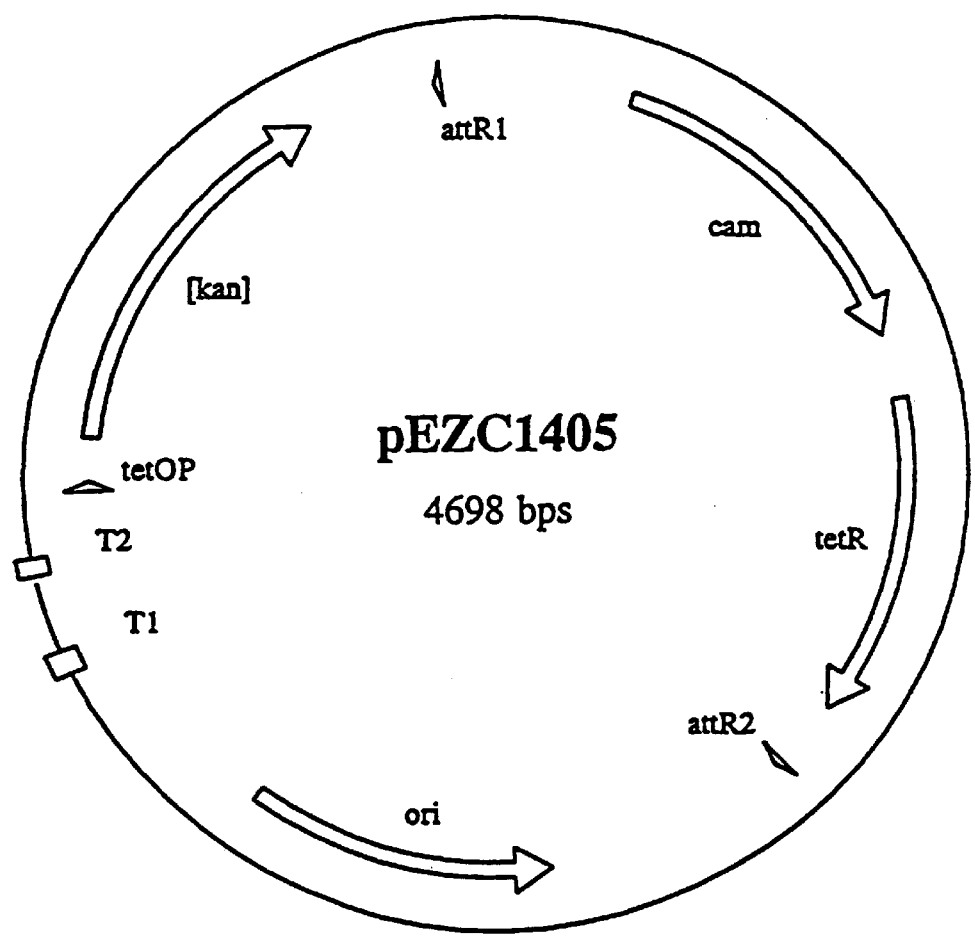
FIG. 5G depicts a vector diagram of pEZC1405.

The appropriate att sites were moved into pEZC705 and pEZC726 to make the plasmids pEZC1405 (FIG. 5G) (attR'1 and attR'2) and pEZC1502 (FIG. 5H) (attL1 and attL2). The desired DNA segment in this experiment was a copy of the chloramphenicol resistance gene cloned between the two att1 sites of pEZC1502. Pairs of plasmids were recombined in vitro using Int, Xis, and IHF (no Cre because no loxP sites were present). 100 ng of each plasmid were incubated in 10 μl reactions of 50 mM Tris HCl pH about 7.8, 16.5 mM NaCl, 35 mM KCl, 5 mM spermidine, 0.25 mM EDTA, 0.375 mg/ml BSA, 3% glycerol that contained 8.1 ng IHF, 43 ng Int, 4.3 ng Xis, and 2 units Cre. Reactions were incubated at 25° C. for 45 min., 65° C. for 10 min, and 1 μl aliquots were transformed into DH5α cells, and spread on kanamycin plates. The yield of desired kanamycin resistant colonies was determined when both parental plasmids were circular, or when one plasmid was circular and the other linear as presented in Table 4:

TABLE 4

| Vector donor[1] | Insert donor[1] | Kanamycin resistant colonies[2] |
|---|---|---|
| Circular pEZC1405 | None | 30 |
| Circular pEZC1405 | Circular pEZC1502 | 2680 |
| Linear pEZC1405 | None | 90 |
| Linear pEZC1405 | Circular pEZC1502 | 172000 |
| Circular pEZC1405 | Linear pEZC1502 | 73000 |

[1]DNAs were purified with Qiagen columns, concentrations determined by A260, and linearized with XbaI (pEZC1405) or AlwNI (pEZC1502). Each reaction contained 100 ng of the indicated DNA. All reactions (10 μl total) contained 3 μl of enzyme mix (Xis, Int, and IHF). After incubation (45 minutes at 25°, 10 minutes at 65°), one μl was used to transform E. coli DH5α cells.
[2]Number of colonies expected if the entire transformation reaction (1 ml) had been plated. Either 100 μl or 1 μl of the transformations were actually plated.

Analysis: Recombinational cloning using mutant attR and attL sites was confirmed. The desired DNA segment is subcloned between attB sites that do not contain any stop codons in either strand. The enhanced yield of Product DNA (when one parent was linear) was unexpected because of earlier observations that the excision reaction was more efficient when both participating molecules were supercoiled and proteins were limiting (Nunes-Duby et al., Cell 50:779–788 (1987).

Example 4
Demonstration of Recombinational Cloning without Inverted Repeats
Part I: Rationale The above Example 3 showed that plasmids containing inverted repeats of the appropriate recombination sites (for example, attL1 and attL2 in plasmid pEZC1502) (FIG. 5H) could recombine to give the desired DNA segment flanked by attB sites without stop codons, also in inverted orientation. A concern was the in vivo and in vitro influence of the inverted repeats. For example, transcription of a desired DNA segment flanked by attB sites in inverted orientation could yield a single stranded RNA molecule that might form a hairpin structure, thereby inhibiting translation.

Inverted orientation of similar recombination sites can be avoided by placing the sites in direct repeat arrangement att sites. If parental plasmids each have a wild type attL and wild type attR site, in direct repeat the Int, Xis, and IHF proteins will simply remove the DNA segment flanked by those sites in an intramolecular reaction. However, the mutant sites described in the above Example 3 suggested that it might be possible to inhibit the intramolecular reaction while allowing the intermolecular recombination to proceed as desired.

Figure 5H:
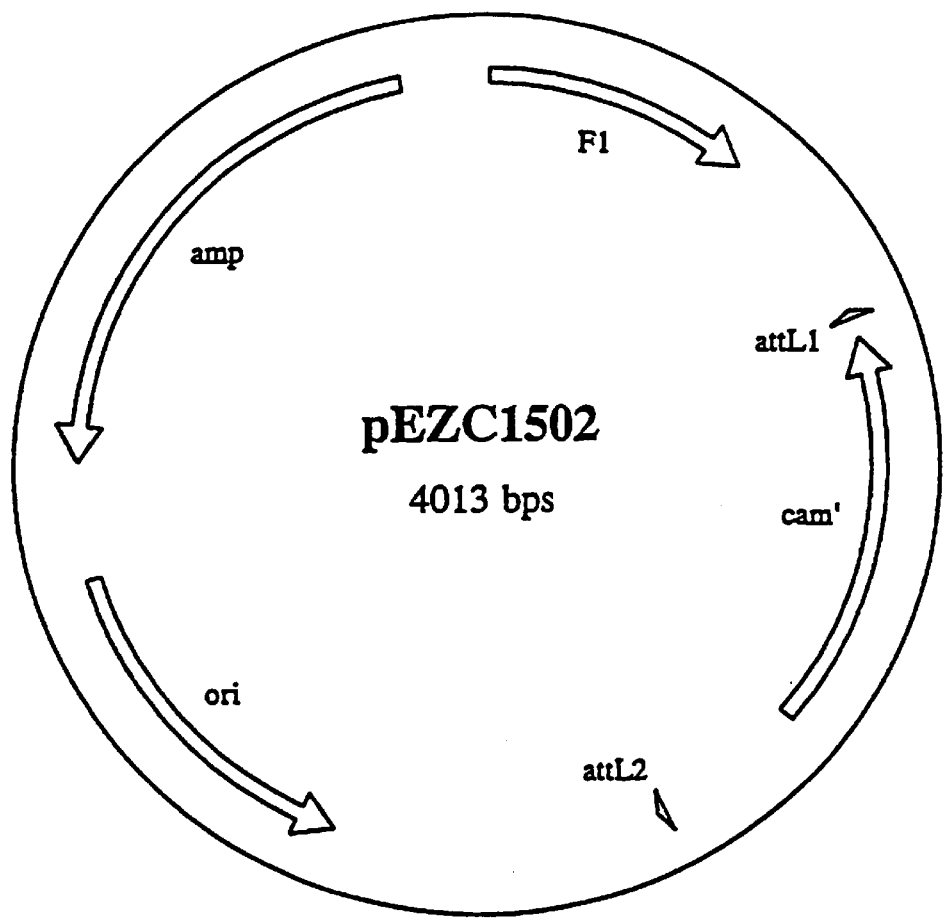
FIG. 5H depicts a vector diagram of pEZC1502.
Figure 6A:
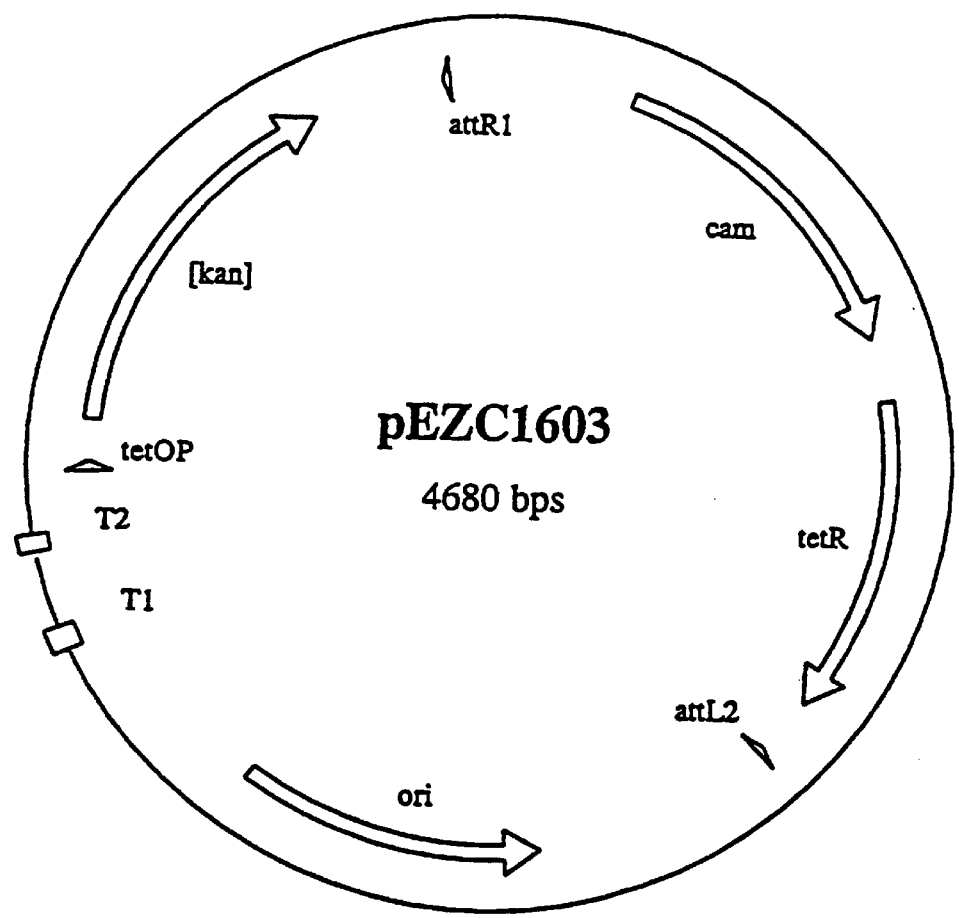
FIG. 6A depicts a vector diagram of pEZC1603.
Figure 6B:
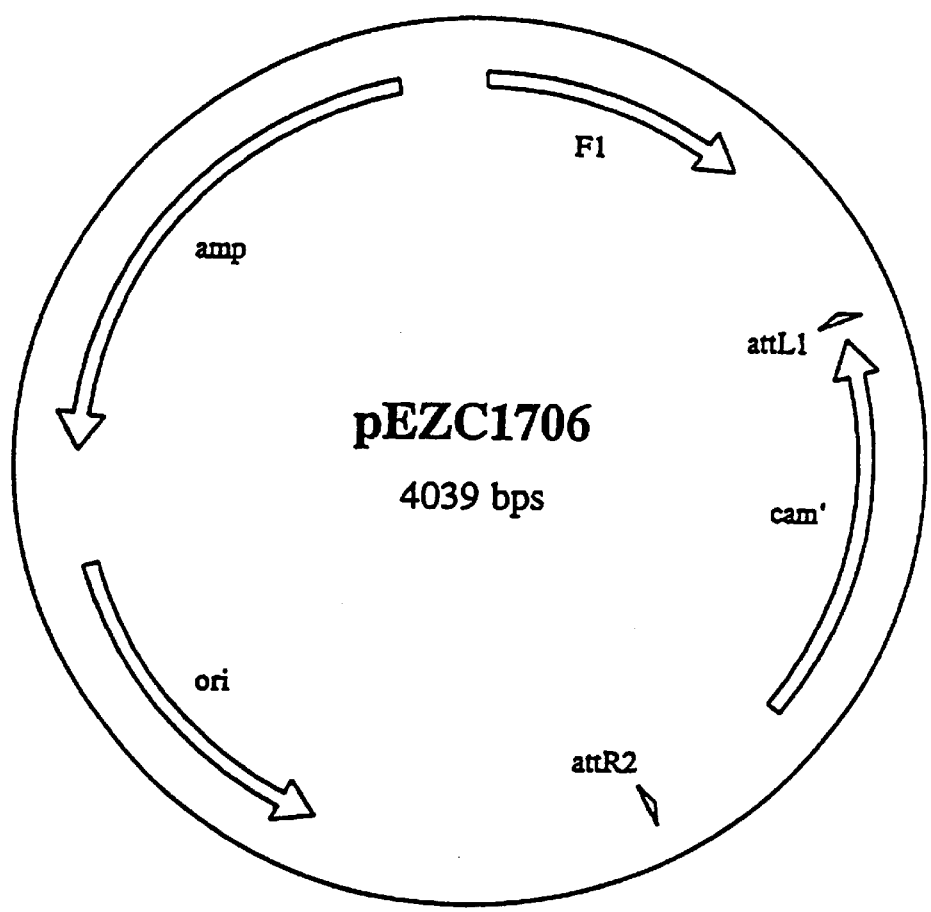
FIG. 6B depicts a vector diagram of pEZC1706.

Part II: Structure of Plasmids Without Inverted Repeats for Recombinational Cloning The attR2 sequence in plasmid pEZC1405 (FIG. 5G) was replaced with attL2, in the opposite orientation, to make pEZC1603 (FIG. 6A). The attL2 sequence of pEZC1502 (FIG. 5H) was replaced with attR2, in the opposite orientation, to make pEZC1706 (FIG. 6B). Each of these plasmids contained mutations in the core region that make intramolecular reactions between att1 and att2 cores very inefficient (see Example 3, above).

Plasmids pEZC1405, pEZC1502, pEZC1603 and pEZC1706 were purified on Qiagen columns (Qiagen, Inc.). Aliquots of plasmids pEZC1405 and pEZC1603 were linearized with XbaI. Aliquots of plasmids pEZC1502 and pEZC1706 were linearized with AlwNI. One hundred ng of plasmids were mixed in buffer (50 mM Tris HCL pH about 7.8, 16.5 mM NaCl, 35 mM KCl, 5 mM spermidine, 0.25 mM EDTA, 0.375 mg/ml BSA, 3% glycerol) containing Int (43.5 ng), Xis (4.3 ng) and IHF (8.1 ng) in a final volume of 10 μl. Reactions were incubated for 45 minutes at 25° C., 10 minutes at 65° C., and 1 μl was transformed into E. coli DH5α. After expression, aliquots were spread on agar plates containing 200 μg/ml kanamycin and incubated at 37° C.

Results, expressed as the number of colonies per 1 μl of recombination reaction are presented in Table 5:

TABLE 5

| Vector Donor | Gene Donor | Colonies | Predicted % product |
|---|---|---|---|
| Circular 1405 | — | 100 | — |
| Circular 1405 | Circular 1502 | 3740 | 3640/3740 = 97% |
| Linear 1405 | — | 90 | — |
| Linear 1405 | Circular 1502 | 172,000 | 171,910/172,000 = 99.9% |
| Circular 1405 | Linear 1502 | 73,000 | 72,900/73,000 = 99.9% |
| Circular 1603 | — | 80 | — |
| Circular 1603 | Circular 1706 | 410 | 330/410 = 80% |
| Linear 1603 | — | 270 | — |
| Linear 1603 | Circular 1706 | 7000 | 6730/7000 = 96% |
| Circular 1603 | Linear 1706 | 10,800 | 10,530/10,800 = 97% |

Analysis. In all configurations, i.e., circular or linear, the pEZC1405×pEZC1502 pair (with att sites in inverted repeat configuration) was more efficient than pEZC1603×pEZC1706 pair (with att sites mutated to avoid hairpin formation). The pEZC1603×pEZC1706 pair gave higher backgrounds and lower efficiencies than the pEZC1405×pEZC1502 pair. While less efficient, 80% or more of the colonies from the pEZC1603×pEZC1706 reactions were expected to contain the desired plasmid product. Making one partner linear stimulated the reactions in all cases.

Part III: Confirmation of Product Plasmids' Structure

Six colonies each from the linear pEZC1405 (FIG. 5G)× circular pEZC1502 (FIG. 5H), circular pEZC1405×linear pEZC1502, linear pEZC1603 (FIG. 6A)× circular pEZC1706 (FIG. 6B), and circular pEZC1603×linear pEZC1706 reactions were picked into rich medium and miniprep DNAs were prepared. Diagnostic cuts with Ssp I gave the predicted restriction fragments for all 24 colonies.

Analysis. Recombination reactions between plasmids with mutant attL and attR sites on the same molecules gave the desired plasmid products with a high degree of specificity.

Example 5
Recombinational Cloning with a Toxic Gene
Part I: Background

Restriction enzyme DpnI recognizes the sequence GATC and cuts that sequence only if the A is methylated by the dam methylase. Most commonly used *E. coli* strains are dam$^+$. Expression of DpnI in dam$^+$ strains of *E. coli* is lethal because the chromosome of the cell is chopped into many pieces. However, in dam$^-$ cells expression of DpnI is innocuous because the chromosome is immune to DpnI cutting.

In the general recombinational cloning scheme, in which the vector donor contains two segments C and D separated by recombination sites, selection for the desired product depends upon selection for the presence of segment D, and the absence of segment C. In the original Example segment D contained a drug resistance gene (Km) that was negatively controlled by a repressor gene found on segment C. When C was present, cells containing D were not resistant to kanamycin because the resistance gene was turned off.

The DpnI gene is an example of a toxic gene that can replace the repressor gene of the above embodiment. If segment C expresses the DpnI gene product, transforming plasmid CD into a dam$^+$ host kills the cell. If segment D is transferred to a new plasmid, for example by recombinational cloning, then selecting for the drug marker will be successful because the toxic gene is no longer present.

Part II: Construction of a Vector Donor Using DpnI as a Toxic Gene

The gene encoding DpnI endonuclease was amplified by PCR using primers 5'CCA CCA CAA ACG CGT CCA TGG AAT TAC ACT TTA ATT TAG3' (SEQ. ID NO: 17) and 5'CCA CCA CAA GTC GAC GCA TGC CGA CAG CCT TCC AAA TGT3' (SEQ ID NO: 18) and a plasmid containing the DpnI gene (derived from plasmids obtained from Sanford A. Lacks, Brookhaven National Laboratory, Upton, N.Y.; also available from American Type Culture Collection as ATCC 67494) as the template.

Additional mutations were introduced into the B and B' regions of attL and attR', respectively, by amplifying existing attL and attR' domains with primers containing the desired base changes. Recombination of the mutant attL3 (made with oligo Xis115) and attR'3 (attR', made with oligo Xis112) yielded attB3 with the following sequence (differences from attB1 in bold):

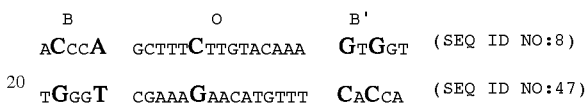

Figure 7A:
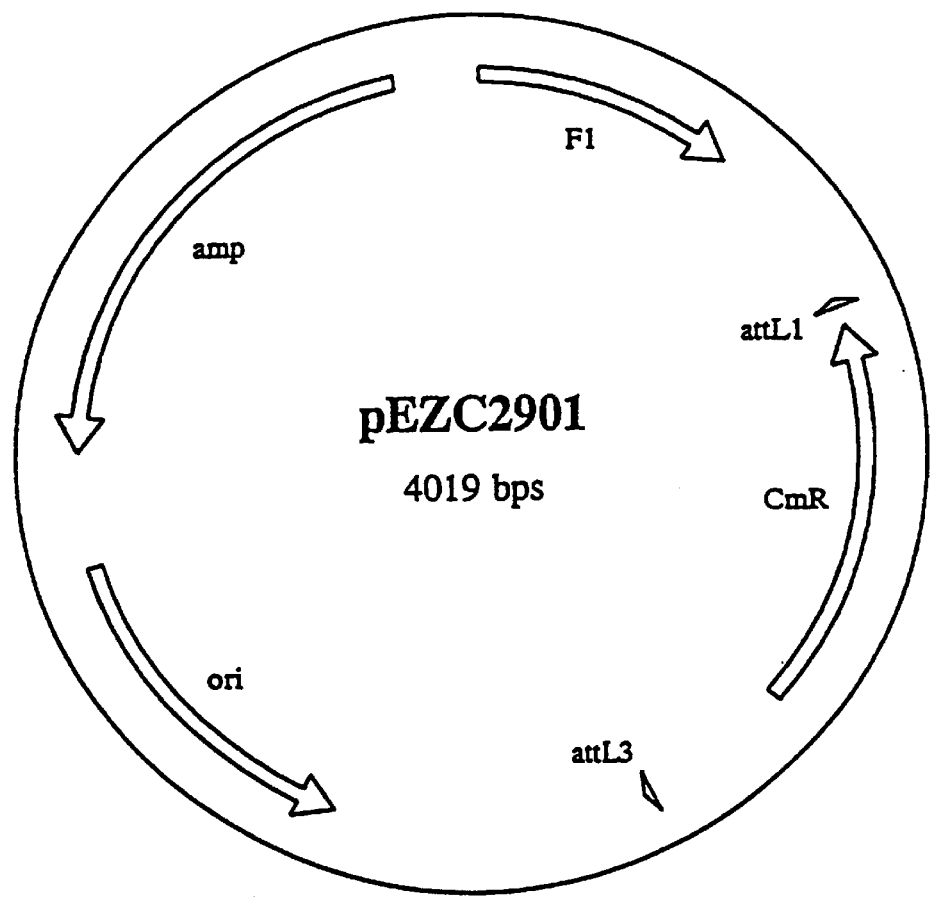
FIG. 7A depicts a vector diagram of pEZC2901.
Figure 7B:
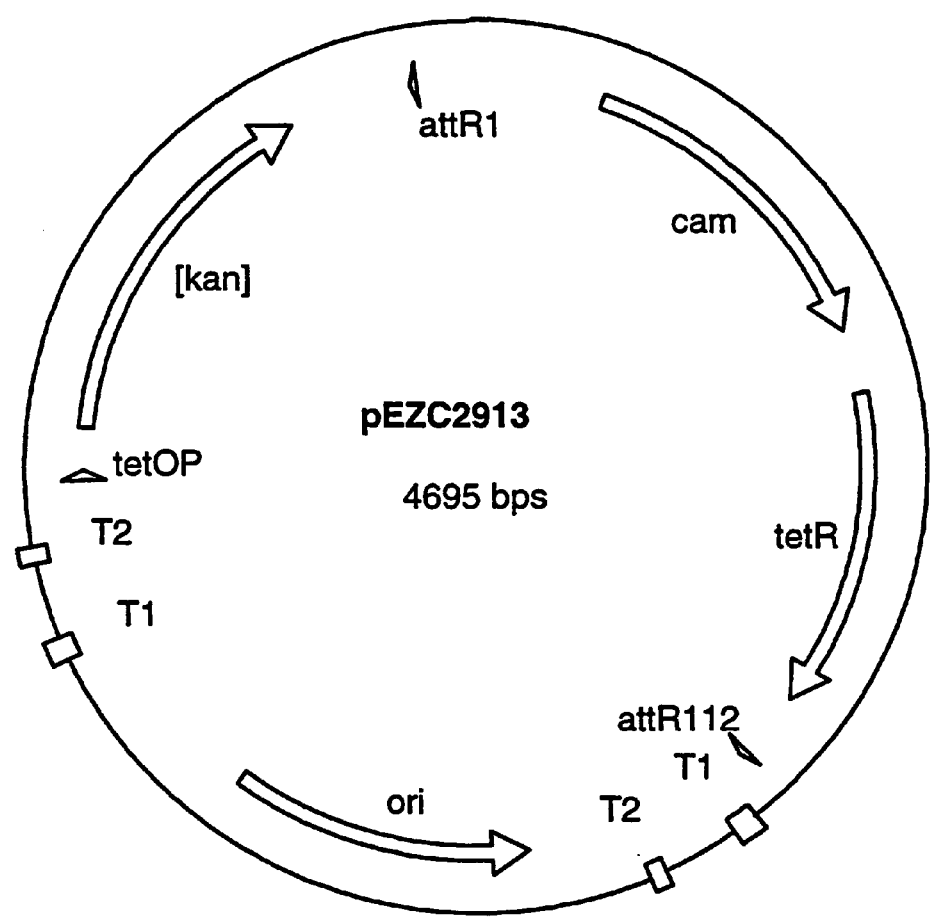
FIG. 7B depicts a vector diagram of pEZC2913.
Figure 7C:
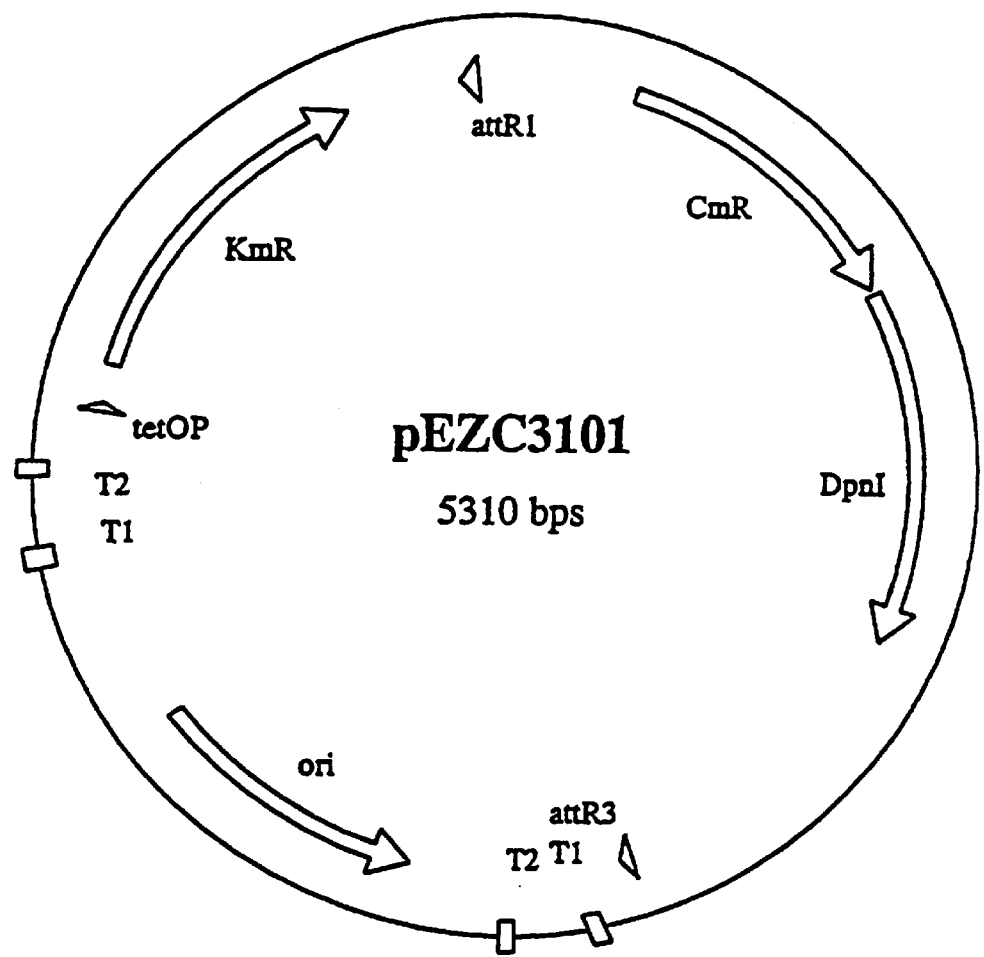
FIG. 7C depicts a vector diagram of pEZC3101.

The attL3 sequence was cloned in place of attL2 of an existing Gene Donor plasmid to give the plasmid pEZC2901 (FIG. 7A). The attR'3 sequence was cloned in place of attR'2 in an existing Vector Donor plasmid to give plasmid pEZC2913 (FIG. 7B). The DpnI gene was cloned into plasmid pEZC2913 to replace the tet repressor gene. The resulting Vector Donor plasmid was named pEZC3101 (FIG. 7C). When pEZC3101 was transformed into the dam$^-$ strain SCS110 (Stratagene), hundreds of colonies resulted. When the same plasmid was transformed into the dam$^+$ strain DH5α, only one colony was produced, even though the DH5α cells were about 20 fold more competent than the SCS110 cells. When a related plasmid that did not contain the DpnI gene was transformed into the same two cell lines, 28 colonies were produced from the SCS110 cells, while 448 colonies resulted from the DH5α cells. This is evidence that the Dpn I gene is being expressed on plasmid pEZC3101 (FIG. 7C), and that it is killing the dam$^+$ DH5α cells but not the dam$^-$ SCS110 cells.

Part III: Demonstration of Recombinational Cloning Using DpnI Selection

Figure 7D:
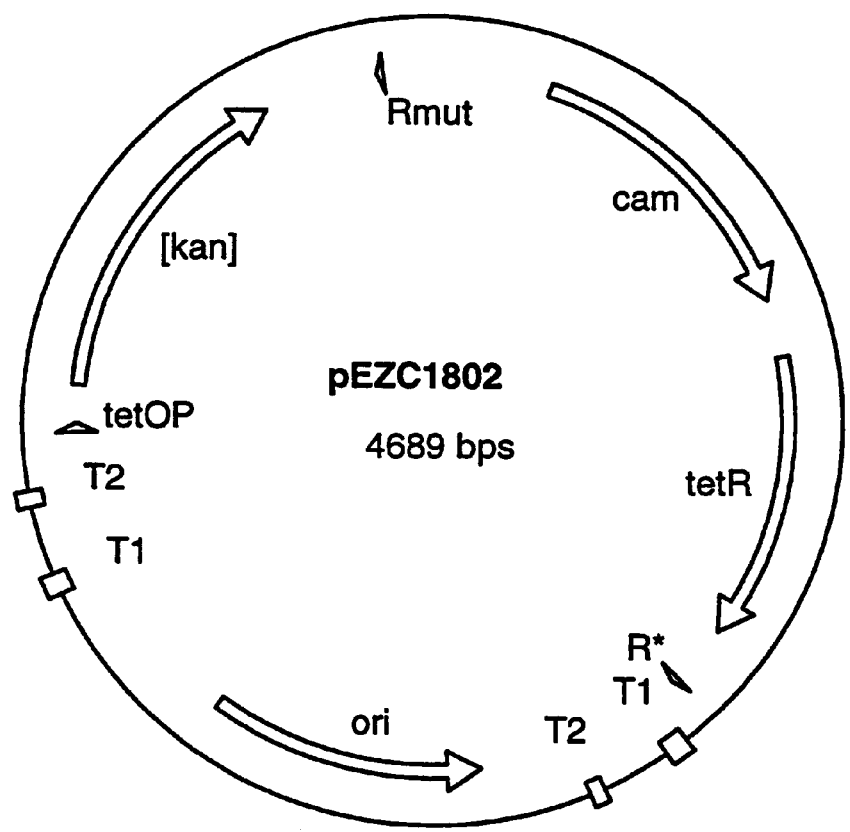
FIG. 7D depicts a vector diagram of pEZC1802.

A pair of plasmids was used to demonstrate recombinational cloning with selection for Product dependent upon the toxic gene DpnI. Plasmid pEZC3101 (FIG. 7C) was linearized with MluI and reacted with circular plasmid pEZC2901 (FIG. 7A). A second pair of plasmids using selection based on control of drug resistance by a repressor gene was used as a control: plasmid pEZC1802 (FIG. 7D) was linearized with XbaI and reacted with circular plasmid pEZC1502 (FIG. 5H). Eight microliter reactions containing buffer (50 mM Tris HCl pH about 7.8, 16.5 mM NaCl, 35 mM KCl, 5 mM spermidine, 0.375 mg/ml BSA, 0.25 mM EDTA, 2.5% glycerol) and proteins Xis (2.9 ng), Int (29 ng), and IHF (5.4 ng) were incubated for 45 minutes at 25° C., then 10 minutes at 75° C., and 1 μl aliquots were transformed into DH5α (i.e., dam$^+$) competent cells, as presented in Table 6.

TABLE 6

| Reaction # | Vector donor | Basis of selection | Insert donor | Colonies |
|---|---|---|---|---|
| 1 | pEZC3101/Mlu | Dpn I toxicity | — | 3 |
| 2 | pEZC3101/Mlu | Dpn I toxicity | Circular pEZC2901 | 4000 |

TABLE 6-continued

| Reaction # | Vector donor | Basis of selection | Insert donor | Colonies |
|---|---|---|---|---|
| 3 | pEZC1802/Xba | Tet repressor | — | 0 |
| 4 | pEZC1802/Xba | Tet repressor | Circular pEZC1502 | 12100 |

Miniprep DNAs were prepared from four colonies from reaction #2, and cut with restriction enzyme Ssp I. All gave the predicted fragments.

Analysis: Subcloning using selection with a toxic gene was demonstrated. Plasmids of the predicted structure were produced.

Example 6
Cloning of Genes with Uracil DNA Glycosylase and Subcloning of the Genes with Recombinational Cloning to Make Fusion Proteins
Part I: Converting an Existing Expression Vector to a Vector Donor for Recombinational Cloning A cassette usefull for converting existing vectors into functional Vector Donors was made as follows. Plasmid pEZC3101 (FIG. 7C) was digested with ApaI and KpnI, treated with T4 DNA polymerase and dNTPs to render the ends blunt, further digested with SmaI, HpaI, and AlwNI to render the undesirable DNA fragments small, and the 2.6 kb cassette containing the attR'1-$Cm^R$-Dpn I-attR'-3 domains was gel purified. The concentration of the purified cassette was estimated to be about 75 ng DNA/µl.

Figure 8A:
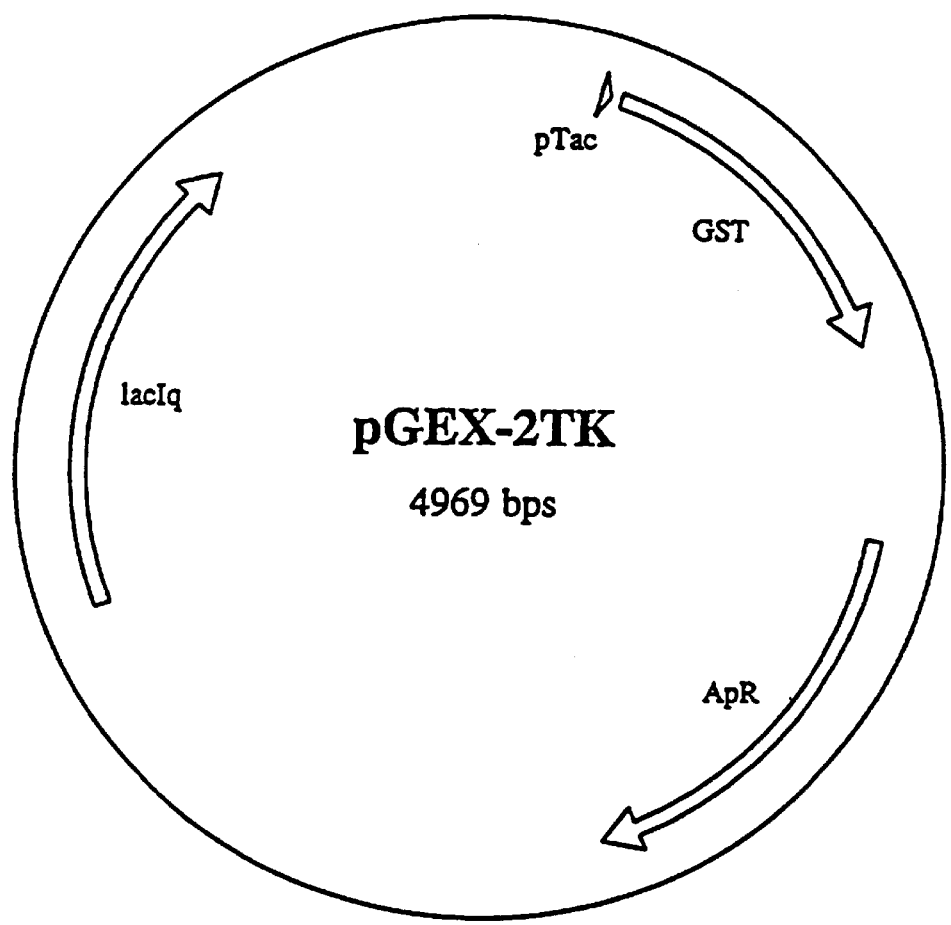
FIG. 8A depicts a vector diagram of pGEX-2TK.
Figure 8B:
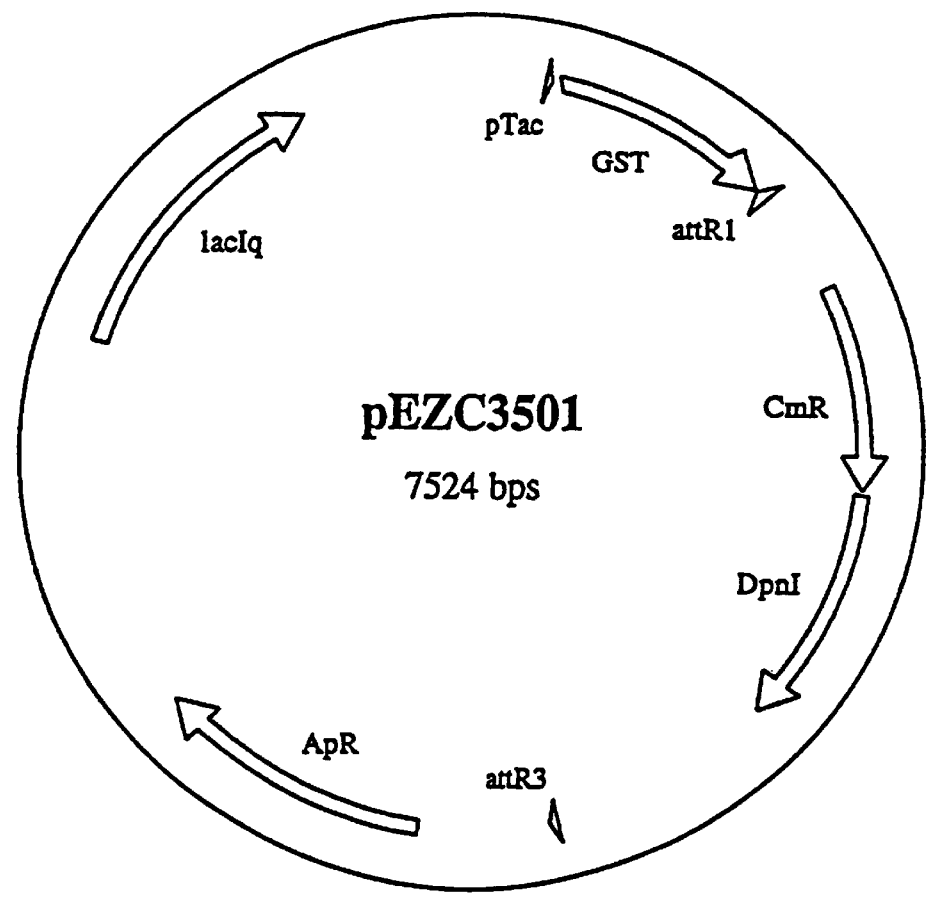
FIG. 8B depicts a vector diagram of pEZC3501.

Plasmid pGEX-2TK (FIG. 8A) (Pharmacia) allows fusions between the protein glutathione S transferase and any second coding sequence that can be inserted in frame in its multiple cloning site. pGEX-2TK DNA was digested with SmaI and treated with alkaline phosphatase. About 75 ng of the above purified DNA cassette was ligated with about 100 ng of the pGEX-2TK vector for 2.5 hours in a 5 µl ligation, then 1 µl was transformed into competent E. coli BRL 3056 cells (a dam⁻ derivative of DH10B; dam⁻ strains commercially available include DM1 from Life Technologies, Inc., and SCS 110 from Stratagene). Aliquots of the transformation mixture were plated on LB agar containing 100 µg/ml ampicillin (resistance gene present on pGEX-2TK) and 30 µg/ml chloramphenicol (resistance gene present on the DNA cassette). Colonies were picked and miniprep DNAs were made. The orientation of the cassette in pGEX-2TK was determined by diagnostic cuts with EcoRI. A plasmid with the desired orientation was named pEZC3501 (FIG. 8B).

Part II: Cloning Reporter Genes Into an Recombinational Cloning Gene Donor Plasmid in Three Reading Frames Uracil DNA glycosylase (UDG) cloning is a method for cloning PCR amplification products into cloning vectors (U.S. Pat. No. 5,334,515, entirely incorporated herein by reference). Briefly, PCR amplification of the desired DNA segment is performed with primers that contain uracil bases in place of thymidine bases in their 5' ends. When such PCR products are incubated with the enzyme UDG, the uracil bases are specifically removed. The loss of these bases weakens base pairing in the ends of the PCR product DNA, and when incubated at a suitable temperature (e.g., 37° C.), the ends of such products are largely single stranded. If such incubations are done in the presence of linear cloning vectors containing protruding 3' tails that are complementary to the 3' ends of the PCR products, base pairing efficiently anneals the PCR products to the cloning vector. When the annealed product is introduced into E. coli cells by transformation, in vivo processes efficiently convert it into a recombinant plasmid.

Figure 8C:
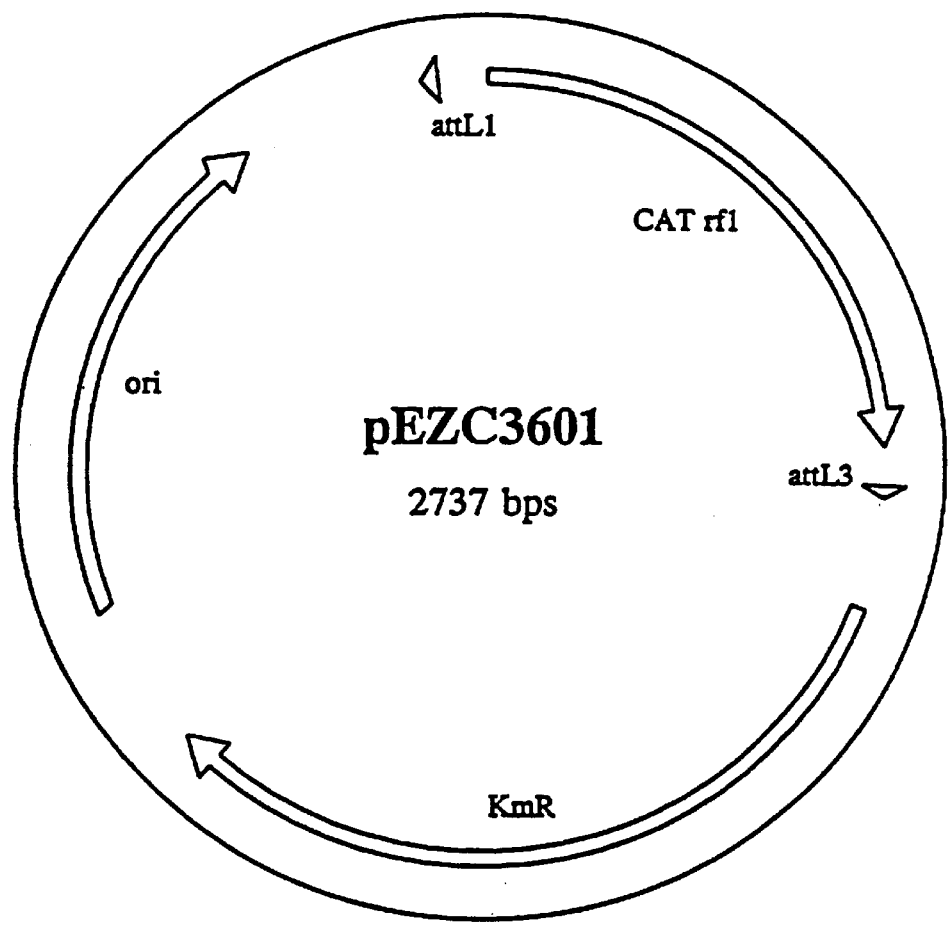
FIG. 8C depicts a vector diagram of pEZC3601.
Figure 8D:
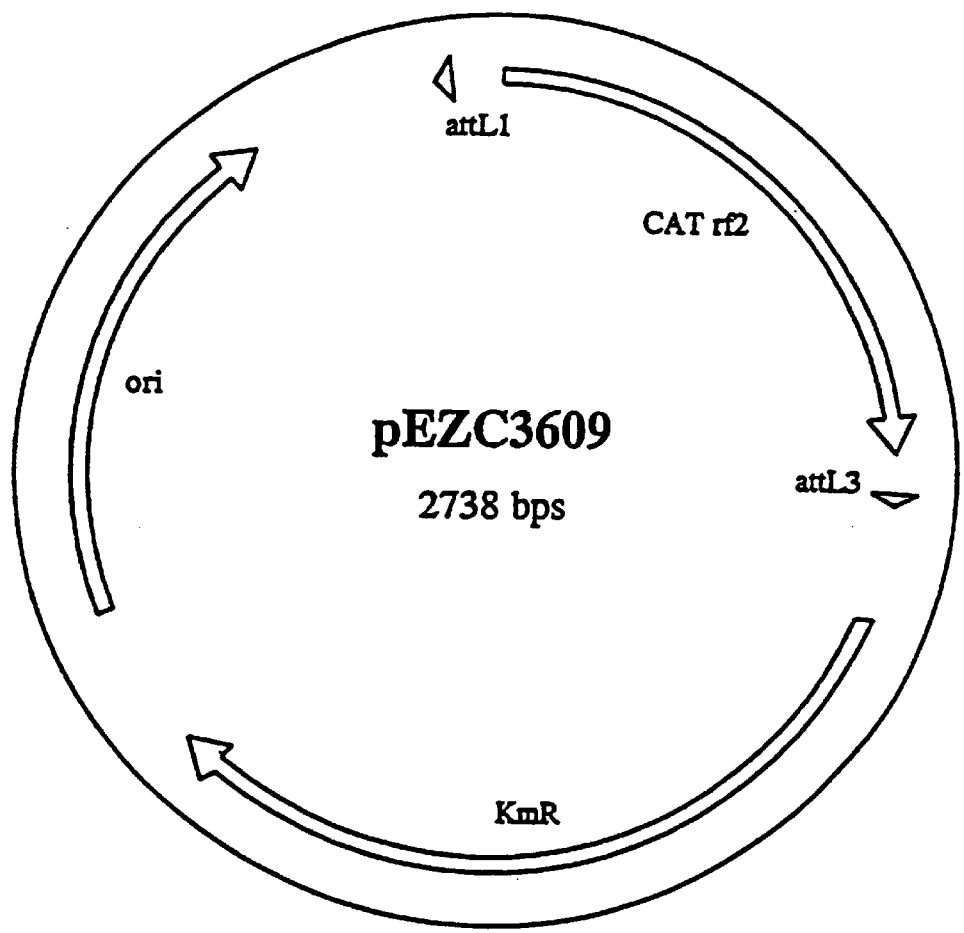
FIG. 8D depicts a vector diagram of pEZC3609.
Figure 8E:
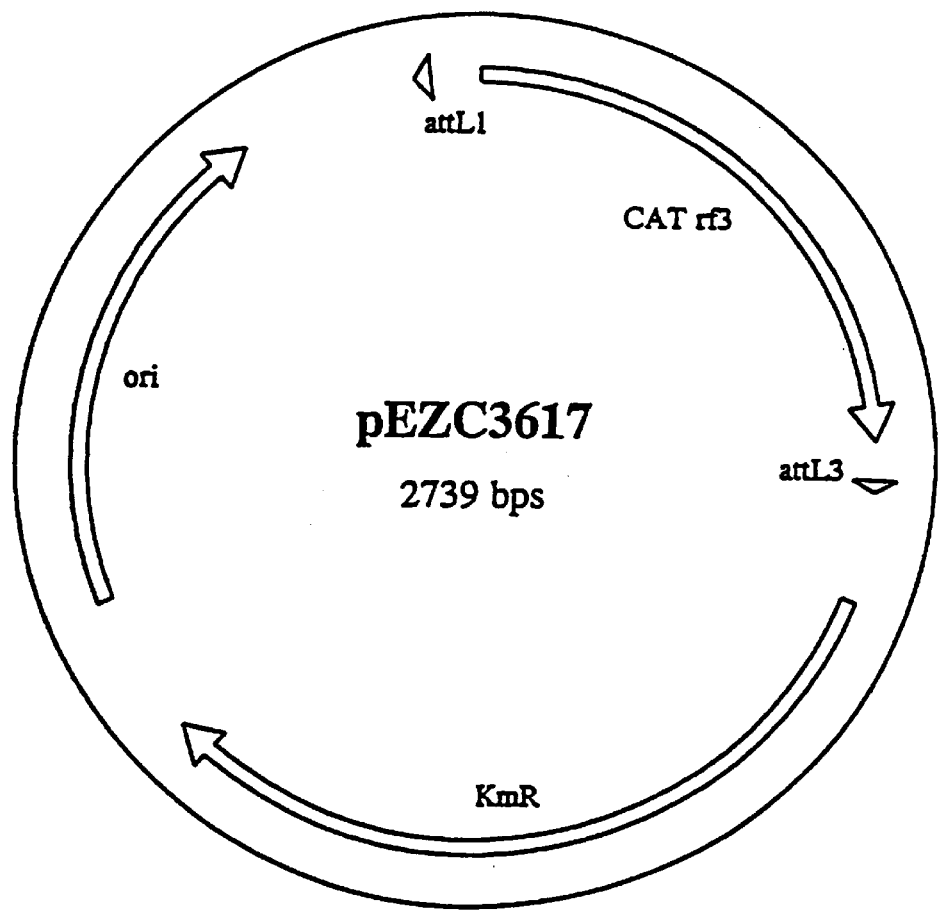
FIG. 8E depicts a vector diagram of pEZC3617.
Figure 8F:
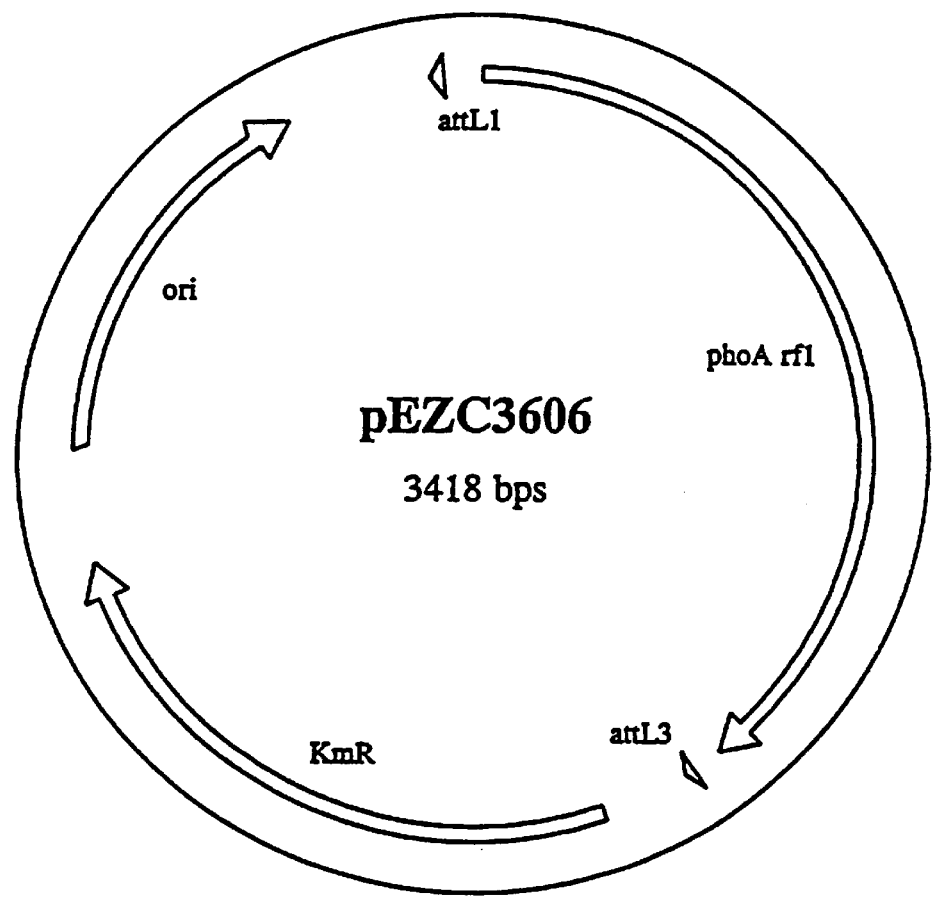
FIG. 8F depicts a vector diagram of pEZC3606.
Figure 8G:
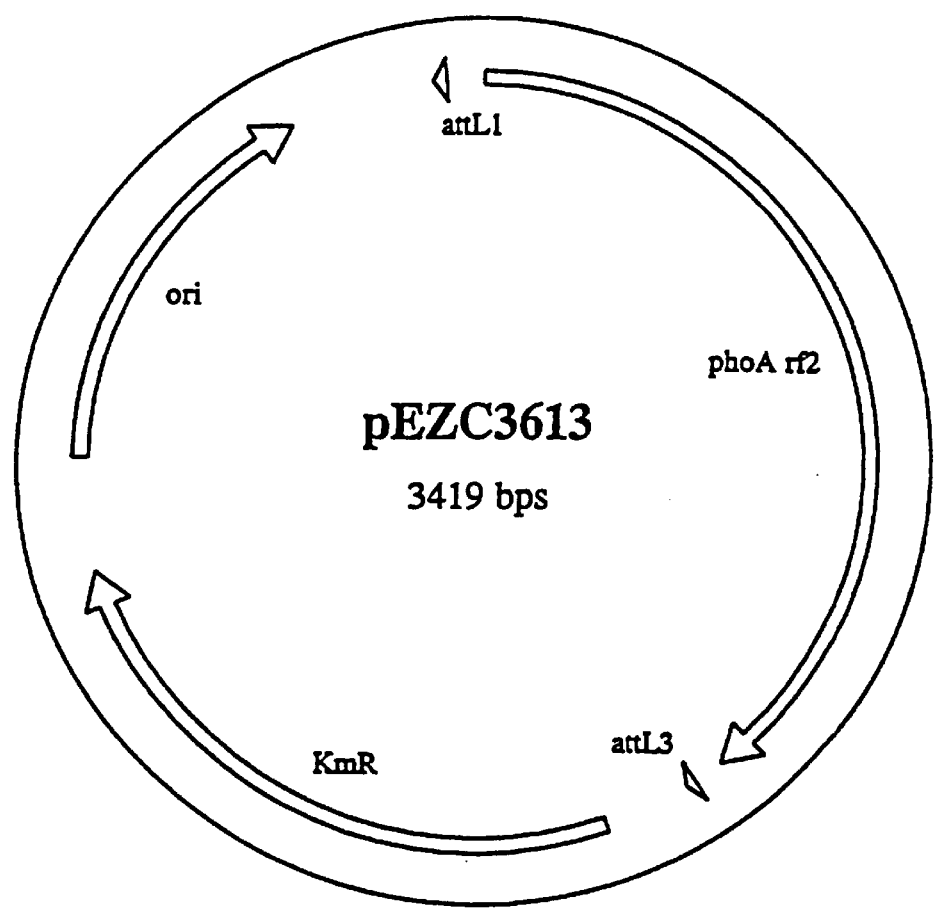
FIG. 8G depicts a vector diagram of pEZC3613.

UDG cloning vectors that enable cloning of any PCR product in all three reading frames were prepared from pEZC3201 (FIG. 8K) as follows. Eight oligonucleotides were obtained from Life Technologies, Inc. (all written 5'→3': rf1 top (GGCC GAT TAC GAT ATC CCA ACG ACC GAA AAC CTG TAT TTT CAG GGT) (SEQ. ID NO:19), rf1 bottom (CAG GTT TTC GGT CGT TGG GAT ATC GTA ATC)(SEQ. ID NO:20), rf2 top (GGCCA GAT TAC GAT ATC CCA ACG ACC GAA AAC CTG TAT TTT CAG GGT)(SEQ. ID NO:21), rf2 bottom (CAG GTT TTC GGT CGT TGG GAT ATC GTA ATC T)(SEQ. ID NO:22), rf3 top (GGCCAA GAT TAC GAT ATC CCA ACG ACC GAA AAC CTG TAT TTT CAG GGT)(SEQ. ID NO:23), rf3 bottom (CAG GTT TTC GGT CGT TGG GAT ATC GTA ATC TT)(SEQ. ID NO:24), carboxy top (ACC GTT TAC GTG GAC)(SEQ. ID NO:25) and carboxy bottom (TCGA GTC CAC GTA AAC GGT TCC CAC TTA TTA)(SEQ. ID NO:26). The rf1, 2, and 3 top strands and the carboxy bottom strand were phosphorylated on their 5' ends with T4 polynucleotide kinase, and then the complementary strands of each pair were hybridized. Plasmid pEZC3201 (FIG. 8K) was cut with NotI and SalI, and aliquots of cut plasmid were mixed with the carboxy-oligo duplex (Sal I end) and either the rf1, rf2, or rf3 duplexes (NotI ends) (10 µg cut plasmid (about 5 pmol) mixed with 250 pmol carboxy oligo duplex, split into three 20 µl volumes, added 5 µl (250 pmol) of rf1, rf2, or rf3 duplex and 2 µl=2 units T4 DNA ligase to each reaction). After 90 minutes of ligation at room temperature, each reaction was applied to a preparative agarose gel and the 2.1 kb vector bands were eluted and dissolved in 50 µl of TE.

Part III: PCR of CAT and phoA Genes

Primers were obtained from Life Technologies, Inc., to amplify the chloramphenicol acetyl transferase (CAT) gene from plasmid pACYC184, and phoA, the alkaline phosphatase gene from E. coli. The primers had 12-base 5' extensions containing uracil bases, so that treatment of PCR products with uracil DNA glycosylase (UDG) would weaken base pairing at each end of the DNAs and allow the 3' strands to anneal with the protruding 3' ends of the rf1, 2, and 3 vectors described above. The sequences of the primers (all written 5'→3') were: CAT left, UAU UUU CAG GGU ATG GAG AAA AAA ATC ACT GGA TAT ACC (SEQ. ID NO:27); CAT right, UCC CAC UUA UUA CGC CCC GCC CTG CCA CTC ATC (SEQ. ID NO:28); phoA left, UAU UUU CAG GGU ATG CCT GTT CTG GAA AAC CGG (SEQ. ID NO:29); and phoA right, UCC CAC UUA UUA TTT CAG CCC CAG GGC GGC TTT C (SEQ. ID NO:30). The primers were then used for PCR reactions using known method steps (see, e.g., U.S. Pat. No. 5,334,515, entirely incorporated herein by reference), and the polymerase chain reaction amplification products obtained with these primers comprised the CAT or phoA genes with the initiating ATGs but without any transcriptional signals. In addition, the uracil-containing sequences on the amino termini encoded the cleavage site for TEV protease (Life Technologies, Inc.), and those on the carboxy terminal encoded consecutive TAA nonsense codons.

Figure 8H:
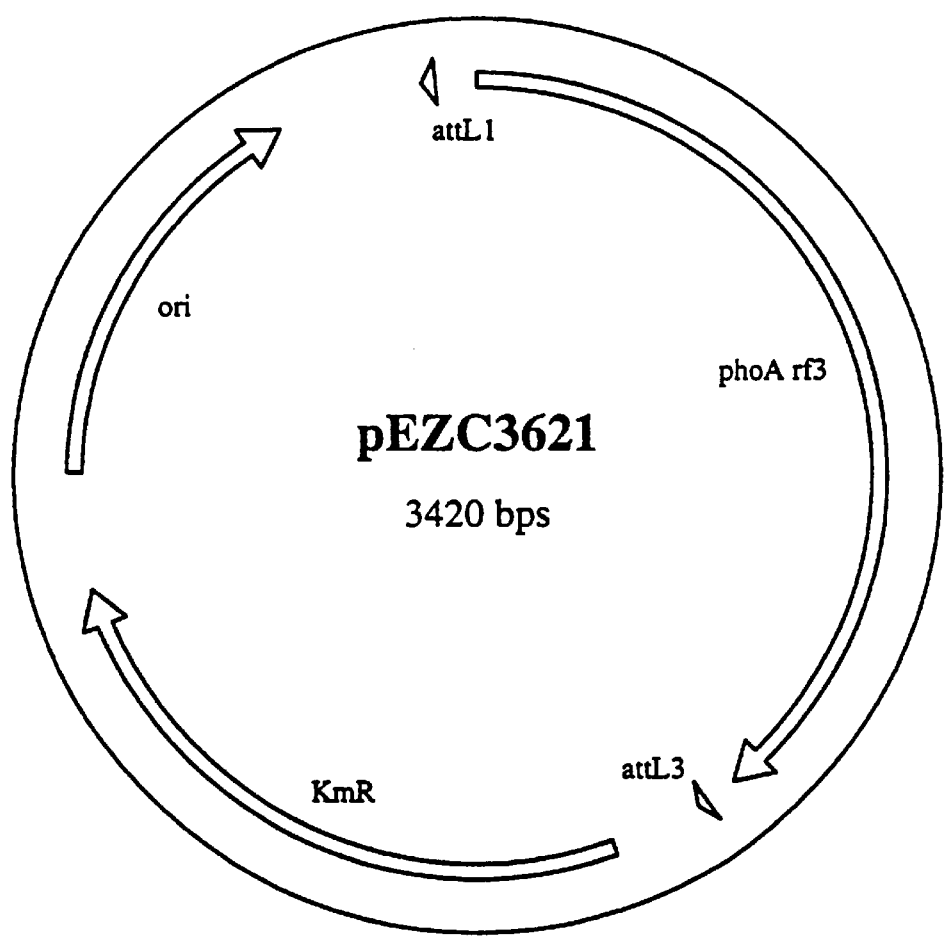
FIG. 8H depicts a vector diagram of pEZC3621.

Unpurified PCR products (about 30 ng) were mixed with the gel purified, linear rf1, rf2, or rf3 cloning vectors (about 50 ng) in a 10 µl reaction containing 1×REact 4 buffer (LTI) and 1 unit UDG (LTI). After 30 minutes at 37° C., 1 µl aliquots of each reaction were transformed into competent E. coli DH5α cells (LTI) and plated on agar containing 50 µg/ml kanamycin. Colonies were picked and analysis of miniprep DNA showed that the CAT gene had been cloned in reading frame 1 (pEZC3601) (FIG. 8C), reading frame 2 (pEZC3609) (FIG. 8D) and reading frame 3 (pEZC3617) (FIG. 8E), and that the phoA gene had been cloned in reading frame 1 (pEZC3606) (FIG. 8F), reading frame 2 (pEZC3613) (FIG. 8G) and reading frame 3 (pEZC3621) (FIG. 8H).

Part IV: Subcloning of CAT or phoA from UDG Cloning Vectors into a GST Fusion Vector Plasmids encoding fusions between GST and either CAT or phoA in all three reading frames were constructed by recombinational cloning as follows. Miniprep DNA of GST vector donor pEZC3501(FIG. 8B) (derived from Pharmacia plasmid pGEX-2TK as described above) was linearized with ClaI. About 5 ng of vector donor were mixed with about 10 ng each of the appropriate circular gene donor vectors containing CAT or phoA in 8 μl reactions containing buffer and recombination proteins Int, Xis, and IHF (Example 5). After incubation, 1 μl of each reaction was transformed into E. coli strain DH5α and plated on ampicillin, as presented in Table 7.

TABLE 7

| DNA | Colonies (10% of each transformation) |
|---|---|
| Linear vector donor (pEZC3501/Cla) | 0 |
| Vector donor + CAT rf1 | 110 |
| Vector donor + CAT rf2 | 71 |
| Vector donor + CAT rf3 | 148 |
| Vector donor + phoA rf1 | 121 |
| Vector donor + phoA rf2 | 128 |
| Vector donor + phoA rf3 | 31 |

Part V: Expression of Fusion Proteins

Two colonies from each transformation were picked into 2 ml of rich medium (CIRCLEGROW® brand culture medium, Bio101 Inc.) in 17×100 mm plastic tubes (FALCON® brand plastics are, Cat. No. 2059, Becton Dickinson) containing 100 μg/ml ampicillin and shaken vigorously for about 4 hours at 37° C., at which time the cultures were visibly turbid. One ml of each culture was transferred to a new tube containing 10 μl of 10% (w/v) IPTG to induce expression of GST. After 2 hours additional incubation, all cultures had about the same turbidity; the A600 of one culture was 1.5. Cells from 0.35 ml each culture were harvested and treated with sample buffer (containing SDS and β-mercaptoethanol) and aliquots equivalent to about 0.15 A600 units of cells were applied to aNovex4–20% gradient polyacrylamide gel. Following electrophoresis the gel was stained with Coomassie blue.

Figure 8I:
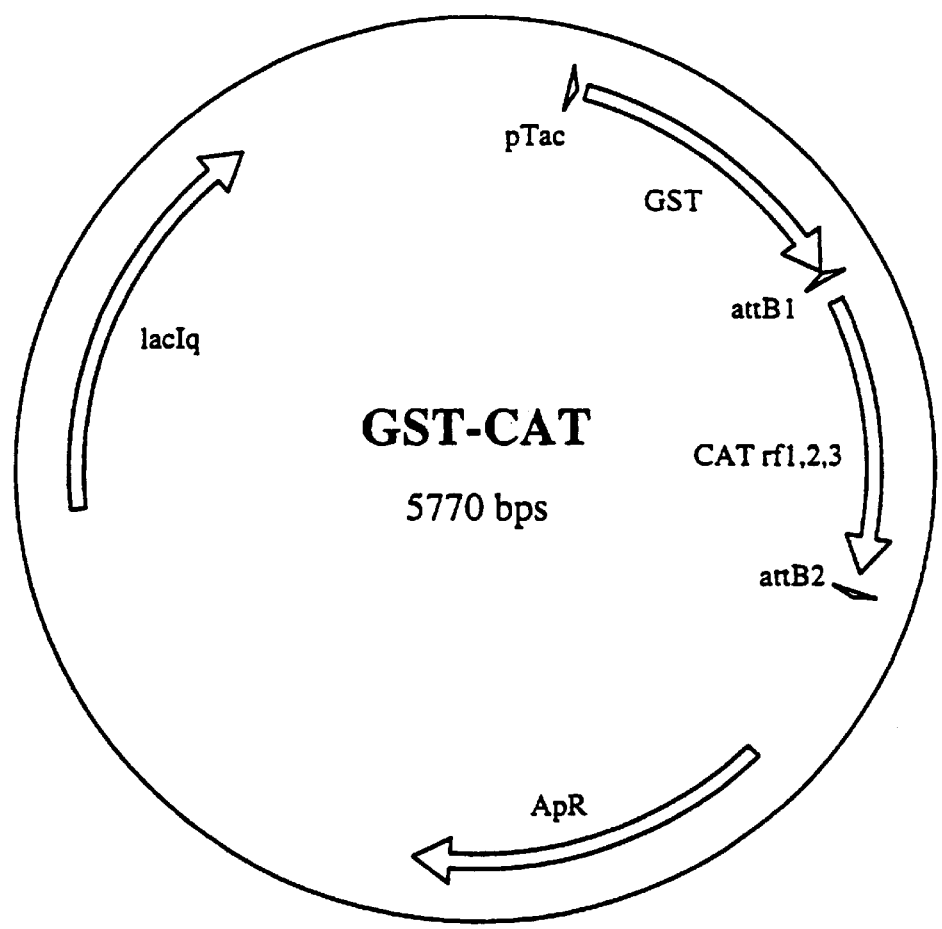
FIG. 8I depicts a vector diagram of GST-CAT.
Figure 8J:
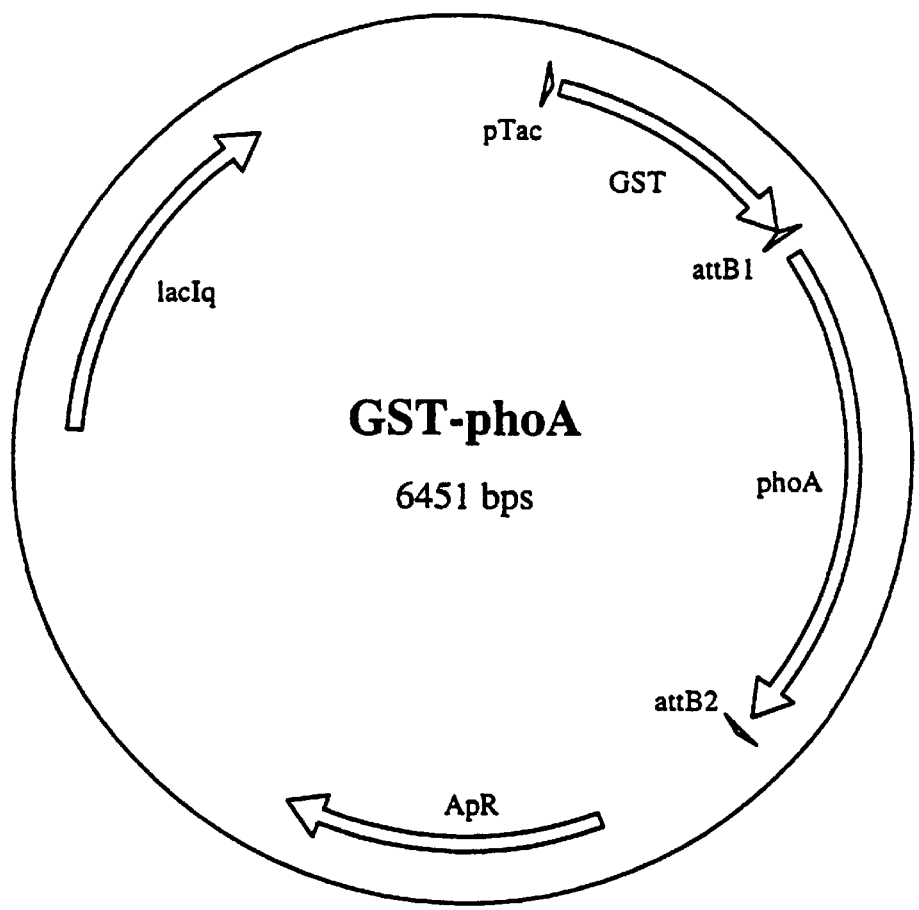
FIG. 8J depicts a vector diagram of GST-phoA.
Figure 8K:
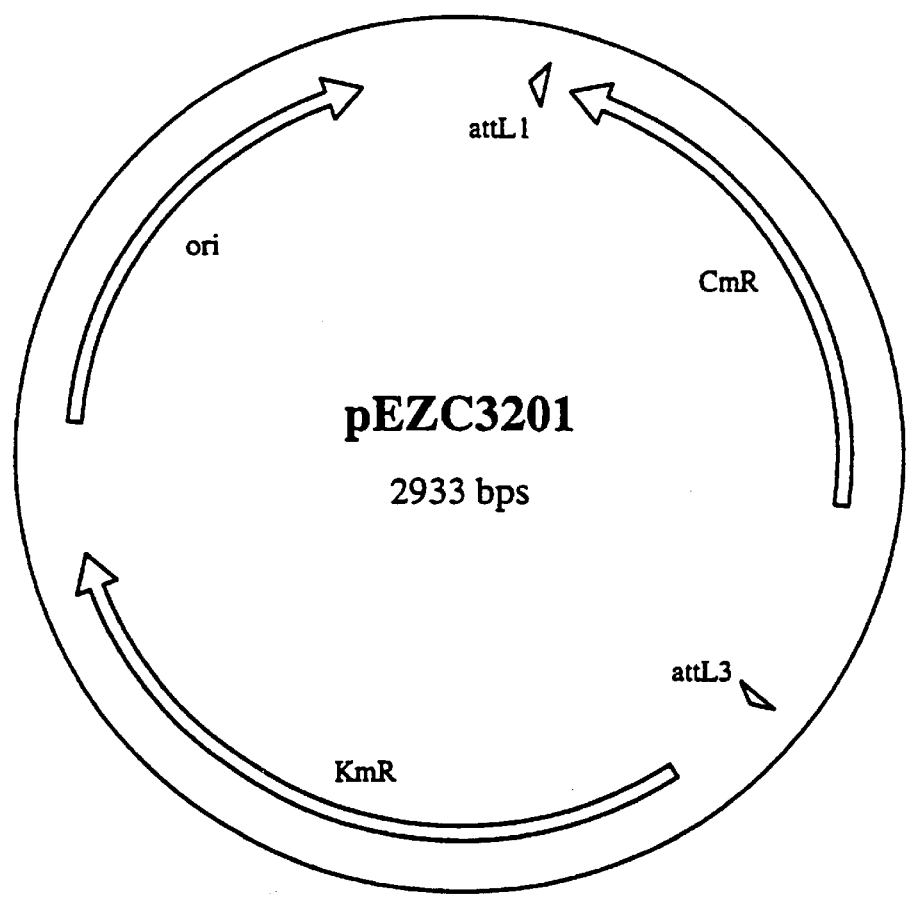
FIG. 8K depicts a vector diagram of pEZC3201.

Results: Enhanced expression of single protein bands was seen for all 12 cultures. The observed sizes of these proteins correlated well with the sizes predicted for GST being fused (through attB recombination sites without stop codons) to CAT (FIG. 8I) or phoA (FIG. 8J) in three reading frames: CAT rf1=269 amino acids; CAT rf2=303 amino acids; CAT rf3=478 amino acids; phoA rf1=282 amino acids; phoA rf2=280 amino acids; and phoA rf3=705 amino acids.

Analysis: Both CAT and phoA genes were subcloned into a GST fusion vector in all three reading frames, and expression of the six fusion proteins was demonstrated.

Example 7

Reverse Recombination and Subcloning by Recombination

Figure 10A:
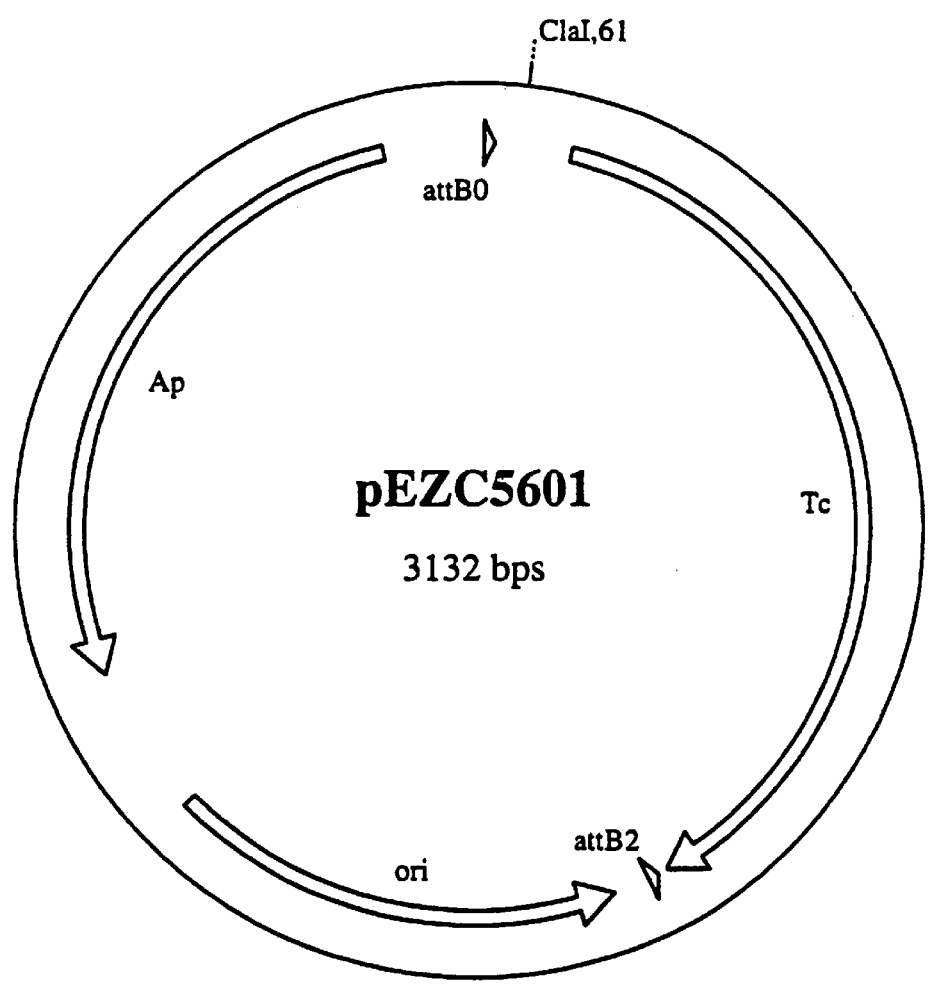
FIG. 10A depicts a vector diagram of pEZC5601.
Figure 10B:
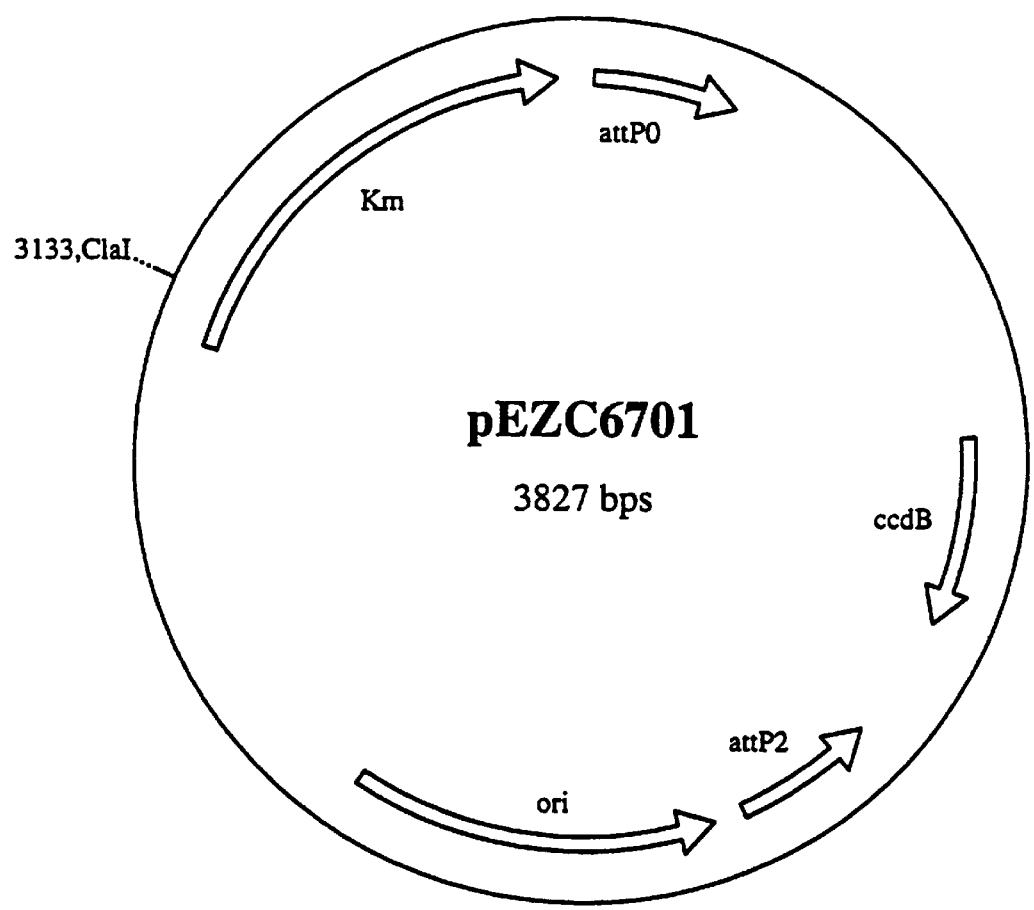
FIG. 10B depicts a vector diagram of pEZC6701.

Two plasmids were constructed to demonstrate reverse recombination according to the present invention. The vector pEZC5601 (FIG. 10A), containing attB recombination sites and termed the attB parent plasmid (this vector may correspond to the Product DNA), further contained an ampicillin resistance gene, an origin of replication, an attB2 site, a tetracycline resistance gene, and an attB0 site, as described above. Plasmid pEZC6701 (FIG. 10B), containing attP recombination sites and termed the attP parent plasmid (this vector may correspond to the Byproduct DNA or may correspond to a different Vector Donor DNA), also contained a kanamycin resistance gene, an origin of replication, an attP2 site, a gene encoding the toxic protein ccdB, and an attP0 site. Integrase buffer at 10×concentration comprised 0.25 M Tris HCl pH 7.5, 0.25 M Tris HCl pH 8.0, 0.7 M potassium chloride, 50 mM spermidine HCl, 5 mM EDTA, and 2.5 mg/ml BSA. Note that attP0 and attP2 contained the P1 and H1 domains. Integrase (1.5 μl of 435 ng/μl) and IHF (1.5 μl of 16 ng/μl in 1×Integrase buffer) were mixed with 13.5 μl of 1×Int buffer to make the recombinase mixture.

Two 8 μl reactions were assembled. Reaction A contained 300 ng pEZC6701 plasmid and 2 μl of recombinase mixture in 1×Integrase buffer. Reaction B contained 300 ng pEZC5601, 300 ng pEZC6701, and 2 μl of recombinase mixture in 1×Integrase buffer. Both reactions were incubated at 25° C. for 45 minutes, then at 70° C. for 5 minutes, and then cooled. TE buffer (792 μl of 10 mM Tris HCl pH 7.5, 1 mM EDTA) was added to each reaction, and 1 μl of this diluted reaction was transformed into DH5α UltraMax competent E. coli cells (Life Technologies, Inc., Rockville, Md.). After 1 hour of expression in non-selective medium, one tenth (100 μl) of each transformation was spread onto agar plates containing 100 μg/ml kanamycin.

After overnight incubation at 37° C., the plate from reaction A contained 1 colony, while the plate from reaction B contained 392 colonies. Twelve colonies were picked from the reaction B plate into rich liquid medium and grown overnight. Miniprep DNAs prepared from these cultures were run uncut on an agarose gel and all 12 contained a plasmid of about 3.8 kb. Six of the miniprep DNAs were cut with restriction enzyme ClaI and run along with pEZC6701 (the kanamycin resistant parental plasmid) also cut with ClaI. Plasmid pEZC6701 was cut once with ClaI to give a fragment of about 3.8 kb. The six miniprep DNAs cut twice with ClaI to give fragments of about 900 base pairs and about 2900 base pairs.

Figure 10C:
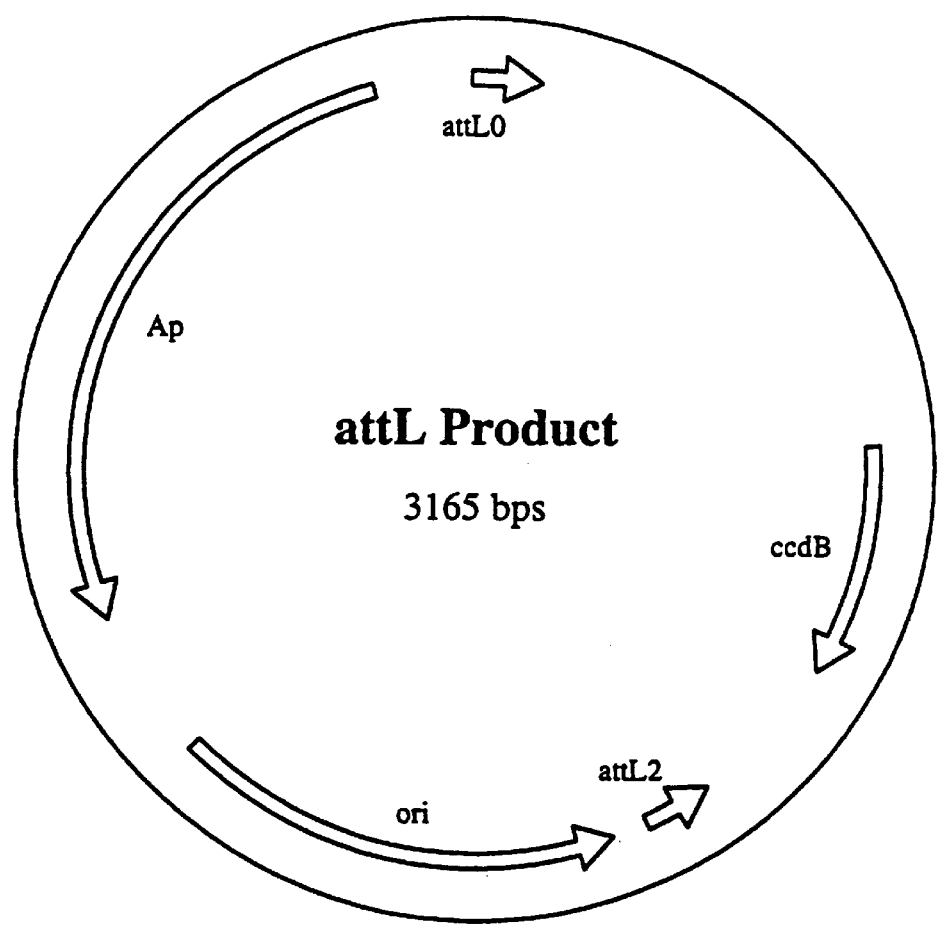
FIG. 10C depicts a vector diagram of attL product.
Figure 10D:
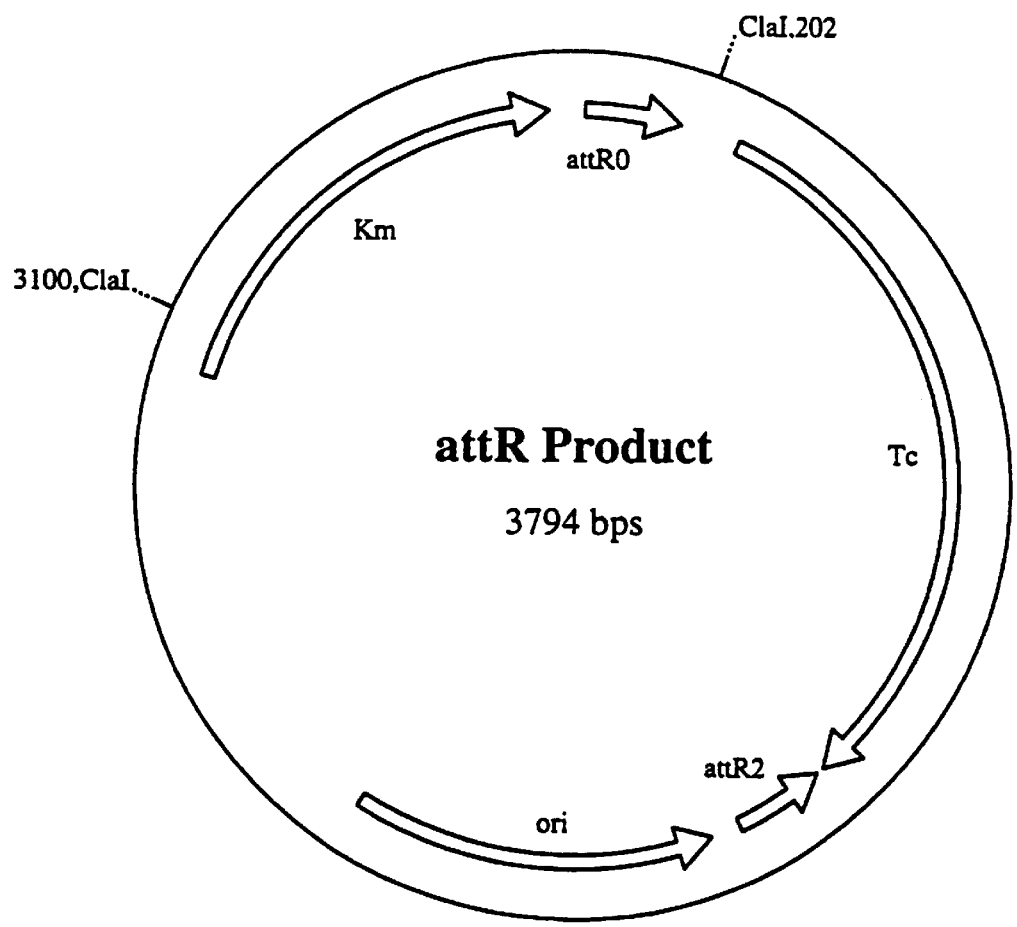
FIG. 10D depicts attR product.

Analysis: Recombination between the attP sites on pEZC6701 and the attB sites on pEZC5601 resulted in the production of two daughter plasmids, the attL product plasmid (FIG. 10C) (which may correspond to the Vector Donor DNA or a new Byproduct DNA) that contained the ampicillin resistance and ccdB genes, and the attR product plasmid (FIG. 10D) (which may also correspond to the Insert Donor DNA or a new Product DNA) that contained the kanamycin and tetracycline resistance genes. Competent E. coli cells that received the attL product plasmid, the attP parent plasmid pEZC6701, or recombination intermediates, were killed by the toxic ccdB gene product. Competent E. coli cells that received the aftB parent plasmid pEZC5601 were killed by the kanamycin selection. Only competent E. coli cells that received the desired attR product plasmid, comprising the kanamycin and tetracycline resistance genes, survived to form colonies. The success of the selection strategy was indicated by the large number of colonies from the reaction that contained both parental plasmids, compared to the reaction that contained only one parental plasmid. The reaction mechanism predicted that the desired product plasmid would contain two ClaI restriction sites, one in the kanamycin resistance gene from the pEZC6701 attP parent plasmid and one in the tetracycline resistance gene from the pEZC5601 attB parent plasmid. The presence of the two sites and the sizes of the fragments resulting from the ClaI digestion confirmed the reaction mechanism.

Thus, the present invention relates to reversal of the recombination reaction shown in FIG. 1, in which the Product DNA and Byproduct DNA may be combined to produce the Insert Donor DNA and the Vector Donor DNA.

Additionally, the invention provides for subcloning recombinations, in which a Product DNA (produced according to FIG. 1) may be combined with a new Vector Donor DNA to produce a new Product DNA (in a different Vector background) and a new Byproduct.

Example 8

Subcloning of Linearized Fragments

Figure 11A:
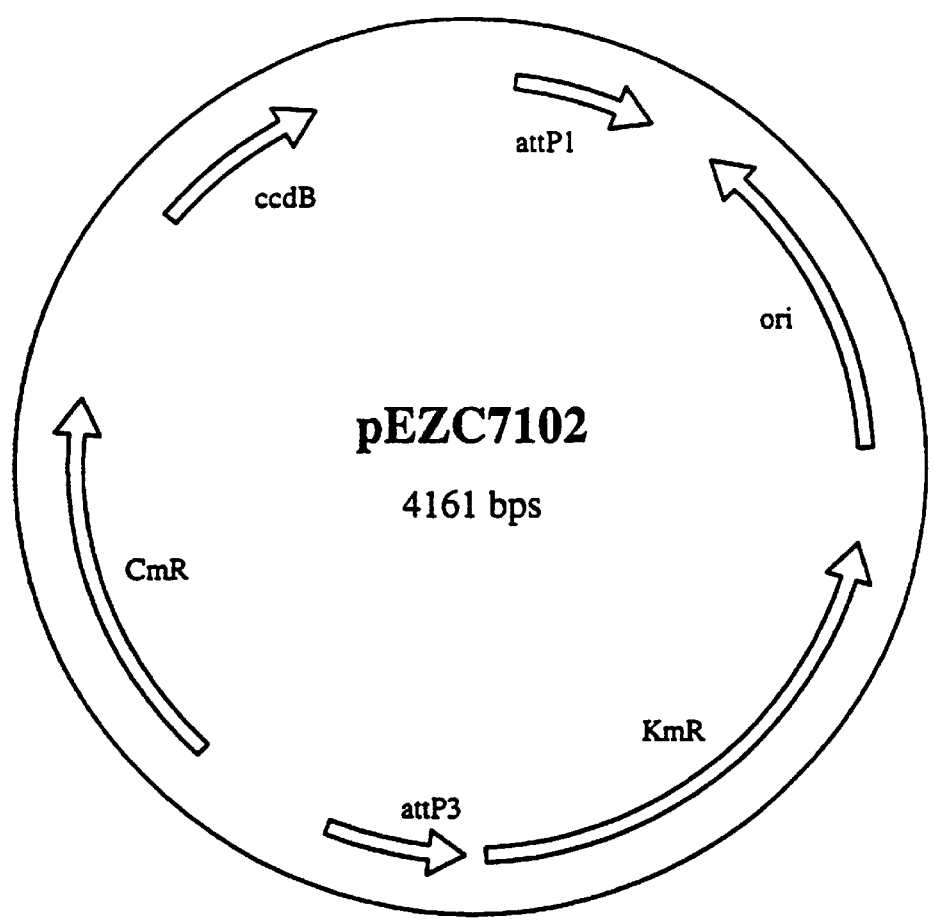
FIG. 11A depicts a vector diagram of pEZC7102.

Plasmid pEZC7102 (FIG. 11A), the attP parent plasmid (which may correspond to the Vector Donor DNA), contained segments attP1, origin of replication, kanamycin resistance, attP3, chloramphenicol resistance, and the toxic gene ccdB, and in the experiment described here was supercoiled. Plasmid pEZC7501 (FIG. 11B), the attB parent plasmid (which may correspond to the Insert Donor DNA or the Product DNA), contained the GFP gene cloned between attB1 and attB3 sites in a vector that comprised the functional domains of pCMVSPORT2.0 (Life Technologies, Inc.). The attP sites contained the P1 and H1 domains. Plasmid pEZC7501 was used uncut, or was linearized within the ampicillin resistance gene with ScaI, or was cut with XbaI and SalI, to yield a fragment comprising the SalI end, 22 bp, the attB1 site, the GFP gene, the attB3 site, and 14 bp to the XbaI end:

SalI end-22 bp-attB1-GFP-attB3-14 bp-XbaI end

Reactions (8 μl final volume) contained about 40 ng of each DNA, 1×Int buffer (25 mM Tris HCl pH 7.5, 25 mM Tris HCl pH 8.0, 70 mM KCl, 5 mM spermidine HCl, 0.5 mM EDTA, and 0.25 mg/ml BSA), 12.5% glycerol, 8 ng IHF, and 43 ng lambda integrase. Reactions were incubated at 25° C. for 45 minutes, then at 70° C. for 5 minutes, and then cooled. Duplicate 1 μl aliquots of each reaction were transformed into DH5α UltraMax cells and plated in duplicate on kanamycin agar plates.

The reaction that contained only (supercoiled) pEZC7102 gave an average of 2 colonies (range 1 to 4). The reaction that contained both pEZC7102 and supercoiled pEZC7501 gave an average of 612 colonies (range 482–762). The reaction that contained pEZC7102 and linear (ScaI-cut) pEZC7501 gave an average of 360 colonies (range 127–605). The reaction that contained pEZC7102 and the GFP gene on a fragment with attB sites and 22 bp and 14 bp beyond the attB sites (pEZC7501 cut with SalI and XbaI) gave an average of 274 colonies (range 243–308).

Miniprep DNAs were prepared from 4 colonies from the pEZC7102×supercoiled pEZC7510 reaction, and from 10 colonies from the pEZC7102×pEZC7501/SalI+XbaI reaction. All 14 DNAs were run uncut on an agarose gel, and the 10 DNAs from the pEZC7102×pEZC7501/SalI+XbaI reaction were cut with a mixture of NcoI and PstI and run on an agarose gel. All the uncut plasmids were about 2.8 kb in size. All ten plasmids cut with the mixture of NcoI and PstI gave fragments of about 700 and 2100 bp.

The results are presented in Table 8:

TABLE 8

| attP Parent | attB Parent | Colonies (average of 4 plates) | Minipreps done | Uncut product plasmid size | Fragment sizes, Nco + Pst digest |
|---|---|---|---|---|---|
| sc7102 | — | 2 | — | — | — |
| sc7102 | sc7501 | 612 | 4 | 2.8 kb | — |
| sc7102 | 7501/ScaI | 360 | — | — | — |
| sc7102 | 7501/SalI + XbaI | 274 | 10 | 2.8 kb | ca. 2100 bp, 700 bp |

Analysis: It was expected that the integrative reaction between the attB sites on plasmid pEZC7501 and the attP sites on plasmid pEZC7102 would produce the attL product plasmid (FIG. 11C) (corresponding to the Insert Donor DNA) containing the GFP segment from pEZC7501, and the kanamycin-origin segment from pEZC7102. The presence of the toxic gene ccdB on the attP parent plasmid pEZC7102 (corresponding to the Byproduct DNA) was predicted to kill all the cells that received this plasmid. The large increase in the number of colonies when pEZC7501 was present indicated that the desired reaction was occurring, and that the efficiency of the reaction was adequate even if the attB parent plasmid (corresponding to the Product DNA) was linear (ScaI cut), or if the attB sites and the GFP gene were present an a fragment that contained little additional sequence beyond the attB sites.

These results show that linear fragments can be suitably subcloned into a different vector by the method of the invention.

Example 9

Cloning Long PCR Fragments

A PCR product was designed to have an attB0 (wild type) site at one end and a loxP site at the other end. The rationale was that the attP0×attB0 reaction would go well with the attB0 molecule (the PCR product) linear, (since it involves a normal lambda integration reaction), and that the loxP×loxP excision from the cointegrate would also be efficient (the unimolecular excision reaction is efficient, the bimolecular integration reaction is inefficient with Cre).

Figure 9A:
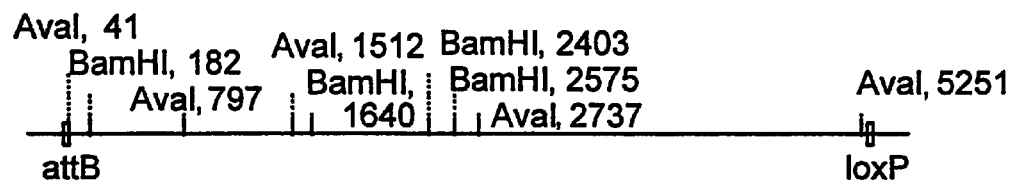
FIG. 9A depicts a diagram of 5.2 kb PCR prod.

The sequence of the attB-containing PCR primer was 5'-TCC GTT GAA GCC TGC TTT TTT ATA CTA ACT TGA GCG AAG CCT CGG GGT CAG CAT AAG G-3' (SEQ ID NO:31). The sequence of the loxP primer was 5'-CCA ATA ACT TCG TAT AGC ATA CAT TAT ACG AAG TTA TTG CCC CTT GGT GAC ATA CTC G-3' (SEQ ID NO:32). These primers amplify a part of the human myosin heavy chain. Polymerase chain reactions were performed using ELONGASE™ and K562 human DNA as template. Polymerase chain reactions were performed as follows. Reactions (50 microliters) contained 100 ng K562 human DNA (Life Technologies, Inc.), 0.2 μM of each primer, and 0.2 mM of each dNTP, in ELONGASE™ SuperMix (Life Technologies, Inc.). Reactions in thin wall tubes under mineral oil were denatured at 94° C. for 1 minute, then cycled 35 times at 94° C. for 30 seconds, 65° C. for 30 seconds, and 68° C. for 8 minutes 30 seconds. Following thermal cycling, reactions were maintained at 4° C. The 5.2 kb PCR product (FIG. 9A) was gel purified.

Figure 9B:
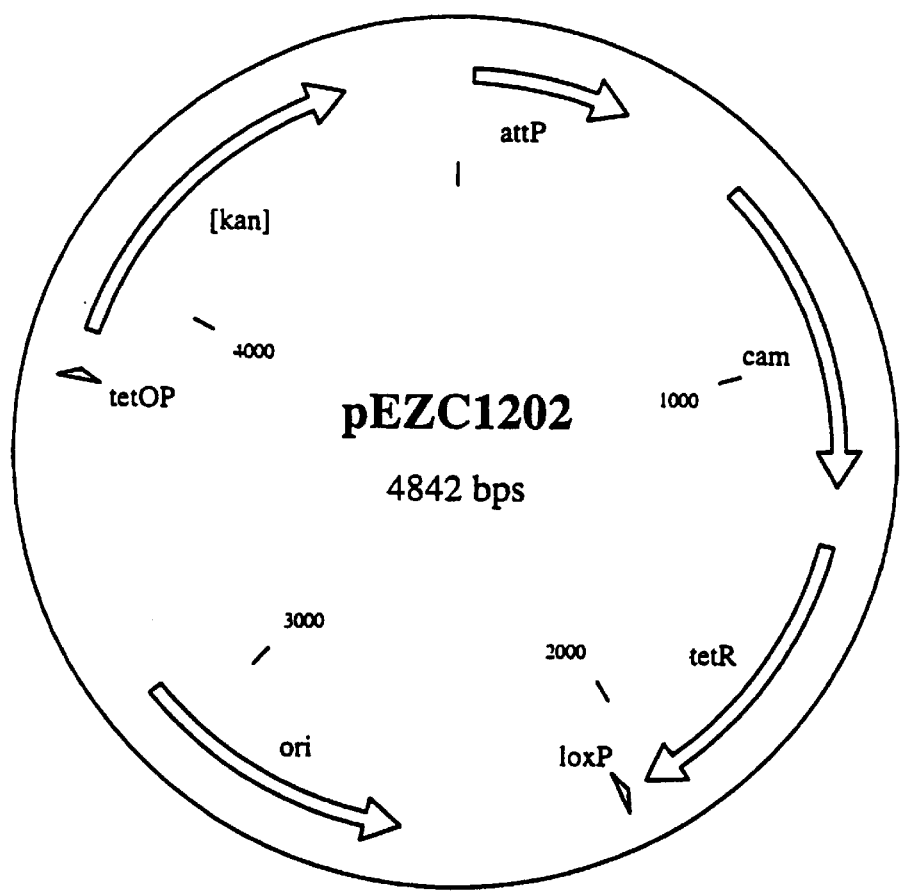
FIG. 9B depicts a vector diagram of pEZC1202.

Plasmid pEZC1202 (FIG. 9B) contained a wild-type attP site, a chloramphenicol resistance gene, a gene encoding the tet repressor, a wild-type loxP site, an origin of replication, and a tet operator/promoter transcribing and controlling the transcription of a kanamycin resistance gene. This plasmid conferred chloramphenicol resistance but not kanamycin resistance, because the tet repressor made by one element of the plasmid kept the kanamycin resistance gene turned off. The pEZC1202 DNA used in this experiment was a miniprep whose concentration was estimated to be about 50 ng per microliter.

About 40 ng of the gel purified 5.2 kb PCR product were included in a 10 μl reaction that contained about 50 ng of supercoiled pEZC1202, 0.2 units of Cre recombinase, 3.6 ng IHF, and 11 ng of Int in 50 mM Tris HCl pH about 7.8, 16 mM NaCl, 35 mM KCl, 0.25 mM EDTA, 0.375 mg/ml bovine serum albumin. A second reaction that did not contain the PCR product was included as a control. After incubating at 27° for 45 min and then 70° for 5 minutes, 1 μl aliquots were transformed into DH5α UltraMax competent E. coli cells (Life Technologies, Inc.). One fifth of each expression mix was plated on agar that contained 100 μg/ml kanamycin and the plates were incubated overnight at 37° C.

The reaction that contained the PCR product gave 34 colonies, while the reaction that lacked the PCR product gave 31 colonies. After the plates sat at room temperature for four days, 26 additional small colonies were seen on the plate from the positive (+PCR product) reaction, while only one additional small colony was seen on the plate from the negative (no PCR product) reaction.

Figure 9C:
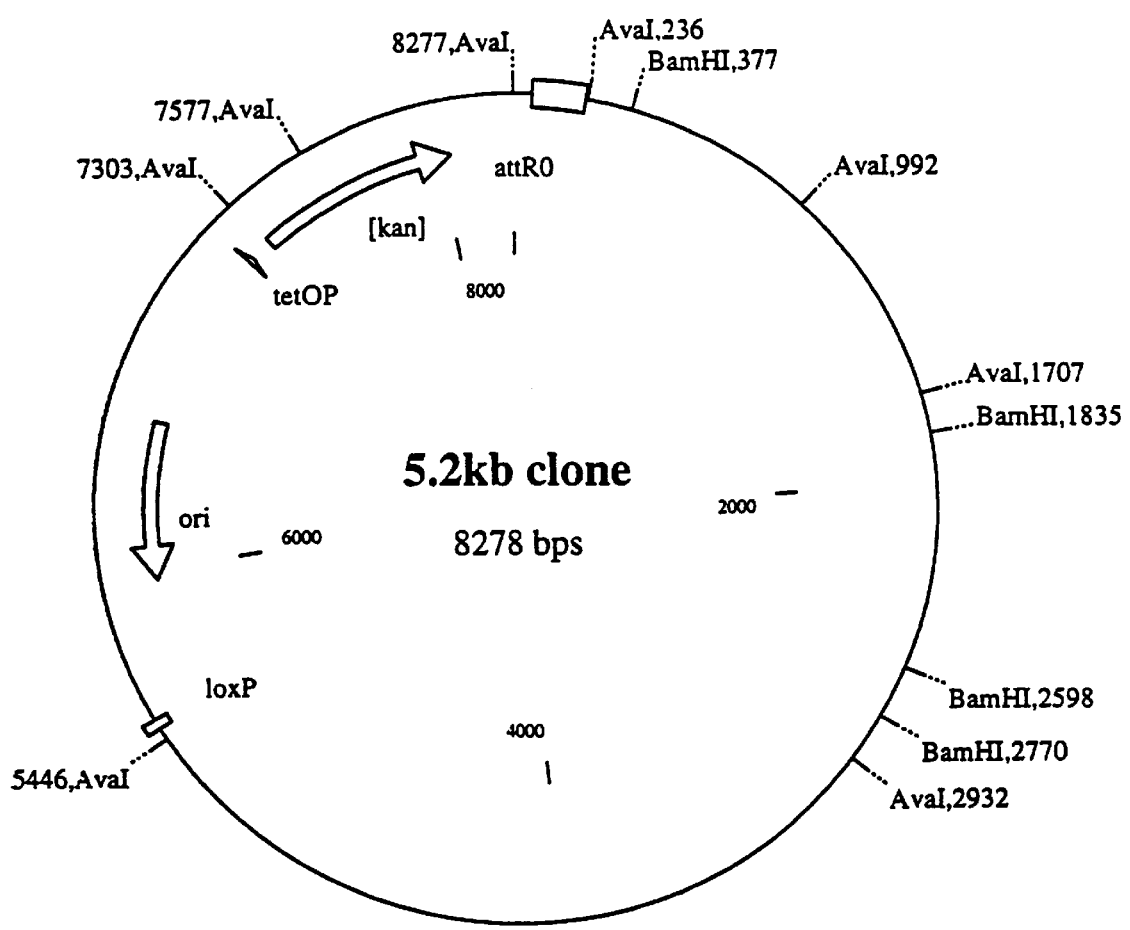
FIG. 9C depicts a vector diagram of 5.2 kb clone.

Twelve of the 26 small colonies were grown overnight in rich broth (CircleGrow) that contained 25 µg/ml kanamycin, and miniprep DNAs were prepared from these cultures. All twelve miniprep plasmids were about 8 kb in size, which corresponded to the size expected for replacement of the choramphenicol resistance and tet repressor genes in pEZC1202 with the 5.2 kb PCR product. The predicted recombinant product is shown in FIG. 9C. Two of these plasmids were cut with AvaI (8 sites predicted) and BamHI (4 sites predicted). All the predicted AvaI fragments appeared to be present. One of the BamHI sites predicted in the PCR product (the one closest to the attB end) was absent from both minipreps, but the other BamHI fragments were consistent with the expected structure of the cloned 5.2 kb PCR product.

Analysis: The replacement of the choramphenicol resistance and tet repressor genes in pEZC1202 with the 5.2 kb PCR product (part of the human myosin heavy chain) conferred a moderate resistance of the host *E. coli* cells to kanamycin, but this resistance was not sufficient to allow colonies to appear after overnight incubation. Thus, colonies containing the desired recombination product grew on kanamycin plates, but were not seen after overnight incubation, but only after an additional room temperature incubation. Of the 12 AvaI and BamHI restriction sites predicted from the nucleotide sequence, 11 were confirmed experimentally. Thus the following three observations support the conclusion that the 5.2 kb PCR product was cloned by recombination: (a) small, slow growing colonies appeared only on the plate from the reaction that contained the PCR product; (b) the miniprep plasmids from these colonies were the expected size; and (c) diagnostic restriction cuts gave the expected fragments (with the one above noted exception).

Example 10

Cloning of PCR Fragments

Three sets of pairs of PCR primers (Table 9) were designed to amplify an 830 bp sequence within plasmid pEZC7501 (FIG. 11B) comprising: attB1-GFP-attB3, with or without additional nucleotides at the outer ends of the 25 bp attB1 and attB3 recombination sites. (Here "outer" refers to the end of the attB sequence that is not adjacent to the GFP gene sequence.) Primer set A added 17 nucleotides upstream of attB1 and 15 nucleotides downstream of attB3; primer set B added 5 and 8 nucleotides to attB1 and attB3, respectively; and primer set C added no additional nucleotides to either attB recombination sequence.

The primer sequences are provided in Table 9:

TABLE 9

|  |  |  |
| --- | --- | --- |
|  |  | (SEQ ID NO:33) |
| upper GFP A | 5'-TCA CTA GTC GGC GGC CCA CA |  |
|  |  | (SEQ ID NO:34) |
| lower GFP A | 5'-GAG CGG CCC CCG CGG ACC AC |  |
|  |  | (SEQ ID NO:35) |
| upper GFP B | 5'-GGC CCA CAA GTT TGT ACA AAA |  |
|  |  | (SEQ ID NO:36) |
| lower GFP B | 5'-CCC CGC GGA CCA CTT TGT AC |  |

TABLE 9-continued

|  |  |  |
| --- | --- | --- |
|  |  | (SEQ ID NO:37) |
| upper GFP C | 5'-ACA AGT TTG TAC AAA AAA GCA |  |
|  |  | (SEQ ID NO:38) |
| lower GFP C | 5'-ACC ACT TTG TAC AAG AAA GCT |  |

PCR Reactions

Primer sets A and C were used first with the following PCR reactions, in 50 µl, in duplicate. Final concentrations were:

20 mM TrisHCl, pH 8.4

50 mM KCl 0.2 mM of all four deoxynucleotide triphosphates (dNTPs)

400 ng/ml pEZC7501 supercoiled DNA template 0.5 µM of each primer

Recombinant Taq DNA polymerase (BRL-GIBCO) 100 U/ml

A duplicate set of the above reactions contained 1 M betaine.

The reactions were first heated for to 94° C. for 1', then cycled 25 times at 94° C. for 45", 55° C. for 30", and 72° C. for 1'.

The size of the PCR reaction products was analyzed on a 1% agarose gel in TAE buffer containing 0.5 µg/ml ethidium bromide. All reactions yielded products of the expected size, thus duplicate reactions were pooled. As the corresponding reactions with and without betaine were not significantly different, these also were pooled, giving a final pooled volume for reactions with primer sets A and C of 200 µl each.

Primer set B was then used with identical reactions to those above performed, except that the reaction volumes were increased to 100 µl. After duplicate reactions and reactions plus and minus betaine were pooled, the final volume of the reactions with primer set B was 400 µl.

The three pooled primer reaction products were stored at −20° C. for 4 weeks.

PCR Product Purification

Each of the three pooled PCR products was extracted once with an equal volume of a mixture of Tris-buffered phenol, isoamyl alcohol and chloroform. The aqueous supernatant then was extracted twice with an equal volume of isobutanol, and the aqueous layer ethanol precipitated with two volumes of ethanol, 0.1 M sodium acetate, pH 6.2. The ethanol precipitates were recovered by centrifugation at 13,000 rpm for 10' at room temperature, and the supernatant discarded. The dried pellets were dissolved in TE: 100 µl for reactions prepared with primer sets A and C; 200 µl for the reactions with primer set B.

To remove PCR primers and extraneous small PCR products, the PCR products were precipitated with polyethylene glycol (PEG) by adding ½ volume of a solution of 30% PEG 8000 (Sigma), 30 mM MgCl₂, mixing well, and centrifuging at 13,000 rpm for 10', all at room temperature. The supernatant was discarded, and the pellets were dissolved in their previous volume of TE buffer. 1 µl aliquots of each of the three PCR products were checked on a 1% agarose gel to quantitate the recovery, which was estimated to be over 90%. The concentration of each PCR product was adjusted using TE to 40 ng/µl.

Recombination Reaction with the PCR Products of Primer sets A, B, and C

Five 8 µl reactions were assembled in 1×Integrase buffer (25 mM Tris HCl pH 7.5, 25 mM Tris HCl pH 8.0, 80 mM KCl, 5 mM spermidine, 0.5 mM EDTA, 0.25 mg/ml BSA) containing: 40 ng of pEZC7102 DNA, 2 μl of recombinase mixture (8 ng/μl IHF, 22 ng/μl Int in 1×Int Buffer, 50% glycerol) the reactions differed by the addition of either the PCR product of primer set A (reaction A), primer set B (reaction B), or primer set C (reaction C); the addition of no PCR product (reaction D), or the addition of 40 ng of pEZC7501 SC (supercoiled) DNA(reaction E) as a positive control. All reactions were performed in duplicate.

The reactions were incubated for 45' at 25° C., for 10' at 70° C., then held at 0–5° C. 2 μl aliquots of each reaction were transformed into Max Efficiency DH5α, in a 50 μl transformation reaction, and following expression in 50° C. medium, ⅕ (100 μl) and ⅘ (400 μl) of the reactions were plated on kanamycin-containing (50 μg/ml) LB culture plates. The results of the duplicate reactions are shown in Table 10.

TABLE 10

| Transfection | No. Colonies |
|---|---|
| A 100 μl | 464, 668 |
| A 400 μl | >1000, >1300 |
| B 100 μl | 980, 1292 |
| B 400 μl | >3000, >3000 |
| C 100 μl | 2, 8 |
| C 400 μl | 13, 20 |
| D 100 μl | 0, 0 |
| D 400 μl | 0, 0 |
| E 100 μl | 56, 70 |

Analysis of the Colonies Obtained

Miniprep DNA was prepared from 8 colonies of each of the Recombination reactions with primer sets A, B. or C. The supercoiled DNA obtained was analyzed on a 1% agarose gel: all eight of colonies from the recombination products of primer sets A and B were of the predicted size (2791 bp) for correct recombination between the PCR products (about 824 bp) and the attB1-ori-kan'-attB3 sequence donated by pEZC7102 (1967 bp). Three of the eight reaction products of primer set C were of the predicted size; the other five all were slightly larger than 4 kb.

Further analysis of the reaction products was performed using two different restriction enzymes, AvaI and PvuII, each of which cleaves twice (but at different locations) within the predicted recombinant product, once within the PCR product sequence and once within the sequence contributed by pEZC7102. Both of these enzymes should cleave the intact pEZC7102 recombination partner plasmid at two sites, to give fragments easily distinguished from those of the expected recombination products.

The two restriction enzyme digests yielded the expected sizes of fragments (2373 and 430 bp for AvaI; 2473 and 330 bp for PvuII) from the colonies generated from the recombination reactions with primer sets A and B, as well as for the three colonies from primer set C that displayed the expected size of supercoiled DNA. For the other five colonies from primer set C that yielded larger SC DNA, however, the PvuII digest revealed fragments of approximate size to those predicted from a digestion of pEZC7102, whereas the AvaI digest revealed only a single fragment, approximately the size of linearized pEZC7102 (4161 bp).

Analysis

These results indicate that PCR products generated from templates containing a gene flanked by attB sites can serve as efficient substrates for the reverse recombination reaction. The addition of even short DNA sequences to the ends of the attB1 and attB3 sites or core regions (e.g., 5 bp and 8 bp, respectively, in primer set B) stimulated this reaction by 100 fold or more. Surprisingly, reverse recombination reactions with PCR products containing additional sequence beyond the attB sites appeared in these reactions to be more efficient recombination partners than the supercoiled positive control plasmid, pEZC7501.

All the recombination products were generated faithfully. A low level of background colonies emerged from the relatively inefficient recombination reactions with primer set C, which lacked additional sequence beyond the 25 bp attB sites. This background appeared to be due to a largely intact pEZC7102 (which encodes kanamycin resistance) lacking an active ccdB death gene, allowing it to survive. Consistent with this interpretation is that one of the two restriction sites for AvaI in this plasmid was also altered. One of the AvaI sites is present within the ccdB region of pEZC7102. It is likely therefore that the alteration of this site was secondary to mutational inactivation of the ccdB gene.

Example 11

Further Cloning of PCR Fragments

Two sets of 6 primers for preparing PCR products from the plasmid pBR322 as template were used. One set (Table 11) anneals to sequences flanking the TetR gene, including the TetR promoter. The other set (Table 12) anneals to sequences flanking the AmpR gene, including its promoter. The "tet" and "amp" primers used contain no attB sequences, only sequences inherent to the pBR322 plasmid; the "attB" primers contain, in addition to the pBR322 sequences, the 25 bp of attB 1 or attB3 sequences; the "attB+4" primers contain the pBR322-specific sequences, plus the 25 bp attB 1 or attB3 sequences, each with four Gs at the outer end. (Here "outer" refers to the end of the attB sequence not adjacent to the template-specific primer sequence.)

Preparation of pBR322 Template

To improve the efficiency of the PCR reaction, the supercoiled pBR322 DNA was linearized by incubating 3.5 μg of Suerpcoiled (SC) pBR322 DNA in a 200 μl reaction with 15 units of the restriction enzyme NdeI and final concentration of 50 mM Tris-HCl, pH8.0, 10 mM MgCl$_2$, and 50 mM NaCl, for one hour at 37° C.

The digested pBR322 DNA was extracted once with phenol, isoamyl alcohol, and chloroform, extracted twice with isobutanol, and precipitated by adding two volumes of ethanol plus 0.15 M sodium acetate. The precipitate was washed once with 100% ethanol, dried, then dissolved in TE buffer. Recovery of DNA, quantitated on a 1% agarose gel in TAE buffer, 0.5 μg/ml ethdium bromide, was estimated as greater than 80%.

TABLE 11

| tet Primer | Primer Sequence | SEQ ID NO: |
|---|---|---|
| tet-L | AAT TCT CAT GTT TGA CAG CTT ATC | 48 |
| tet-R | CGA TGG ATA RTGT TCT GCC AGG | 49 |
| attB1 - tetL | ACAAG TTTGTA CAAAAA AGCA GGCT-<br>AAT TCT CAT GTT TGA CAG CTT ATC | 50<br>50 |
| attB3 - tetR | ACCAC TTTGTA CAAGAA AGCT GGGT-<br>CGA TGG ATA TGT TCT GCC AAG | 51 |

TABLE 11-continued

| tet Primer | Primer Sequence | SEQ ID NO: |
|---|---|---|
| attB1 + 4-tetL | GGGG ACAAG TTTGTA CAAAAA AGCA-GGCT AAT TCT CAT GTT TGA CAG CTT-ATC | 52 |
| attB3 + 4-tetR | GGGG ACCAC TTTGTA CAAGAA AGCT-GGGT CGA TGG ATA TGT TCT GCC AAG | 53 |

TABLE 12

| amp Primer | Primer Sequence | SEQ ID NO: |
|---|---|---|
| amp-L | AAT ACA TTC AAA TAT GTA TCC GC | 54 |
| amp-R | TTA CCA ATG CTT AAT CAG TGA G | 55 |
| attB1 − ampL | ACAAG TTTGTA CAAAAA AGCA GGCT-AAT ACA TTC AAA TAT GTA TCC GC | 56 |
| attB3 − ampR | ACCAC TTTGTA CAAGAA AGCT GGGT-TTA CCA ATG CTT AAT CAG TGA G | 57 |
| attB1 + 4-ampL | GGGG ACAAG TTTGTA CAAAAA AGCA-GGCT AAT ACA TTC AAA TAT GTA TCC-GC | 58 |
| attB3 + 4-ampR | GGGG ACCAC TTTGTA CAAGAA AGCT-GGGT TTA CCA ATG GTT AAT CAG TGAG | 59 |

PCR Amplification of Tet and Amp Gene Sequences

Six PCR reactions were performed, in 100 μl, consisting of 20 mM Tris-HCl, pH 8.4, 50 mM KCl, 1.5 mM MgCl$_2$, 0.2 mM dNTPs, 2 ng linearized pBR322, 2.5 units of Taq DNA polymerase (GIBCO-BRL), and 0.5 uM of each pair of PCR primers listed in Tables 3 and 4. The reactions were first heated to 94° C. for 3'; then subjected to 25 cycles of 94° C. for 45 seconds, 55° C. for 30 seconds, and 72° C. for 1 minute. Based on 1% agarose gel analysis, all the reactions generated products of the expected size, in reasonable yields.

Purification of PCR Products

The products from duplicate reactions were pooled; extracted with an equal volume of phenol, isoamyl alcohol, and chloroform; extracted twice with an equal volume of isobutanol; and precipitated with two volumes of ethanol, as above. The six precipitates were washed once with 100% ethanol, dried and dissolved in 100 μl TE. 1 μl aliquots were taken for gel analysis of the product before PEG precipitation.

To each tube was added 50 μl of 30% PEG 8000, 30 mM MgCl$_2$. The solution was mixed well and centrifuged at 13,000 rpm for 10', at room temperature. The supernatant was carefully removed, and the precipitate dissolved in 100 μl TE. Recovery was quantitated on a 1% agarose and estimated to be over 90%. The gel analysis also revealed that nucleic acid products smaller than about 300 nucleotides had been effectively removed by the PEG precipitation step.

Recombination Reactions

Figure 11B:
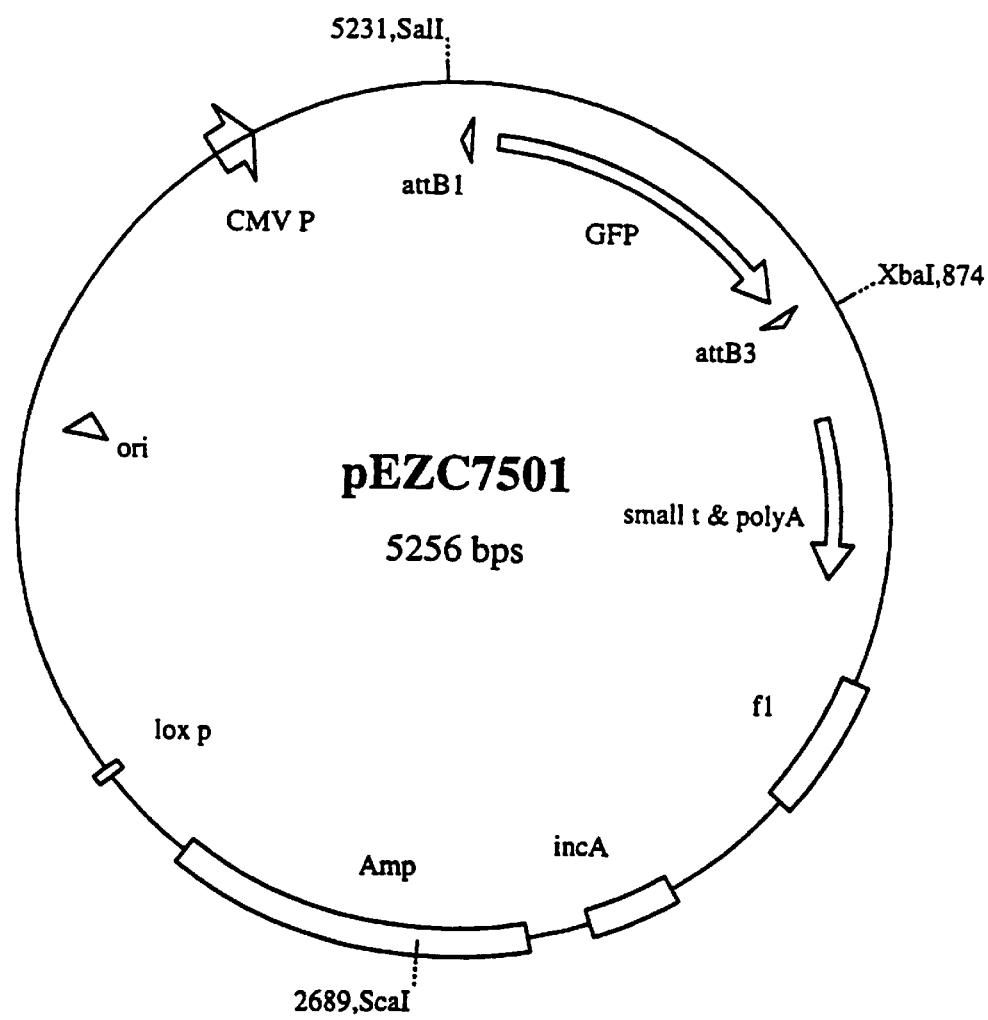
FIG. 11B depicts a vector diagram of pEZC7510.
Figure 11C:
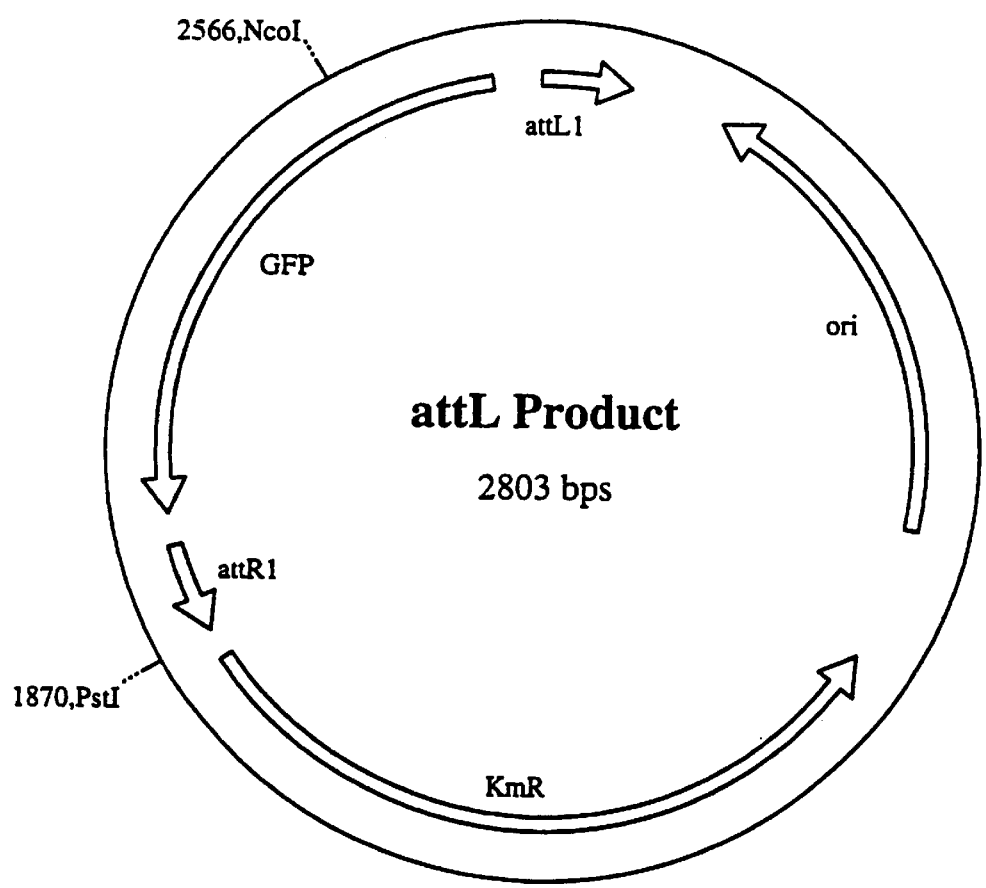
FIG. 11C depicts the attL product.
Figure 12A:
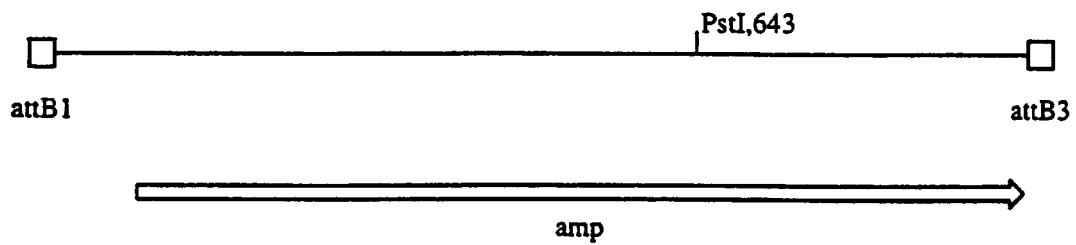
FIG. 12A depicts an amp PCR product with terminal attB sites.
Figure 12B:
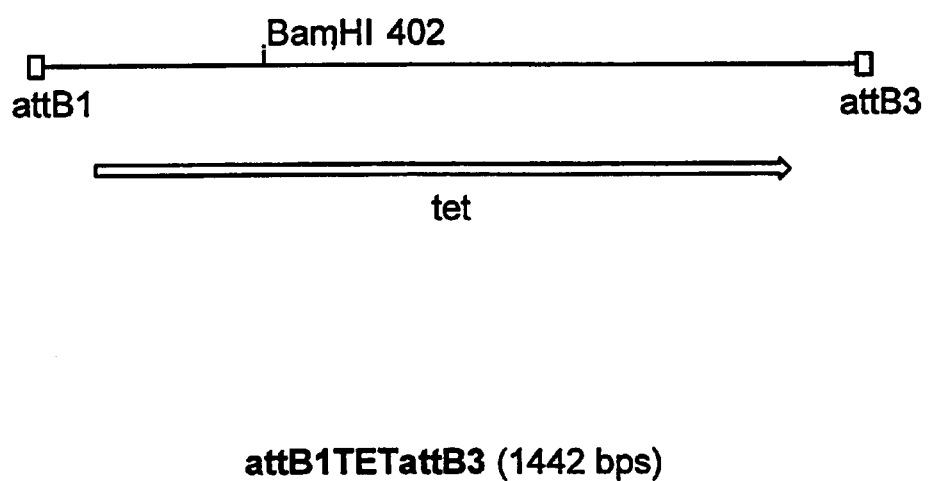
FIG. 12B depicts a tet PCR product with terminal attB sites.

Seven recombination reactions were performed, each in a total volume of 8 μl, containing 1×integrase buffer, 40 ng pEZC7102 (FIG. 11A), and 2 μl recombinase mixture (see above, Example 10). Each of the reactions also contained approximately 40 ng of one of the six above PCR products or, as a positive control, 40 ng of pEZC7501 (FIG. 11B). The amp and tet PCR products with attB sites at their termini are shown in FIGS. 12A and 12B. The reactions were incubated at 25° C. for 45', at 70° C. for 10', then held at 0–5° C. for 1–2 hours until used to transform E. coli.

E. coli Transformation with Recombination Reaction Products

1 μl of each of the recombination reactions was transformed into Max Efficiency DH5α in a 50 μl transformation reaction, and following expression in SOC medium, ⅕ (100 μl) and ⅘ (400 μl) of each reaction were plated on culture plates containing 50 μg/ml kanamycin. The plates were incubated overnight and colonies were counted. The number of colonies obtained from each set of duplicate reactions are displayed in Table 13:

TABLE 13

| Recombination Reactions | No. Colonies |
|---|---|
| tet 100 (100 μl) | 6, 10 |
| tet 400 (400 μl) | 27, 32 |
| attB − tet 100 | 9, 6 |
| attB − tet 400 | 27, 36 |
| attB + 4 − tet 100 | 824, 1064 |
| attB + 4 − tet 400 | >2000, >4000 |
| amp 100 | 7, 13 |
| amp 400 | 59, 65 |
| attB − amp 100 | 18, 22 |
| attB − amp 400 | 66, 66 |
| attB + 4 − amp 100 | 3020, 3540 |
| attB + 4 − amp 400 | >5000, >5000 |
| pEZC7501 100 | 320, 394 |
| pEZC7501 400 | 1188, 1400 |

Analysis of the Colonies Obtained

As a rapid phenotypic screen, 10 of the colonies from the tet EZC reactions and 33 of the colonies from the attB+4-tet EZC reactions were streaked onto an LB culture plate containing tetracycline (15 μg/ml). As a control for the potency of the tetracycline, 3 colonies of pUC19-transformed cells, lacking a TetR gene, were also streaked onto the plate. All colonies from the attB+4-tet EZC reactions grew well; colonies from the tet EZC reactions grew only very slightly, and the pUC19 colonies grew not at all.

Analogous results were obtained by streaking colonies from the amp PCR reactions on culture plates containing ampicillin (100 ug/ml ). All 21 colonies generated from the attB+4-amp recombination reactions grew well, whereas only one of 13 colonies from the attB-amp reactions grew in the presence of ampicillin. No growth was seen with any of the 15 colonies from the recombination reaction with amp PCR products.

Figure 12C:
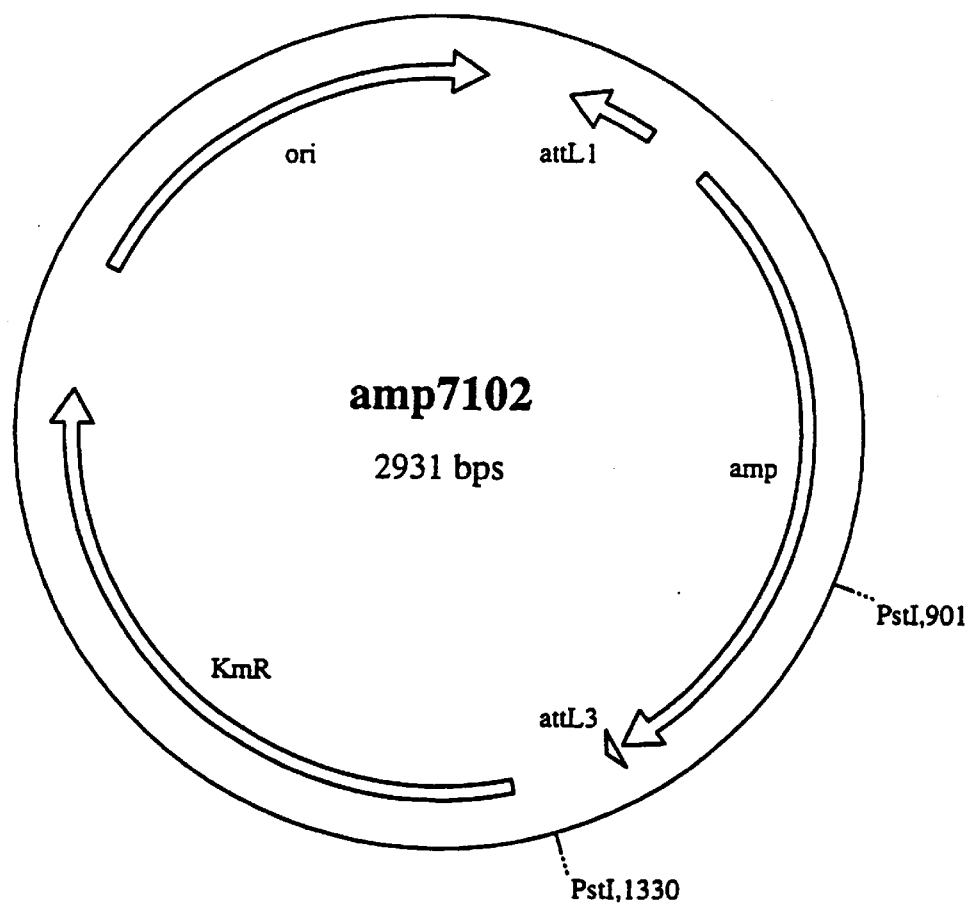
FIG. 12C depicts a restriction map of amp7102.
Figure 12D:
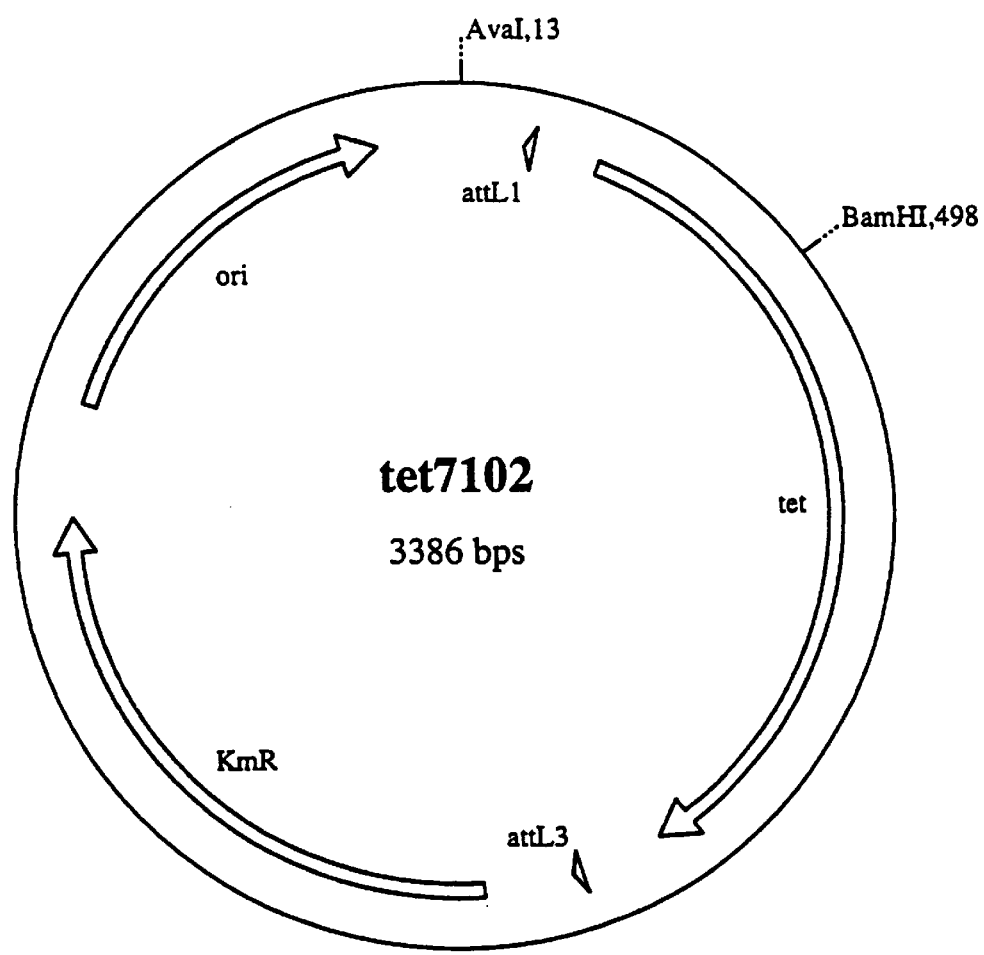
FIG. 12D depicts a restriction map of tet 7102.

To characterize plasmid DNA, eight colonies generated from the six EZC reactions with PCR products were picked into LB broth containing 50 μg/ml kanamycin and grown overnight at 37° C. Miniprep DNA was prepared from 0.9 ml of each culture, and the size of the supercoiled DNA was analyzed on a 1% agarose gel in TAE buffer containing 0.5 μg/ml ethidium bromide. The results are displayed in Table 14. The predicted structures of the recombination products are shown in FIGS. 12C and 12D.

TABLE 14

| Recombination Reactions | DNA | Predicted Size (bp) | Number with Predicted Size |
|---|---|---|---|
| tet | SC (supercoiled) | 3386 | 0/8 |
| attB − tet | SC | 3386 | 1/8 |
| attB + 4 − tet | SC | 3386 | 7/7 |

TABLE 14-continued

| Recombination Reactions | DNA | Predicted Size (bp) | Number with Predicted Size |
|---|---|---|---|
|  | AvaI + Bam | 485, 2901 | 3/3 |
| amp | SC | 2931 | 0/8 |
| attB − amp | SC | 2931 | 3/8 |
| attB + 4 − amp | SC | 2931 | 8/8 |
|  | Pst | 429, 2502 | 3/3 |

Analysis

These results, based on the amplification of two different gene sequences, tet and amp, within the plasmid pBR322 clearly demonstrate that PCR products generated using primers containing the 25 bp attB1 and attB3 recombination sequence serve as highly efficient substrates for the recombination reaction. Addition of a short sequence to the outside of each 25 bp attB site stimulates the recombination reaction by over 100 fold, as also observed in the experiments of Example 10. Also similar to Example 10, the efficiency of the recombination reactions using linear PCR products with attB sites exceeded the efficiency obtained with the positive control SC DNA plasmid, pEZC7501.

Further, a high percentage of the reaction products are as predicted, since all 33 colonies tested from the attB+4-tet reactions displayed functional tetracycline resistance, and all 21 of the colonies from the attB+4-amp reactions displayed ampicillin resistance. All 16 of the miniprep DNAs, examined from the recombination reactions of either attB+4-tet or attB+4-amp PCR products with pEZC7102, generated supercoiled DNA and restriction digest fragments of the correct sizes.

Example 12
Use of Topoisomerase to Stimulate Recombination

The stimulation of the recombination reaction by making one or the parental plasmids linear was not expected. If the stimulation resulted from relief of some conformation constraint arising during the two recombination reactions (formation of the Cointegrate and resolution to the two daughter molecules), then unwinding of the plasmids with a topoisomerase might also be stimulatory when one or both parental plasmids were circular.

The Insert Donor was pEZC2901 (FIG. 7A), and the Vector Donor was pECZ3101 (FIG. 7B). A portion of pEZC3101 was linearized with Mlu I. 20 ng of pEZC2901 and/or pECZ3101 were used in each 10 µl reaction (29 ng Int, 2.9 ng Xis, 5.4 ng IHF in 50 mM Tris HCl pH about 7.8, 16.5 mM NaCl, 35 mM KCl, 5 mM spermidine, 0.375 mg/ml BSA, 0.25 mM EDTA, 2% glycerol). Topoesomerse I (from calf Thymus; Life Technologies, Inc.) was diluted from 15 units/µl to the concentrations indicated in Table 15 in 1×EZC buffer.

TABLE 15

|  | 1 | 2 | 3 | 4 | 5 | 6 | 7 | 8 | 9 | 10 |
|---|---|---|---|---|---|---|---|---|---|---|
| Circular 3101 |  |  |  |  |  | 2 | 2 | 2 | 2 | 2 |
| Linear 3101 | 2 | 2 | 2 | 2 | 2 |  |  |  |  |  |
| Circular 2901 |  | 2 | 2 | 2 | 2 |  | 2 | 2 | 2 | 2 |
| Recombinase | 2 | 2 | 2 | 2 | 2 | 2 | 2 | 2 | 2 | 2 |
| TE | 2 |  |  |  |  | 2 |  |  |  |  |
| Topoisomerase, 1:60 |  |  | 2 |  |  |  |  | 2 |  |  |
| Topoisomerase, 1:20 |  |  |  | 2 |  |  |  |  | 2 |  |
| Topoisomerase, 1:6 |  |  |  |  | 2 |  |  |  |  | 2 |
| 3 X Buffer | 2 | 2 | 2 | 2 | 2 | 2 | 2 | 2 | 2 | 2 |
| 1 X Buffer | 2 | 2 |  |  |  | 2 | 2 |  |  |  |

These reactions were assembled in the following order: buffer; TE; DNAs; Clonase; Topoisomerase. The reactions were incubated at 22°–28° for 45 minutes, then at 70° for 5 minutes. 1 µl aliquots were transformed into UltraMax DH5α competent E. coli (Life Technologies, Inc.). Following expression, aliquots were plated on 100 µg/ml kanamycin and incubated at 30° for 48 hours. Results: see Table 16.

TABLE 16

| Reaction # | Colonies | Vector Donor | Insert Donor | Recombinase | Topoisomerase |
|---|---|---|---|---|---|
| 1 | 0 | linear 3101 | — | + | — |
| 2 | 245 | linear 3101 | circular 2901 | + | — |
| 3 | 221 | linear 3101 | circular 2901 | + | 0.5 units |
| 4 | 290 | linear 3101 | circular 2901 | + | 1.6 units |
| 5 | 355 | linear 3101 | circular 2901 | + | 5 units |
| 6 | 0 | circular 3101 |  | + | — |
| 7 | 23 | circular 3101 | circular 2901 | + | — |
| 8 | 209 | circular 3101 | circular 2901 | + | 0.5 units |
| 9 | 119 | circular 3101 | circular 2901 | + | 1.6 units |
| 10 | 195 | circular 3101 | circular 2901 | + | 5 units |

Analysis

Linearizing the Vector Donor increased the number of colonies about 10 fold (reaction 2 vs. reaction 7). Addition of 0.5 to 5 units of topoisomerase I to reactions containing circular Insert Donor and linear Vector Donor had little or no effect on the number of colonies (reaction 2 compared to reactions 3, 4, and 5; maximum 1.4 fold). In contrast, if both parental plasmids were circular (reaction 7–10), the addition of topoisomerase stimulated the number of colonies 5 to 9 fold. Thus addition of topoisomerase I to reactions in which both parental plasmids were circular stimulated the recombination reactions nearly as much as linearizing the Vector Donor parent. Topoisomerase I was active when used in combination with the three recombination proteins, in recombination buffer. The addition of topoisomerase I to the recombination reaction relieves the necessity to linearize the Vector Donor to achieve stimulation of the recombination reactions.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for cloning or subcloning desired nucleic acid molecules comprising
   a) combining in vitro or in vivo
      i) one or more Insert Donor molecules comprising one or more nucleic acid segments flanked by two or more recombination sites, wherein said recombination sites do not substantially recombine with each other;
      ii) two or more different Vector Donor molecules, each comprising two or more recombination sites, wherein said recombination sites do not substantially recombine with each other; and
      iii) one or more site specific recombination proteins; and
   b) incubating the combination under conditions sufficient to transfer one or more of said nucleic acid segments into said different Vector Donor molecules, thereby producing two or more different Product molecules.

2. The method of claim 1, wherein said Insert Donor molecules are obtained from genomic DNA.

3. The method of claim 1, wherein said Insert Donor molecules are obtained from cDNA.

4. The method of claim 1, wherein said Insert Donor molecules are produced by chemical synthesis.

5. The method of claim 1, wherein said Vector Donor molecules comprise at least one Selectable marker.

6. The method of claim 5, wherein the Selectable marker comprises at least one DNA segment selected from the group consisting of:
   (a) a DNA segment that encodes a product that provides resistance in a recipient cell against otherwise toxic compounds;
   (b) a DNA segment that encodes a product that is otherwise lacking in a recipient cell;
   (c) a DNA segment that encodes a product that suppresses the activity of a gene product in a recipient cell;
   (d) a DNA segment that encodes a product that can be identified;
   (e) a DNA segment that encodes a product that inhibits a cell function in a recipient cell;
   (f) a DNA segment that inhibits the activity of any of the DNA segments of (a)–(e) above;
   (g) a DNA segment that binds a product that modifies a substrate;
   (h) a DNA segment that encodes a specific nucleotide recognition sequence which can be recognized by a protein, an RNA, DNA or chemical,
   (i) a DNA segment that, when deleted, directly or indirectly confers sensitivity to cell killing by particular compounds within a recipient cell;
   (j) a DNA segment that encodes a product that is toxic in a recipient cell; and
   (k) a DNA segment that can be used to isolate or identify a desired molecule.

7. The method of claim 6, wherein said Selectable marker comprises at least one marker selected from the group consisting of an antibiotic resistance gene, a tRNA gene, an auxotrophic marker, a toxic gene, a phenotypic marker, an antisense oligonucleotide, a restriction endonuclease, a restriction endonuclease cleavage site, an enzyme cleavage site, a protein binding site, and a sequence complementary to a PCR primer sequence.

8. The method of claim 1, wherein said Vector Donor molecules comprise prokaryotic and/or eukaryotic vectors.

9. The method of claim 8, wherein said eukaryotic vectors comprise vectors which replicate in yeast cells, plant cells, fish cells, eukaryotic cells, mammalian cells, or insect cells.

10. The method of claim 8, wherein said prokaryotic vectors comprise vectors which replicate in gram negative or gram positive bacteria.

11. The method of claim 10, wherein said prokaryotic vectors comprise vectors which replicate in bacteria of the genus Escherichia, Salmonella, Bacillus, Streptomyces or Pseudemonas.

12. The method of claim 11, wherein said prokaryotic vector comprises a vector which replicates in *E. coli*.

13. The method of claim 8, wherein said Vector Donor molecules are selected from the group consisting of cloning vectors, sequencing vectors, expression vectors, fusion vectors, 2-hybrid vectors, and reverse 2-hybrid vectors.

14. The method of claim 8, wherein said eukaryotic vectors are selected from the group consisting of pFastBac, pFastBac HT, pFastBac DUAL, pSFV, pTet-Splice, pEUK-C1, pPUR, pMAM, pMAMneo, pBI101, pBI121, pDR2, pCMVEBNA, YACneo, pSVK3, pSVL, pMSG, pCH110, pKK232-8, p3'SS, pXT1, pSG5, pPbac, pMbac, pMC1neo, and pOG44, pYES2, pAC360, pBlueBacHis, pVL1392, pBlueBacIII, pCDM8, pcDNA1, pZeoSV, pcDNA3 pREP4, pCEP4, and pEBVHis.

15. The method of claim 8, wherein said prokaryotic vectors are selected from the group consisting of pcDNA II, pSL301, pSE280, pSE380, pSE420, pTrcHis, pRSET, pGEMEX-1, pGEMEX-2, pET, pTrc99A, pKK223-3, pGEX, pEZZ18, pRIT2T, pMC1871, pKK233-2, pKK388-1, and pProEx-HT.

16. The method of claim 13, wherein said 2-hybrid and reverse 2-hybrid vectors are selected from the group consisting of pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD- GAL4, pHISi, pHISi-1, placZi, pB42AD, pDG202, pJK202, pJG4-5, pNLexA, and pYESTrp.

17. The method of claim 1, wherein said Insert Donor molecules comprise a vector.

18. The method of claim 1, wherein said Insert Donor molecules comprise a DNA segment produced by amplification.

19. The method of claim 18, wherein said amplification is accomplished by PCR.

20. The method of claim 19, wherein said Insert Donor is linear.

21. The method of claim 20, wherein said Insert Donor comprises at least one recombination site at one or both termini of said linear molecule.

22. The method of claim 1, wherein said recombination sites are selected from the group consisting of loxP, attB, attP, attL, and attR.

23. (Once amended) The method of claim 1, wherein said recombination proteins are selected from the group consisting of Int, Cre, Flp, and Res.

* * * * *